US012758654B2

(12) United States Patent
Huston

(10) Patent No.: US 12,758,654 B2
(45) Date of Patent: Oct. 13, 2026

(54) METHODS AND COMPOSITIONS FOR THE TREATMENT OF FABRY DISEASE

(71) Applicant: Sangamo Therapeutics, Inc., Richmond, CA (US)

(72) Inventor: Marshall W. Huston, Richmond, CA (US)

(73) Assignee: Sangamo Therapeutics, Inc., Richmond, CA (US)

( * ) Notice: Subject to any disclaimer, the term of this patent is extended or adjusted under 35 U.S.C. 154(b) by 1142 days.

(21) Appl. No.: 17/572,189

(22) Filed: Jan. 10, 2022

(65) Prior Publication Data

US 2022/0273819 A1 Sep. 1, 2022

Related U.S. Application Data

(62) Division of application No. 15/788,059, filed on Oct. 19, 2017, now Pat. No. 11,219,695.

(60) Provisional application No. 62/552,792, filed on Aug. 31, 2017, provisional application No. 62/516,373, filed on Jun. 7, 2017, provisional application No. 62/502,058, filed on May 5, 2017, provisional application No. 62/458,324, filed on Feb. 13, 2017, provisional application No. 62/444,093, filed on Jan. 9, 2017, provisional application No. 62/410,543, filed on Oct. 20, 2016.

(51) Int. Cl.

| | |
|---|---|
| ***A61K 48/00*** | (2006.01) |
| ***A61K 38/46*** | (2006.01) |
| ***A61P 3/00*** | (2006.01) |
| ***C12N 5/071*** | (2010.01) |
| ***C12N 9/40*** | (2006.01) |
| ***C12N 15/86*** | (2006.01) |

(52) U.S. Cl.

CPC ........ *A61K 48/0058* (2013.01); *A61K 38/465* (2013.01); *A61K 48/0075* (2013.01); *A61P 3/00* (2018.01); *C12N 5/067* (2013.01); *C12N 9/2465* (2013.01); *C12N 15/86* (2013.01); *C12Y 301/00* (2013.01); *C12Y 302/01022* (2013.01); *C12N 2510/00* (2013.01); *C12N 2750/14143* (2013.01)

(58) Field of Classification Search

CPC .............. A61K 48/0058; A61K 38/465; A61K 48/0075; A61K 38/47; A61P 3/00; C12N 5/067; C12N 9/2465; C12N 15/86; C12N 2510/00; C12N 2750/14143; C12N 2800/22; C12Y 301/00; C12Y 302/01022; C07K 2319/02

See application file for complete search history.

(56) References Cited

U.S. PATENT DOCUMENTS

| | | | |
|---|---|---|---|
| 4,186,183 | A | 1/1980 | Steck et al. |
| 4,217,344 | A | 8/1980 | Vanlerberghe et al. |
| 4,235,871 | A | 11/1980 | Papahadjopoulos et al. |
| 4,261,975 | A | 4/1981 | Fullerton et al. |
| 4,485,054 | A | 11/1984 | Mezei et al. |
| 4,501,728 | A | 2/1985 | Geho et al. |
| 4,774,085 | A | 9/1988 | Fidler |
| 4,797,368 | A | 1/1989 | Carter et al. |
| 4,837,028 | A | 6/1989 | Allen |
| 4,897,355 | A | 1/1990 | Eppstein et al. |
| 4,946,787 | A | 8/1990 | Eppstein et al. |
| 5,049,386 | A | 9/1991 | Eppstein et al. |
| 5,173,414 | A | 12/1992 | Lebkowski et al. |
| 5,176,996 | A | 1/1993 | Hogan et al. |
| 5,356,802 | A | 10/1994 | Chandrasegaran |
| 5,420,032 | A | 5/1995 | Marshall et al. |
| 5,422,251 | A | 6/1995 | Fresco |
| 5,436,150 | A | 7/1995 | Chandrasegaran |
| 5,487,994 | A | 1/1996 | Chandrasegaran |
| 5,585,245 | A | 12/1996 | Johnsson et al. |
| 5,789,538 | A | 8/1998 | Rebar et al. |
| 5,925,523 | A | 7/1999 | Dove et al. |
| 6,007,988 | A | 12/1999 | Choo et al. |
| 6,008,336 | A | 12/1999 | Hanson et al. |
| 6,013,453 | A | 1/2000 | Choo et al. |
| 6,140,081 | A | 10/2000 | Barbas |
| 6,140,466 | A | 10/2000 | Barbas, III et al. |
| 6,200,759 | B1 | 3/2001 | Dove et al. |
| 6,242,568 | B1 | 6/2001 | Barbas, III et al. |
| 6,410,248 | B1 | 6/2002 | Greisman et al. |
| 6,453,242 | B1 | 9/2002 | Eisenberg et al. |
| 6,479,626 | B1 | 11/2002 | Kim et al. |
| 6,503,717 | B2 | 1/2003 | Case et al. |

(Continued)

FOREIGN PATENT DOCUMENTS

| | | | |
|---|---|---|---|
| AU | 2016206297 | A1 | 8/2016 |
| CN | 1354796 | A | 6/2002 |

(Continued)

OTHER PUBLICATIONS

Tsuji et al. "Signal sequence and DNA-mediated expression of human lysosomal α-galactosidase A". Eur. J. Biochem. 165, 275-280 (1987) (Year: 1987).*

Song et al. "Optimizing the transduction efficiency of capsid-modified AAV6 serotype vectors in primary human hematopoietic stem cells in vitro and in a xenograft mouse model in vivo". Cytotherapy, vol. 15, Issue 8, Aug. 2013, pp. 986-998. (Year: 2013).*

(Continued)

*Primary Examiner* — Brian Whiteman
*Assistant Examiner* — Amanda M Zahorik
(74) *Attorney, Agent, or Firm* — Sterne, Kessler, Goldstein & Fox P.L.L.C.

(57) ABSTRACT

Nucleases and methods of using these nucleases for inserting a sequence encoding a therapeutic α-Gal A protein such as an enzyme into a cell, thereby providing proteins or cell therapeutics for treatment and/or prevention of Fabry disease.

20 Claims, 40 Drawing Sheets

Specification includes a Sequence Listing.

(56) References Cited

U.S. PATENT DOCUMENTS 6,534,261 B1 3/2003 Cox, III et al.
6,599,692 B1 7/2003 Case et al.
6,607,882 B1 8/2003 Cox, III et al.
6,689,558 B2 2/2004 Case
6,794,136 B1 9/2004 Eisenberg et al.
6,824,978 B1 11/2004 Cox, III et al.
6,833,252 B1 12/2004 Dujon et al.
6,852,510 B2 2/2005 Bremel et al.
6,903,185 B2 6/2005 Kim et al.
6,933,113 B2 8/2005 Case et al.
6,979,539 B2 12/2005 Cox, III et al.
7,013,219 B2 3/2006 Case et al.
7,030,215 B2 4/2006 Liu et al.
7,067,317 B2 6/2006 Rebar et al.
7,070,934 B2 7/2006 Cox, III et al.
7,074,596 B2 7/2006 Darzynkiewicz et al.
7,153,949 B2 12/2006 Kim et al.
7,163,824 B2 1/2007 Cox, III et al.
7,253,273 B2 8/2007 Collingwood
7,262,054 B2 8/2007 Jamieson et al.
7,361,635 B2 4/2008 Miller et al.
7,419,829 B2 9/2008 Mitrophanous et al.
7,888,121 B2 2/2011 Urnov et al.
7,914,796 B2 3/2011 Miller et al.
7,951,925 B2 5/2011 Ando et al.
7,972,854 B2 7/2011 Miller et al.
8,021,867 B2 9/2011 Smith et al.
8,034,598 B2 10/2011 Miller
8,106,255 B2 1/2012 Carroll et al.
8,110,379 B2 2/2012 DeKelver et al.
8,153,773 B2 4/2012 Jemielity et al.
8,409,861 B2 4/2013 Guschin et al.
8,409,891 B2 4/2013 Kuriyagawa et al.
8,563,314 B2 10/2013 Gregory et al.
8,568,526 B2 10/2013 Rueger et al.
8,586,526 B2 11/2013 Gregory et al.
8,623,618 B2 1/2014 Doyon et al.
8,697,359 B1 4/2014 Zhang
8,703,489 B2 4/2014 Wang
8,771,985 B2 7/2014 Cui et al.
8,772,453 B2 7/2014 Paschon et al.
8,823,618 B2 9/2014 Lee et al.
8,895,264 B2 11/2014 Cost et al.
8,932,814 B2 1/2015 Cong et al.
8,945,868 B2 2/2015 Collingwood et al.
8,956,828 B2 2/2015 Bonini et al.
9,005,973 B2 4/2015 Cost et al.
9,045,763 B2 6/2015 DeKelver et al.
9,150,847 B2 10/2015 Rebar
9,200,266 B2 12/2015 Wang
9,206,404 B2 12/2015 Cui et al.
9,222,105 B2 12/2015 Cost et al.
9,255,250 B2 2/2016 Gregory et al.
9,255,259 B2 2/2016 Cost et al.
9,394,545 B2 7/2016 Rebar
9,447,434 B2 9/2016 Baltimore et al.
9,458,205 B2 10/2016 Gregory et al.
9,567,573 B2 2/2017 Gregory et al.
9,567,609 B2 2/2017 Paschon et al.
9,597,357 B2 3/2017 Gregory et al.
9,616,090 B2 4/2017 Conway et al.
9,816,074 B2 11/2017 Conway et al.
9,873,894 B2 1/2018 Conway et al.
9,877,988 B2 1/2018 Rebar
9,956,247 B2 5/2018 Rebar
10,081,661 B2 9/2018 Miller et al.
10,143,760 B2 12/2018 Riley et al.
10,166,298 B2 1/2019 Ansell et al.
10,179,918 B2 1/2019 Cost
10,363,269 B2 7/2019 Tareen
11,219,695 B2 1/2022 Huston
2002/0055158 A1* 5/2002 Greene .............. C07K 14/8146 435/325
2002/0106729 A1 8/2002 Bleck et al.
2003/0073652 A1* 4/2003 Pollard ................ C07K 14/745 435/372
2003/0077806 A1 4/2003 Selden et al.
2003/0232410 A1 12/2003 Liljedahl et al.
2004/0219132 A1 11/2004 Fan et al.
2005/0026157 A1 2/2005 Baltimore et al.
2005/0064474 A1 3/2005 Urnov et al.
2005/0208489 A1 9/2005 Carroll et al.
2005/0267061 A1 12/2005 Martin
2006/0063231 A1 3/2006 Li et al.
2006/0188987 A1 8/2006 Guschin et al.
2006/0189561 A1 8/2006 Roelvink et al.
2007/0117128 A1 5/2007 Smith et al.
2007/0218528 A1 9/2007 Miller
2008/0159996 A1 7/2008 Ando et al.
2009/0054985 A1 2/2009 Anderson
2009/0068164 A1 3/2009 Segal et al.
2009/0111106 A1 4/2009 Mitrophanous et al.
2010/0041151 A1 2/2010 Yew et al.
2010/0218264 A1 8/2010 Cui et al.
2010/0226912 A1 9/2010 Mehtali
2011/0265198 A1 10/2011 Gregory et al.
2011/0301073 A1 12/2011 Gregory et al.
2012/0017290 A1 1/2012 Cui et al.
2012/0195936 A1 8/2012 Rudolph et al.
2013/0122591 A1 5/2013 Cost et al.
2013/0137104 A1 5/2013 Cost et al.
2013/0177960 A1 7/2013 Rebar
2013/0177983 A1 7/2013 Rebar
2013/0196373 A1 8/2013 Gregory et al.
2014/0001721 A1 1/2014 Benko
2014/0017212 A1 1/2014 Rebar
2014/0112896 A1 4/2014 Rebar
2014/0120622 A1 5/2014 Gregory et al.
2014/0179002 A1 6/2014 Akada et al.
2014/0335063 A1 11/2014 Cannon et al.
2015/0056705 A1 2/2015 Conway et al.
2015/0151007 A1 6/2015 Dodge et al.
2015/0335708 A1 11/2015 Froelich et al.
2016/0024474 A1 1/2016 Conway et al.
2016/0030477 A1 2/2016 Conway et al.
2016/0060656 A1 3/2016 Rebar
2016/0199412 A1 7/2016 Tareen
2016/0208284 A1 7/2016 Huelsmann et al.
2016/0264953 A1 9/2016 Lee et al.
2016/0326548 A1 11/2016 Cost
2016/0375110 A1 12/2016 High et al.
2017/0119904 A1 5/2017 Ansell et al.
2017/0119906 A1 5/2017 Riley
2017/0218349 A1 8/2017 Miller et al.
2018/0087072 A1 3/2018 Miller et al.
2018/0117181 A1 5/2018 Huston
2018/0185516 A1 7/2018 Ansell et al.
2018/0311290 A1 11/2018 Sena-Esteves et al.
2019/0241877 A1 8/2019 DeKELVER et al.
2019/0358302 A1 11/2019 Gotschall
2020/0147241 A1 5/2020 Do et al.
2020/0239911 A1 7/2020 Huston
2020/0283818 A1 9/2020 Goel
2020/0299721 A1 9/2020 Kim et al.
2022/0273819 A1 9/2022 Huston

FOREIGN PATENT DOCUMENTS

CN 1750834 A 3/2006
CN 105874071 A 8/2016
CN 113423419 A 9/2021
EP 1961816 A1 8/2008
EP 1325138 B1 7/2013
GB 2338237 A 12/1999
GB 2338237 B 2/2001
JP 2002522509 A 7/2002
JP 2015527881 A 9/2015
RU 2535365 C2 7/2011
WO WO-9116024 A1 10/1991
WO WO-9117424 A1 11/1991
WO WO-9324641 A2 12/1993
WO WO-9519431 A1 7/1995
WO WO-9606166 A1 2/1996

(56) References Cited

FOREIGN PATENT DOCUMENTS

| | | | |
|---|---|---|---|
| WO | WO-9837186 | A1 | 8/1998 |
| WO | WO-9844350 | A1 | 10/1998 |
| WO | WO-9853057 | A1 | 11/1998 |
| WO | WO-9853058 | A1 | 11/1998 |
| WO | WO-9853059 | A1 | 11/1998 |
| WO | WO-9853060 | A1 | 11/1998 |
| WO | WO-9854311 | A1 | 12/1998 |
| WO | WO-0009153 | A1 | 2/2000 |
| WO | WO-0027878 | A1 | 5/2000 |
| WO | WO-0160970 | A2 | 8/2001 |
| WO | WO-0188197 | A2 | 11/2001 |
| WO | WO-0207752 | A2 | 1/2002 |
| WO | WO-0216536 | A1 | 2/2002 |
| WO | WO-02077227 | A2 | 10/2002 |
| WO | WO-02099084 | A2 | 12/2002 |
| WO | WO-03016496 | A2 | 2/2003 |
| WO | WO-2007014275 | A2 | 2/2007 |
| WO | WO-2010079430 | A1 | 7/2010 |
| WO | WO-2012115980 | A1 | 8/2012 |
| WO | WO-2014011237 | A1 | 1/2014 |
| WO | WO-2015092440 | A1 | 6/2015 |
| WO | 2016/181122 | A1 † | 11/2016 |
| WO | WO-2017201328 | A1 | 11/2017 |
| WO | WO-2018075736 | A1 | 4/2018 |
| WO | WO-2018160585 | A2 | 9/2018 |
| WO | WO-2020142752 | A1 | 7/2020 |

OTHER PUBLICATIONS

Lee et al. "A biochemical and pharmacological comparison of enzyme replacement therapies for the glycolipid storage disorder Fabry disease". Glycobiology, vol. 13, Issue 4, Apr. 2003, pp. 305-313. (Year: 2003).*

Samulski. Expanding the AAV package. Nature Biotechnology vol. 18, pp. 497-498 (2000). (Year: 2000).*

Sigma-Aldrich product sheet, Pluronic F-68, P1300, accessed Sep. 6, 2023 (2023).

Wright et al., Identification of Factors that Contribute to Recombinant AAV2 Particle Aggregation and Methods to Prevent Its Occurrence during vector purification and formulation, Mol Ther., 12(1): 171-8 (2006).

Ahmad, I., et al., "Antibody-Mediated Specific Binding and Cytotoxicity of Liposome-Entrapped Doxorubicin to Lung Cancer Cells in Vitro," Cancer Research 52(17):4817-4820, American Association for Cancer Research, United States (1992).

Alvarez R. D., et al., "A phase I Study of Recombinant Adenovirus Vector-Mediated Intraperitoneal Delivery of Herpes Simplex Virus Thymidine Kinase (HSV-TK) Gene and Intravenous Ganciclovir for Previously Treated Ovarian and Extraovarian Cancer Patients," Human Gene Therapy 8(5):597-613, Mary Ann Liebert Inc., United States (1997).

Anderson, W. F., "Human Gene Therapy," Science 256(5058):808-813, American Association for the Advancement of Science, United States (May 1992).

Arends, M., et al., "Characterization of Classical and Nonclassical Fabry Disease: a Multicenter Study," Journal of the American Society of Nephrology 28(5):1631-1641, American Society of Nephrology, United States (published online Dec. 2016, published in print May 2017).

Argast, G. M., et al., "I-PpoI and I-CreI Homing Site Sequence Degeneracy Determined by Random Mutagenesis and Sequential in Vitro Enrichment," Journal of Molecular Biology 280(3):345-353, Elsevier, Netherlands (1998).

Ashworth, J., et al., "Computational Redesign of Endonuclease DNA Binding and Cleavage Specificity," Nature 441(7093):656-659, Nature Publishing Group, United Kingdom (2006).

Bangari D.S., et al., "α-Galactosidase A knockout mice: Progressive Organ Pathology Resembles the Type 2 Later-Onset Phenotype of Fabry Disease," The American Journal of Pathology, 185(3):651-665, Elsevier, United States (2015).

Beerli, R., et al., "Engineering Polydactyl Zinc-Finger Transcription Factors," Nature biotechnology 20(2):135-141, Nature America Publishing, United States (2002).

Behr, J. P., et al., "Gene Transfer With Synthetic Cationic Amphiphiles: Prospects for Gene Therapy," Bioconjugate Chemistry 5(5):382-389, American Chemical Society, United States (1994).

Belfort, J., et al., "Homing Endonucleases: Keeping the House in Order," Nucleic Acids Research 25(17):3379-3388, Oxford University Press, United Kingdom (1997).

Benjamin E.R., et al., "Co-Administration with the Pharmacological Chaperone AT1001 Increases Recombinant Human α-Galactosidase A Tissue Uptake and Improves Substrate Reduction in Fabry Mice," Molecular Therapy, 20(4):717-726, Cell Press, United Kingdom (2012).

Benjamin E.R., et al., "The Validation of Pharmacogenetics for the Identification of Fabry Patients to be Treated with Migalastat," Genetics in Medicine, 19(4):430-438, Nature Publishing Group, United States (2017).

Bennett, J., et al., "Safety and durability of effect of contralateral-eye administration of AAV2 gene therapy in patients with childhood-onset blindness caused by RPE65 mutations: a follow-on phase 1 trial," Lancet 388(10045):661-672, Elsevier Ltd., United Kingdom (published online Jun. 2016, published in print Aug. 2016).

Bitinaite, J., et al., "FokI Dimerization is Required for DNA Cleavage," Proceedings of the National Academy of Sciences of the United States of America 95(18):10570-10575, National Academy of Sciences, United States (1998).

Blaese, M., et al., "Vectors in Cancer Therapy: How Will They Deliver?," Cancer Gene Therapy 2(4):291-297, Nature Publishing Group, United Kingdom (1995).

Blaese, R. M., et al., "T Lymphocyte-Directed Gene Therapy for ADA-SCID: Initial Trial Results After 4 Years," Science 270(5235):475-480, American Association for the Advancement of Science, United States (1995).

Boch J., et al., "Breaking the Code of DNA Binding Specificity of TAL-Type III Effectors," Science, 326(5959):1509-1512, American Association for the Advancement of Science, United States (2009).

Bonas U., et al., "Genetic and Structural Characterization of the Avirulence Gene AvrBs3 from Xanthomonas Campestris Pv. Vesicatoria," Molecular & General Genetics, 218(1):127-136, Springer-Verlag, Germany (1989).

Buchschacher, G. L., et al., "Human Immunodeficiency Virus Vectors for Inducible Expression of Foreign Genes," Journal of Virology 66(5):2731-2739, American Society for Microbiology, United States (1992).

Chang, X. B., et al., "Modification of DNA Ends Can Decrease End Joining Relative to Homologous Recombination in Mammalian Cells," Proceedings of the National Academy of Sciences of the United States of America 84(14):4959-4963, National Academy of Sciences, United States (1987).

Chevalier, B. S., et al., "Design, Activity, and Structure of a Highly Specific Artificial Endonuclease," Molecular Cell 10(4):895-905, Cell Press, United States (2002).

Choi, J.-O., et al., "Characterization of Fabry mice treated with recombinant adeno-associated virus 2/8-mediated gene transfer," Journal of Biomedical Science 17:26, 10 pages, BioMed Central Ltd., on behalf of the National Science Council, United Kingdom (Apr. 2010).

Choo, Y. and Isalan, M., "Advances in Zinc Finger Engineering," Current Opinion in Structural Biology 10(4):411-416, Elsevier Science, United Kingdom (Aug. 2000).

Christian M., et al., "Targeting DNA Double-Strand Breaks with TAL Effector Nucleases," Genetics, 186(2):757-761, Oxford University Press, Oxford. (2010).

Clarke, J. T. R., et al., "The pharmacology of multiple regimens of agalsidase alfa enzyme replacement therapy for Fabry disease," Genetics in Medicine 9(8):504-509, Lippincott Williams and Wilkins Ltd., United States (2007).

Cong L., et al., "Multiplex Genome Engineering Using CRISPR/Cas Systems," Science, 339(6121):819-823, American Association for the Advancement of Science, United States (2013).

(56) References Cited

OTHER PUBLICATIONS

Crystal, R. G., et al., "Transfer of Genes to Humans: Early Lessons and Obstacles to Success," Science 270(5235):404-410, American Association for the Advancement of Science, United States (1995).
Deegan, P. B., "Fabry disease, enzyme replacement therapy and the significance of antibody responses," Journal of Inherited Metabolic Disease 35(2):227-243, Springer, Netherlands (Oct. 2011).
Dillon, N., "Regulating Gene Expression in Gene Therapy," Trends in Biotechnology 11(5):167-173, Elsevier Science Publishers, United Kingdom (1993).
Dranoff, G., et al., "A Phase I Study of Vaccination with Autologous, Irradiated Melanoma Cells Engineered to Secrete Human Granulocyte-Macrophage Colony Stimulating Factor," Human Gene Therapy 8(1):111-123, Mary Ann Liebert Inc., United States (1997).
Dujon, B., et al., "Mobile Introns: Definition of Terms and Recommended Nomenclature," Gene 82(1):115-118, Elsevier, Netherlands (1989).
Dull, T., et al., "A Third-Generation Lentivirus Vector with a Conditional Packaging System," Journal of Virology 72(11):8463-8471, American Society for Microbiology, United States (1998).
Dunbar, C. E., et al., "Retrovirally Marked CD34-Enriched Peripheral Blood and Bone Marrow Cells Contribute to Long-Term Engraftment After Autologous Transplantation," Blood 85(11):3048-3057, American Society of Hematology, United States (1995).
Ellem, K. A., et al., "A Case Report: Immune Responses and Clinical Course of the First Human Use of Granulocyte/Macrophage-Colony-Stimulating-Factor-Transduced Autologous Melanoma Cells for Immunotherapy," Cancer Immunology, Immunotherapy, 44(1):10-20, Springer Verlag, Germany (1997).
El-Serag, H. B., and Davila, J. A., "Surveillance for hepatocellular carcinoma: in whom and how?," Therapeutic Advances in Gastroenterology 4(1):5-10, SAGE Publications Ltd., United States (Jan. 2011).
Epinat, J. C., et al., "A Novel Engineered Meganuclease Induces Homologous Recombination in Yeast and Mammalian Cells," Nucleic Acids Research 31(11):2952-2962, Oxford University Press, United Kingdom (2003).
Fagerlund R.D., et al., "The CpfI CRISPR-Cas Protein Expands Genome-Editing Tools," Genome Biology, 16:251, BioMed Central Ltd, United Kingdom (2015).
Fields, S., and Song, O., "A Novel Genetic System to Detect Protein-protein Interactions," Nature 340(6230):245-246, Nature Publishing Group, United Kingdom (Jul. 1989).
Follenzi, A., et al., "Gene Transfer by Lentiviral Vectors is Limited by Nuclear Translocation and Rescued by HIV-1 Pol Sequences," Nature Genetics 25(2):217-222, Nature Publishing Group, United Kingdom (2000).
Gabathuler, R., "Approaches to transport therapeutic drugs across the blood-brain barrier to treat brain diseases," Neurobiology of Disease 37(1):48-57, Elsevier, Netherlands (2010).
Gao, X., et al., "Cationic Liposome-Mediated Gene Transfer," Gene Therapy 2(10):710-722, Nature Publishing Group, United Kingdom (1995).
Garman, S. C., et al., "The Molecular Defect Leading to Fabry Disease: Structure of Human Alpha-Galactosidase," Journal of Molecular Biology 337(2):319-335, Elsevier, Netherlands (2004).
Gimble, F. S., et al., "Substrate Recognition and Induced DNA Distortion by the PI-Scel Endonuclease, an Enzyme Generated by Protein Splicing," Journal of Molecular Biology 263(2):163-180, Elsevier, Netherlands (1996).
Guo J., et al., "Directed Evolution of an Enhanced and Highly Efficient FokI Cleavage Domain for Zinc Finger Nucleases," Journal of Molecular Biology, 400(1):96-107, Elsevier, Netherlands (2010).
Haddada, H., et al., "Gene Therapy Using Adenovirus Vectors" in Molecular Repertoire of Adenoviruses III, pp. 297-306, Doerfler, W., et al., eds., part of the Current Topics in Microbiology and Immunology book series, Springer-Verlag, Germany (1995).
Haft, D.H., et al., "A Guild of 45 CRISPR-Associated (Cas) Protein Families and Multiple Crispr/Cas Subtypes Exist in Prokaryotic Genomes," PLoS Computational Biology 1(6):e60, Public Library of Science, United States (2005).
Han, X., et al., "Ligand-Directed Retroviral Targeting of Human Breast Cancer Cells," Proceedings of the National Academy of Sciences of the United States of America 92(21):9747- 9751, National Academy of Sciences, United States (1995).
Hartl F.U., et al., "Molecular Chaperones in Protein Folding and Proteostasis," Nature, 475(7356):324-332, Nature Publishing Group, Basingstoke. (2011).
Hermonat, P. L., et al., "Use of Adeno-Associated Virus as a Mammalian DNA Cloning Vector: Transduction of Neomycin Resistance into Mammalian Tissue Culture Cells," Proceedings of the National Academy of Sciences of the United States of America 81(20):6466-6470, National Academy of Sciences, United States (1984).
Heuer H., et al., "Repeat Domain Diversity of AvrBs3-Like Genes in Ralstonia Solanacearum Strains and Association with Host Preferences in the Field," Applied and Environmental Microbiology, 73(13):4379-4384, American Society for Microbiology, United States (2007).
International Search Report and Written Opinion for International Application No. PCT/US2017/057328, ISA/US, Commissioner for Patents, Alexandria, Virginia, mailed on Mar. 13, 2018, 14 pages.
International Search Report and Written Opinion for Application No. PCT/US2020/012274, mailed on Apr. 21, 2020, 12 pages.
Isalan, M., et al., "A Rapid, Generally Applicable Method to Engineer Zinc Fingers Illustrated by Targeting the HIV-1 Promoter," Nature Biotechnology 19:656-660, Nature America Publishing, United States (Jul. 2001).
Jansen R., et al., "Identification of Genes that are Associated with DNA Repeats in Prokaryotes," Molecular Microbiology, 43(6):1565-1575, Blackwell Scientific Publications, Oxford. (2002).
Jasin, M., et al., "Genetic Manipulation of Genomes with Rare-Cutting Endonucleases," Trends in Genetics 12(6):224-228, Elsevier Trends Journals, United States (1996).
Johann, S. V., et al., "GLVR1, a Receptor for Gibbon Ape Leukemia Virus, is Homologous to a Phosphate Permease of Neurospora Crassa and is Expressed at High Levels in the Brain and Thymus," Journal of Virology 66(3):1635-1640, American Society for Microbiology, United States (1992).
Jung S.C., et al., "Adeno-Associated Viral Vector-Mediated Gene Transfer Results in Long-Term Enzymatic and Functional Correction in Multiple Organs of Fabry Mice," Proceedings of the National Academy of Sciences of the United States of America, 98(5):2676-2681, National Academy of Sciences, United States (2001).
Kay S., et al., "A Bacterial Effector Acts as a Plant Transcription Factor and Induces a Cell Size Regulator," Science, 318(5850):648-651, American Association for the Advancement of Science, United States (2007).
Kearns, W. G., et al., "Recombinant Adeno-Associated Virus (AAV-CFTR) Vectors Do Not Integrate in a Site-Specific Fashion in an Immortalized Epithelial Cell Line," Gene Therapy 3(9):748-755, Nature Publishing Group, United Kingdom (1996).
Khanna R., et al., "The Pharmacological Chaperone AT2220 Increases the Specific Activity and Lysosomal Delivery of Mutant Acid Alpha-Glucosidase, and Promotes Glycogen Reduction in a Transgenic Mouse Model of Pompe Disease," Plos One, 9(7):e102092, Public Library of Science, San Francisco. (2014).
Kim, Y. G., et al., "Chimeric Restriction Endonuclease," Proceedings of the National Academy of Sciences of the United States of America 91(3):883-887, National Academy of Sciences, United States (1994).
Kim, Y. G., et al., "Hybrid Restriction Enzymes: Zinc Finger Fusions to Fok I Cleavage Domain," Proceedings of the National Academy of Sciences of the United States of America 93(3):1156-1160, National Academy of Sciences, United States (1996).
Kim, Y. G., et al., "Insertion and Deletion Mutants of FokI Restriction Endonuclease," The Journal of Biological Chemistry 269(50):31978-31982, Elsevier Inc., Netherlands (1994).
Kohn, D. B., et al., "Engraftment of Gene-Modified Umbilical Cord Blood Cells in Neonates with Adenosine Deaminase Deficiency," Nature Medicine 1(10):1017-1023, Nature Publishing Company, United States (1995).

(56) References Cited

OTHER PUBLICATIONS

Kormann, M.S., et al., "Expression of therapeutic proteins after delivery of chemically modified mRNA in mice," Nature Biotechnology 29(2):154-157, Nature America Publishing, United States (2011).
Kotin, R. M., "Prospects for The Use of Adeno-Associated Virus as a Vector for Human Gene Therapy," Human Gene Therapy 5(7):793-801, Mary Ann Liebert Inc., United States (1994).
Kozak, M., et al., "An Analysis of 5'-Noncoding Sequences from 699 Vertebrate Messenger RNAs," Nucleic Acids Research 15(20):8125-8148, Oxford University Press, United Kingdom (1987).
Kremer, E. J., et al., "Adenovirus and Adeno-Associated Virus Mediated Gene Transfer," British Medical Bulletin 51(1):31-44, Oxford University Press, United Kingdom (1995).
Lee, H. Y., et al., "Nanoparticle-Based Targeted Gene Therapy for Lung Cancer," American Journal of Cancer Research 6(5):1118-1134, e-Century Pub. Corp., United States (May 2016).
Lheriteau, E., et al., "Haemophilia Gene Therapy: Progress and Challenges," Blood Reviews 29(5):321-328, Elsevier, United Kingdom (Sep. 2015).
Li, L., et al., "Functional Domains in Fok I Restriction Endonuclease," Proceedings of the National Academy of Sciences of the United States of America 89(10):4275-4279, National Academy of Sciences, United States (1992).
Li, L., et al., "Alteration of the Cleavage Distance of Fok I Restriction Endonuclease by Insertion Mutagenesis," Proceedings of the National Academy of Sciences of the United States of America, 90(7):2764-2768, National Academy of Sciences, United States (1993).
Linthorst, G. E., et al., "Enzyme therapy for Fabry disease: neutralizing antibodies toward agalsidase alpha and beta," Kidney Int 66(4):1589-1595, Elsevier, Netherlands (2004).
Luke, G. A., et al., "Occurrence, Function and Evolutionary Origins of '2A-like' Sequences in Virus Genomes," The Journal of General Virology 89(4):1036-1042, Microbiology Society, United Kingdom (2008).
Macdiarmid, J. A., et al., "Sequential Treatment of Drug-Resistant Tumors With Targeted Minicells Containing SiRNA or a Cytotoxic Drug," Nature Biotechnology 27(7):643-651, Nature America Publishing, United States (2009).
Makarova K.S., et al., "A DNA Repair System Specific for Thermophilic Archaea and Bacteria Predicted by Genomic Context Analysis," Nucleic Acids Research, 30(2):482-496, Oxford University Press ,Oxford. (2002).
Makarova K.S., et al., "A Putative RNA-Interference-Based Immune System in Prokaryotes: Computational Analysis of the Predicted Enzymatic Machinery, Functional Analogies with Eukaryotic RNAi, and Hypothetical Mechanisms of Action," Biology Direct, 1:7, BioMed Central, United Kingdom (2006).
Malech, H. L., et al., "Prolonged Production of NADPH Oxidase-Corrected Granulocytes After Gene Therapy of Chronic Granulomatous Disease," Proceedings of the National Academy of Sciences of the United States of America 94(22):12133-12138, National Academy of Sciences, United States (1997).
Manno, C. S., et al., "Successful transduction of liver in hemophilia by AAV-Factor IX and limitations imposed by the host immune response," Nature Medicine 12(3):342-347, Nature Publishing Group, United Kingdom (published online Feb. 2006, published in print Mar. 2006).
Matsukado, K., et al., "Enhanced Tumor Uptake of Carboplatin and Survival in Glioma-Bearing Rats by Intracarotid Infusion of Bradykinin Analog, RMP-7," Neurosurgery 39(1):125-133, Oxford University Press, United Kingdom (1996).
Meghdari M., et al., "Carboxyl-Terminal Truncations Alter the Activity of the Human α-Galactosidase A," PloS one, 10(2):e0118341, Public Library of Science, San francisco. (2015).
Miao, C. H., et al., "Inclusion of the Hepatic Locus Control Region, an Intron, and Untranslated Region Increases and Stabilizes Hepatic Factor IX Gene Expression in Vivo but Not in Vitro," Molecular Therapy 1(6):522-532, Cell Press, United States (2000).
Miller, A. D., et al., "Construction and Properties of Retrovirus Packaging Cells Based on Gibbon Ape Leukemia Virus," Journal of Virology 65(5):2220-2224, American Society for Microbiology, United States (1991).
Miller, A. D., et al., "Human Gene Therapy Comes of Age," Nature 357(6378):455-460, Nature Publishing Group, United Kingdom (1992).
Mitani, K., et al., "Delivering Therapeutic Genes—Matching Approach and Application," Trends in Biotechnology 11(5):162-166, Elsevier Science Publishers, United Kingdom (1993).
Moise A., et al., "Substrate and Substrate-Mimetic Chaperone Binding Sites in Human α-Galactosidase A Revealed by Affinity-Mass Spectrometry," Journal of the American Society for Mass Spectrometry, 27(6):1071-1078, ACS Publications, United States (2016).
Moscou J.M., et al., "A Simple Cipher Governs DNA Recognition by TAL Effectors," Science, 326(5959):1501, American Association for the Advancement of Science, United States (2009).
Muzyczka, N., "Adeno-Associated Virus (AAV) Vectors: Will They Work?," The Journal of Clinical Investigation 94(4):1351, American Society for Clinical Investigation, Ann Arbor. (1994).
Nabel, G. J., and Felgner, P. L., "Direct Gene Transfer for Immunotherapy and Immunization," Trends in Biotechnology 11(5):211-215, Elsevier Science Publishers, Netherlands (May 1993).
Nakai, H., et al., "Extrachromosomal recombinant adeno-associated virus vector genomes are primarily responsible for stable liver transduction in vivo," Journal of Virology 75(15):6969-6976, American Society for Microbiology, United States (Aug. 2001).
Naldini, L., et al., "Efficient Transfer, Integration, and Sustained Long-Term Expression of the Transgene in Adult Rat Brains Injected with a Lentiviral Vector," Proceedings of the National Academy of Sciences of the United States of America 93(21):11382-11388, National Academy of Sciences, United States (1996).
Nathwani, A. C., et al., "Long-term safety and efficacy of factor IX gene therapy in hemophilia B," New England Journal of Medicine 371(21):1994-2004, Massachusetts Medical Society, United States (Nov. 2014).
Nehls, M., et al., "Two Genetically Separable Steps in the Differentiation of Thymic Epithelium," Science 272(5263):886-889, American Association for the Advancement of Science, United States (1996).
Okuyama, T., et al., "Liver-Directed Gene Therapy: a Retroviral Vector with a Complete LTR and the ApoE Enhancer-Alpha 1-Antitrypsin Promoter Dramatically Increases Expression of Human Alpha 1-Antitrypsin in Vivo," Human Gene Therapy 7(5):637-645, Mary Ann Liebert Inc., United States (1996).
Olovnikov I., et al., "Bacterial Argonaute Samples the Transcriptome to Identify Foreign DNA," Molecular cell, 51(5):594-605, Cell Press, United Kingdom (2013).
Ong, J. M., et al., "The WPRE Improves Genetic Engineering With Site-Specific Nucleases," BioRxiv, Cold Spring Harbor Laboratory, United States (Apr. 2017).
Pabo, C.O., et al., "Design and Selection of Novel Cys2His2 Zinc Finger Proteins," Annual Review of Biochemistry 70:313-340, Annual Reviews, United States (2001).
Paques, F., et al., "Meganucleases and DNA Double-Strand Break-Induced Recombination: Perspectives for Gene Therapy," Current Gene Therapy 7(1):49-66, Bentham Science Publishers, United Arab Emirates (2007).
Passineau M.J., et al., "α-Galactosidase A Expressed in the Salivary Glands Partially Corrects Organ Biochemical Deficits in the Fabry Mouse Through Endocrine Trafficking," Human Gene Therapy, 22(3):293-301, Liebert, United States (2011).
Penaud-Budloo, M., et al., "Pharmacology of Recombinant Adeno-associated Virus Production," Molecular Therapy. Methods & Clinical Development 8:166-180, Cell Press, United States (Jan. 2018).
Perler, F. B., et al., "Protein Splicing Elements: Inteins and Exteins—a Definition of Terms and Recommended Nomenclature," Nucleic Acids Research 22(7):1125-1127, Oxford University Press, United Kingdom (1994).

(56) References Cited

OTHER PUBLICATIONS

Ponder K.P., "Immune Response Hinders Therapy for Lysosomal Storage Diseases," The Journal of Clinical Investigation, 118(8):2686-2689, American Society for Clinical Investigation, United States (2008).
Remy, J. S., et al., "Gene Transfer With a Series of Lipophilic DNA-Binding Molecules," Bioconjugate Chemistry 5(6):647-654, American Chemical Society, United States (1994).
Roberts, R. J., et al., "REBASE: Restriction Enzymes and Methyltransferases," Nucleic Acids Research 31(1):418-420, Oxford University Press, United Kingdom (2003).
Rosenecker, J., et al., "Adenovirus Infection in Cystic Fibrosis Patients: Implications for the Use of Adenoviral Vectors for Gene Transfer," Infection 24(1):5-8, Springer, Germany (1996).
Samulski, R. J., et al., "Helper-Free Stocks of Recombinant Adeno-Associated Viruses: Normal Integration Does Not Require Viral Gene Expression," Journal of Virology 63(9):3822-3828, American Society for Microbiology, United States (1989).
Schornack S., et al., "Gene-for-Gene-Mediated Recognition of Nuclear-Targeted AvrBs3-like Bacterial Effector Proteins," Journal of Plant Physiology, 163(3):256-257, Urban & Fischer, Germany. (2006).
Segal, D.J. and Barbas 3rd, C.F., "Custom DNA-Binding Proteins Come of Age: Polydactyl Zinc-Finger Proteins," Current Opinion in Biotechnology 12(6):632-637, Elsevier, United Kingdom (Dec. 2001).
Sharma, R., et al., "In vivo genome editing of the albumin locus as a platform for protein replacement therapy," Blood 126(15):1777-1784, American Society of Hematology, United States (2015).
Sheng, G., et al., "Structure-based cleavage mechanism of Thermus thermophilus Argonaute DNA guide strand-mediated DNA target cleavage," Proc Natl Acad Sci USA 111(2):652-657, National Academy of Science, United States (published online Dec. 2013, published in print Jan. 2014).
Sommerfelt, M. A., et al., "Receptor Interference Groups of 20 Retroviruses Plating on Human Cells," Virology 176(1):58-69, Academic Press, United States (1990).
Sterman, D. H., et al., "Adenovirus-Mediated Herpes Simplex Virus Thymidine Kinase/Ganciclovir Gene Therapy in Patients with Localized Malignancy: Results of a Phase I Clinical trial in Malignant Mesothelioma," Human Gene Therapy 9(7):1083-1092, Mary Ann Liebert Inc., United States (1998).
Swarts, D. C., et al., "DNA-guided DNA interference by a prokaryotic Argonaute," Nature 507(7491):258-261, Nature Publishing Group, United Kingdom (2014).
Tebas P., et al., "Gene Editing of CCR5 in Autologous CD4 T Cells of Persons Infected with HIV," The New England Journal of Medicine, 370(10):901-910, Massachusetts Medical Society, Boston. (2014).
Third Party Observation dated Oct. 18, 2021, mailed on Oct. 21, 2021, submitted in European Application No. EP 17861799.9, filed Oct. 19, 2017, 5 pages.
Topf, N., et al., "Regional 'Pro-Drug' Gene Therapy: Intravenous Administration of an Adenoviral Vector Expressing the *E. coli* Cytosine Deaminase Gene and Systemic Administration of 5-Fluorocytosine Suppresses Growth of Hepatic Metastasis of Colon Carcinoma," Gene Therapy 5(4):507-513, Nature Publishing Group, United Kingdom (1998).
Tratschin, J. D., et al., "A Human Parvovirus, Adeno-Associated Virus, as a Eucaryotic Vector: Transient Expression and Encapsidation of the Procaryotic Gene for Chloramphenicol Acetyltransferase," Molecular and Cellular Biology 4(10):2072-2081, American Society for Microbiology, United States (1984).
Tratschin, J. D., et al., "Adeno-Associated Virus Vector for High-Frequency Integration, Expression, and Rescue of Genes in Mammalian Cells," Molecular and Cellular Biology 5(11):3251-3260, American Society for Microbiology, United States (1985).
Van Brunt, J., et al., "Molecular Farming: Transgenic Animals as Bioreactors," Biotechnology 6(10):1149-1154, Nature Publishing Co., United States (1988).
Vigne, E., et al., "Third-Generation Adenovectors for Gene Therapy," Restorative Neurology and Neuroscience 8(1):35-36, IOS Press, Netherlands (1995).
Vogel J., "Biochemistry. A Bacterial Seek-and-Destroy System for Foreign DNA," Science, 344(6187):972-973, American Association for the Advancement of Science, United States (2014).
Wagner, J. A., et al., "Efficient and Persistent Gene Transfer of AAV-CFTR in Maxillary Sinus," Lancet 351(9117):1702-1703, Elsevier, United Kingdom (1998).
Welsh, M. J., et al., "Adenovirus-Mediated Gene Transfer for Cystic Fibrosis: Part A. Safety of Dose and Repeat Administration in the Nasal Epithelium. Part B. Clinical Efficacy in the Maxillary Sinus," Human Gene Therapy 6(2):205-218, Mary Ann Liebert Inc., United States (1995).
West, M. H., et al., "Gene Expression in Adeno-Associated Virus Vectors: the Effects of Chimeric MRNA Structure, Helper Virus, and Adenovirus VA1 RNA," Virology 160(1):38-47, Academic Press, United States (1987).
Wilson, C., et al., "Formation of Infectious Hybrid Virions With Gibbon Ape Leukemia Virus and Human T-Cell Leukemia Virus Retroviral Envelope Glycoproteins and the Gag and Pol Proteins of Moloney Murine Leukemia Virus," Journal of Virology 63(5):2374-2378, American Society for Microbiology, United States (1989).
Winchester, B., and Young, E., "18. Biochemical and genetic diagnosis of Fabry disease," in Fabry Disease: Perspectives from 5 Years of FOS, Mehta, A., et al., eds., Oxford PharmaGenesis, United Kingdom (2006).
Yu, M., et al., "Progress Towards Gene Therapy for HIV Infection," Gene Therapy 1(1):13-26, Nature Publishing Group, United Kingdom (1994).
Yuan Y.R., et al., "Crystal Structure of A. Aeolicus Argonaute, a Site-Specific DNA-Guided Endoribonuclease, Provides Insights Into RISC-Mediated MRNA Ceavage," Molecular Cell, 19(3):405-419, Cell Press, United Kingdom (2005).
Zanta-Boussif, M. A., et al., "Validation of a Mutated PRE Sequence Allowing High and Sustained Transgene Expression While Abrogating WHV-X Protein Synthesis: Application to the Gene Therapy of WAS," Gene Therapy 16(5):605-619, Nature Publishing Group, United Kingdom (2009).
Zetsche, B., et al., "Cpf1 is a Single RNA-Guided Endonuclease of a Class 2 CRISPR-Cas System," Cell 163(3):759-771, Cell Press, United States (Oct. 2015).
Zuffery, R., et al., "Self-Inactivating Lentivirus Vector for Safe and Efficient in Vivo Gene Delivery," Journal of Virology 72(12):9873-9880, American Society for Microbiology, United States (1998).
Zufferey, R., et al., "Woodchuck hepatitis virus posttranscriptional regulatory element enhances expression of transgenes delivered by retroviral vectors," Journal of Virology 73(4):2886-2892, American Society for Microbiology, United States (Apr. 1999).
Park, J., et al., "Long-term Correction of Globotriaosylceramide Storage in Fabry Mice by Recombinant Adeno- Associated Virus-mediated Gene Transfer," Proceedings of the National Academy of Sciences of the United States of America 100(6):3450-3454, National Academy of Sciences, United States (Mar. 2003).
Huston, M.W., et al., "Liver-based expression of the human alpha-galactosidae A gene (GLA) in a murine Fabry model results in continuous supra-physiological enzyme activity and effective substrate reduction," Molecular Genetics and Metabolism 117:169, Elsevier, Netherlands (Feb. 2017).
Hopkin, R. et al. "Isaralgagene Civaparvovec (ST-920) Shows Positive Mean Annualized eGFR Slope in Adults with Fabry Disease: Updated Results from the Registrational Phase ½ STAAR Gene Therapy Study" Presented at the International Congress of Inborn Errors of Metabolism (ICIEM) 2025, Kyoto, Japan, Sep. 2-6, 2025.
Sofronview, M. et al. "Astrocytes: biology and pathology" Acta Neuropathol (2010) 119:7-35, Published Dec. 10, 2009, 29 pages.
Yasuda, M. et al. "AAV2/6 Gene Therapy in a Murine Model of Fabry Disease Results in Supraphysiological Enzyme Activity and Effective Substrate Reduction" Molecular Therapy, Methods and Clinical Development vol. 18. (Sep. 2020), New York, 13 Pages.
Okuyama et al., 1996, 'Liver-directed gene therapy: a retroviral vector with a complete LTR and the ApoE enhancer-alpha 1-antitrypsin

(56) References Cited

OTHER PUBLICATIONS promoter dramatically increases expression of human alpha 1-antitrypsin in vivo' Hum. Gene Ther., 7(5):637-45, published Mar. 20, 1996.†

* cited by examiner
† cited by third party

* Individual mouse given DGJ molecular chaperone on indicated day

Data sets are shown L->R:
plasma liver heart kidney

Plasma GLA Activity
WT range
25%
nmol/hr/ml
WT
GLA-KO
D0
D7
D14
D28
D42
D56
D70
D84
D90
no IS
+ IS
2/8 ZFN+donor indels in liver, Day 90
% indels in liver
donor only
no IS
+ IS WT range
nmol/hr/ml
time(days)
ZFN+Donor low IS
ZFN+Donor moderate IS
ZFN+Donor high IS low IS moderate IS high IS Plasma α-Gal activity

| group | GLAKO | ZFN+Donor+DGJ | cDNA low | cDNA high | WT |
|---|---|---|---|---|---|
| plasma α-GalA activity (group average) nmol/hr/mg protein | 0.6 | 8.8 | 35.9 | 1387.5 | 8.5 |

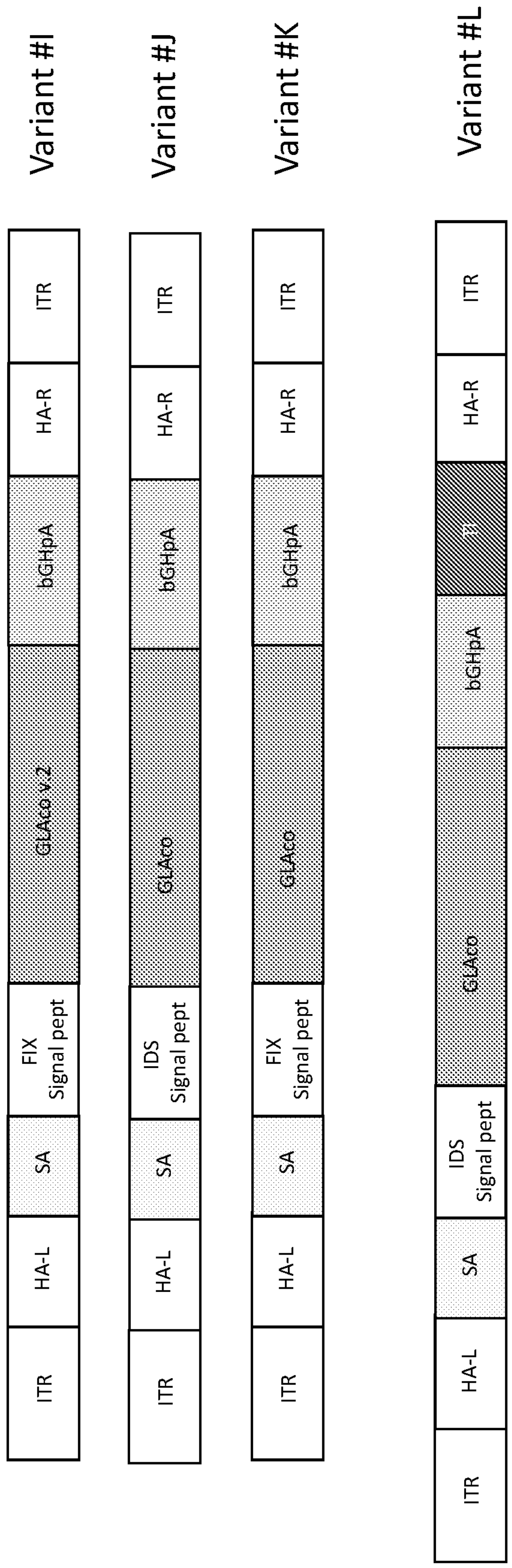
Figure 10, continued bars L->R
plasma
liver
heart
kidney

Figure 17B
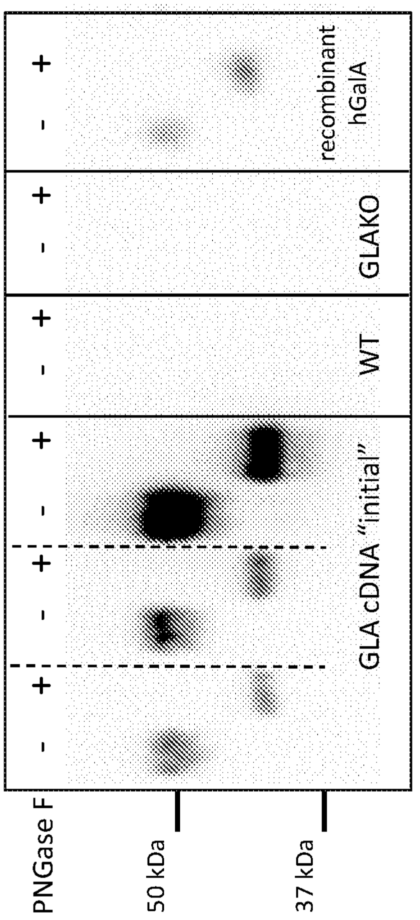
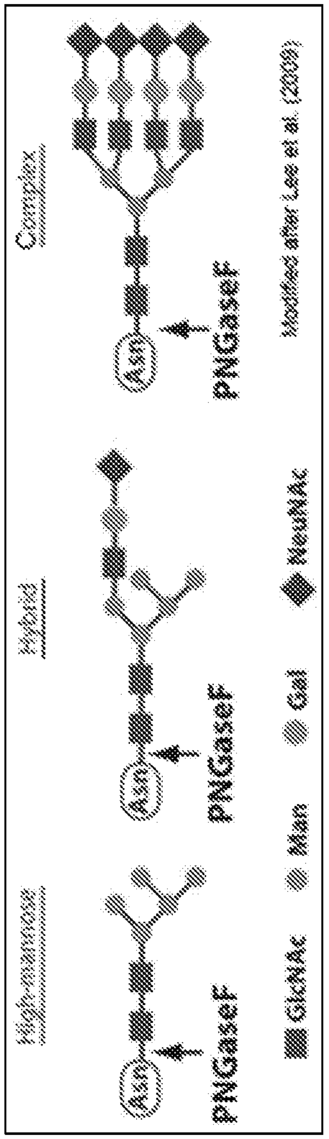
Figure 17C

METHODS AND COMPOSITIONS FOR THE TREATMENT OF FABRY DISEASE

CROSS-REFERENCE TO RELATED APPLICATIONS

The present application is a divisional of U.S. application Ser. No. 15/788,059, filed Oct. 19, 2017 (now U.S. Pat. No. 11,219,695, issued Jan. 11, 2022), which claims the benefit of U.S. Provisional Application No. 62/410,543, filed Oct. 20, 2016; U.S. Provisional Application No. 62/444,093, filed Jan. 9, 2017; U.S. Provisional Application No. 62/458,324, filed Feb. 13, 2017; U.S. Provisional Application No. 62/502,058, filed May 5, 2017; U.S. Provisional No. 62/516,373, filed Jun. 7, 2017; and U.S. Provisional Application No. 62/552,792, filed Aug. 31, 2017, the disclosures of which are hereby incorporated by reference in their entireties.

REFERENCE TO SEQUENCE LISTING SUBMITTED ELECTRONICALLY VIA EFS-WEB

The content of the electronically submitted sequence listing (Name: 4341_0180008_Seqlisting_ST25; Size: 7,535 bytes; and Date of Creation: Jan. 7, 2022) is incorporated herein by reference in its entirety.

TECHNICAL FIELD

The present disclosure is in the field of the prevention and/or treatment of Fabry Disease and gene therapy.

BACKGROUND

Gene therapy holds enormous potential for a new era of human therapeutics. These methodologies will allow treatment for conditions that heretofore have not been addressable by standard medical practice. One area that is especially promising is the ability to add a transgene to a cell to cause that cell to express a product that previously was not being produced in that cell or was being produced suboptimally. Examples of uses of this technology include the insertion of a gene encoding a therapeutic protein, insertion of a coding sequence encoding a protein that is somehow lacking in the cell or in the individual and insertion of a sequence that encodes a structural nucleic acid such as a microRNA.

Transgenes can be delivered to a cell by a variety of ways, such that the transgene becomes integrated into the cell's own genome and is maintained there. In recent years, a strategy for transgene integration has been developed that uses cleavage with site-specific nucleases for targeted insertion into a chosen genomic locus (see, e.g., co-owned U.S. Pat. No. 7,888,121). Nucleases, such as zinc finger nucleases (ZFNs), transcription activator-like effector nucleases (TALENs), or nuclease systems such as the RNA guided CRISPR/Cas system (utilizing an engineered guide RNA), are specific for targeted genes and can be utilized such that the transgene construct is inserted by either homology directed repair (HDR) or by end capture during non-homologous end joining (NHEJ) driven processes. See, e.g., U.S. Pat. Nos. 9,394,545; 9,255,250; 9,200,266; 9,045,763; 9,005,973; 9,150,847; 8,956,828; 8,945,868; 8,703,489; 8,586,526; 6,534,261; 6,599,692; 6,503,717; 6,689,558; 7,067,317; 7,262,054; 7,888,121; 7,972,854; 7,914,796; 7,951,925; 8,110,379; 8,409,861; U.S. Patent Publications 20030232410; 20050208489; 20050026157; 20050064474; 20060063231; 20080159996; 201000218264; 20120017290; 20110265198; 20130137104; 20130122591; 20130177983; 20130196373; 20140120622; 20150056705; 20150335708; 20160030477 and 20160024474, the disclosures of which are incorporated by reference in their entireties.

Transgenes may be introduced and maintained in cells in a variety of ways. Following a "cDNA" approach, a transgene is introduced into a cell such that the transgene is maintained extra-chromosomally rather than via integration into the chromatin of the cell. The transgene may be maintained on a circular vector (e.g. a plasmid, or a non-integrating viral vector such as AAV or Lentivirus), where the vector can include transcriptional regulatory sequences such as promoters, enhancers, polyA signal sequences, introns, and splicing signals (U.S. Publication No. 20170119906). An alternate approach involves the insertion of the transgene in a highly expressed safe harbor location such as the albumin gene (see U.S. Pat. No. 9,394,545). This approach has been termed the In Vivo Protein Replacement Platform® or IVPRP. Following this approach, the transgene is inserted into the safe harbor (e.g., Albumin) gene via nuclease-mediated targeted insertion where expression of the transgene is driven by the Albumin promoter. The transgene is engineered to comprise a signal sequence to aid in secretion/excretion of the protein encoded by the transgene.

"Safe harbor" loci include loci such as the AAVS1, HPRT, Albumin and CCR5 genes in human cells, and Rosa26 in murine cells. See, e.g., U.S. Pat. Nos. 7,888,121; 7,972,854; 7,914,796; 7,951,925; 8,110,379; 8,409,861; 8,586,526; U.S. Patent Publications 20030232410; 20050208489; 20050026157; 20060063231; 20080159996; 201000218264; 20120017290; 20110265198; 20130137104; 20130122591; 20130177983; 20130177960 and 20140017212. Nuclease-mediated integration offers the prospect of improved transgene expression, increased safety and expressional durability, as compared to classic integration approaches that rely on random integration of the transgene, since it allows exact transgene positioning for a minimal risk of gene silencing or activation of nearby oncogenes.

While delivery of the transgene to the target cell is one hurdle that must be overcome to fully enact this technology, another issue that must be conquered is insuring that after the transgene is inserted into the cell and is expressed, the gene product so encoded must reach the necessary location with the organism, and be made in sufficient local concentrations to be efficacious. For diseases characterized by the lack of a protein or by the presence of an aberrant non-functional one, delivery of a transgene encoded wild type protein can be extremely helpful.

Lysosomal storage diseases (LSDs) are a group of rare metabolic monogenic diseases characterized by the lack of functional individual lysosomal proteins normally involved in the breakdown of waste lipids, glycoproteins and mucopolysaccharides. These diseases are characterized by a buildup of these compounds in the cell since it is unable to process them for recycling due to the mis-functioning of a specific enzyme. The most common examples are Gaucher's (glucocerebrosidase deficiency—gene name: GBA), Fabry's (a galactosidase A deficiency—GLA), Hunter's (iduronate-2-sulfatase deficiency—IDS), Hurler's (alpha-L iduronidase deficiency—IDUA), Pompe's (alpha-glucosidase (GAA)) and Niemann-Pick's (sphingomyelin phosphodiesterase 1 deficiency—SMPD1) diseases. When grouped all together, LSDs have an incidence in the population of about 1 in 7000 births. See, also, U.S. Patent Publication Nos. 20140017212; 2014-0112896; and 20160060656.

For instance, Fabry disease is an X-linked disorder of glycosphingolipid metabolism caused by a deficiency of the α-galactosidase A enzyme (α-GalA). It is associated with the progressive deposition of glycospingolipids including globotriaosylceramide (also known as GL-3 and Gb3) and globotriaosylsphingosine (lyso-Gb3), galabioasylceramide, and group B substance. Symptoms of the disease are varied and can include burning, tingling pain (acroparesthesia) or episodes of intense pain which are called 'Fabry crises' which can last from minutes to days. Other symptoms include impaired sweating, low tolerance for exercise, reddish-purplish rash called angiokeratoma, eye abnormalities, gastrointestinal problems, heart problems such as enlarged heart and heart attack, kidney problems that can lead to renal failure and CNS problems and in general, life expectancy for Fabry patients is shortened substantially.

Current treatment for Fabry disease can involve enzyme replacement therapy (ERT) with two different preparations of human α-GalA, agalsidase beta or agalsidase alfa, which requires costly and time consuming infusions (typically between about 0.2-1 mg/kg) for the patient every two weeks. Such treatment is only to treat the symptoms and is not curative, thus the patient must be given repeated dosing of these proteins for the rest of their lives, and potentially may develop neutralizing antibodies to the injected protein.

Furthermore, adverse reactions are associated with ERT, including immune reactions such as the development of anti-α-GalA antibodies in subjects treated with the α-GalA preparations. In fact, 50% of males treated with agalsidase alfa and 88% of males treated with agalsidase beta developed α-GalA antibodies. Importantly, a significant proportion of those antibodies are neutralizing antibodies and, accordingly, reduce the therapeutic impact of the therapy (Meghdari et al (2015) *PLoS One* 10(2):e0118341. Doi: 10.1371/journal.pone.0118341). In addition, ERT does not halt disease progression in all patients.

Thus, there remains a need for non-ERT methods and compositions that can be used to treat Fabry disease, including treatment through genome editing, for instance, to deliver an expressed transgene encoded gene product at a therapeutically relevant level.

SUMMARY

Disclosed herein are methods and compositions for treating and/or preventing Fabry disease. The invention describes methods for insertion of a transgene sequence into a suitable target cell (e.g., a subject with Fabry disease) wherein the transgene encodes at least one protein (e.g., at least one α-GalA protein) that treats the disease. The methods may be in vivo (delivery of the transgene sequence to a cell in a living subject) or ex vivo (delivery of modified cells to a living subject). The invention also describes methods for the transfection and/or transduction of a suitable target cell with an expression system such that an α-GalA encoding transgene expresses a protein that treats (e.g., alleviates one or more of the symptoms associated with) the disease. The α-GalA protein may be excreted (secreted) from the target cell such that it is able to affect or be taken up by other cells that do not harbor the transgene (cross correction). The invention also provides for methods for the production of a cell (e.g., a mature or undifferentiated cell) that produces high levels of α-GalA where the introduction of a population of these altered cells into a patient will supply that needed protein to treat a disease or condition. In addition, the invention provides methods for the production of a cell (e.g. a mature or undifferentiated cell) that produces a highly active form (therapeutic) of α-GalA where the introduction of, or creation of, a population of these altered cells in a patient will supply that needed protein activity to treat (e.g., reduce or eliminate one or more symptoms) Fabry's disease. The highly active form of α-GalA produced as described herein can also be isolated from cells as described herein and administered to a patient in need thereof using standard enzyme replacement procedures known to the skilled artisan.

Described herein are methods and compositions for expressing at least one a galactosidase A (α-Gal A) protein. The compositions and methods can be for use in vitro, in vivo or ex vivo, and comprise administering a GLA transgene (e.g., cDNA with wild-type or codon optimized GLA sequences) encoding the at least one α-Gal A protein to the cell such that the α-Gal A protein is expressed in the cell. In certain embodiments, the cell is in a subject with Fabry's disease. In any of the methods described herein, the transgene can be administered to the liver of the subject. Optionally, the methods further comprise administering one or more nucleases that cleave an endogenous albumin gene in a liver cell in a subject such that the transgene is integrated into and expressed from the albumin gene. In any of the methods described herein, the α-Gal A protein expressed from the transgene can decrease the amount of glycospingolipids in the subject by at least 2-fold. The GLA transgene may further comprise additional elements, including, for example, a signal peptide and/or one or more control elements. Genetically modified cells (e.g., stem cells, precursor cells, liver cells, muscle cells, etc.) comprising an exogenous GLA transgene (integrated or extrachromosomal) are also provided, including cells made by the methods described herein. These cells can be used to provide an α-Gal A protein to a subject with Fabry's disease, for example by administering the cell(s) to a subject in need thereof or, alternatively, by isolating the α-Gal A protein produced by the cell and administering the protein to the subject in need thereof (enzyme replacement therapies). Also provided are vectors (e.g., viral vectors such as AAV or Ad or lipid nanoparticles) comprising a GLA transgene for use in any of the methods described herein, including for use in treatment of Fabry's.

In one aspect, the invention describes a method of expressing a transgene encoding one or more corrective GLA transgenes in a cell of the subject. The transgene may be inserted into the genome of a suitable target cell (e.g., blood cell, liver cell, brain cell, stem cell, precursor cell, etc.) such that the α-GalA product encoded by that corrective transgene is stably integrated into the genome of the cell (also referred to as a IVPRP® approach) or, alternatively, the transgene may be maintained in the cell extra-chromosomally (also referred to as a "cDNA" approach). In one embodiment, the corrective GLA transgene is introduced (stably or extra-chromosomally) into cells of a cell line for the in vitro production of the replacement protein, which (optionally purified and/or isolated) protein can then be administered to a subject for treating a subject with Fabry disease (e.g., by reducing and/or eliminating one or more symptoms associates with Fabry disease). In certain embodiments, the α-GalA product encoded by that corrective transgene increases α-GalA activity in a tissue a subject by any amount as compared to untreated subjects, for example, 2 to 1000 more (or any value therebetween) fold, including but not limited to 2 to 100 fold (or any value therebetween including 10, 20, 30, 40, 50, 60, 70, 80, 90, 100 fold), 100 to 500 fold (or any value therebetween), or 500 to 1000 fold or more.

In another aspect, described herein are ex vivo or in vivo methods of treating a subject with Fabry disease (e.g., by reducing and/or eliminating one or more symptoms associates with Fabry disease), the methods comprising inserting an GLA transgene into a cell as described herein (cDNA and/or IVPRP approaches) such that the protein is produced in a subject with Fabry disease. In certain embodiments, isolated cells comprising the GLA transgene can be used to treat a patient in need thereof, for example, by administering the cells to a subject with Fabry disease. In other embodiments, the corrective GLA transgene is inserted into a target tissue in the body such that the replacement protein is produced in vivo. In some preferred embodiments, the corrective transgene is inserted into the genome of cells in the target tissue, while in other preferred embodiments, the corrective transgene is inserted into the cells of the target tissue and is maintained in the cells extra-chromosomally. In any of the methods described herein, the expressed α-GalA protein may be excreted from the cell to act on or be taken up by secondary targets, including by other cells in other tissues (e.g. via exportation into the blood) that lack the GLA transgene (cross correction). In some instances, the primary and/or secondary target tissue is the liver. In other instances, the primary and/or secondary target tissue is the brain. In other instances, the primary and/or secondary target is blood (e.g., vasculature). In other instances, the primary and/or secondary target is skeletal muscle.

In certain embodiments, the methods and compositions described herein are used to decrease the amount of glycospingolipids including globotriaosylceramide (also known as GL-3 and Gb3) and globotriaosylsphingosine (lyso-Gb3), galabioasylceramide deposited in tissues of a subject suffering Fabry disease. In certain embodiments, the α-GalA product encoded by that corrective transgene decreases glycospingolipids in a tissue of a subject by any amount as compared to untreated subjects, for example, 2 to 100 more (or any value therebetween) fold, including but not limited to 2 to 100 fold (or any value therebetween including 10, 20, 30, 40, 50, 60, 70, 80, 90, 100 fold).

In any of the methods described herein, the corrective GLA transgene comprises the wild type sequence of the functioning GLA gene, while in other embodiments, the sequence of the corrective GLA transgene is altered in some manner to give enhanced biological activity (e.g., optimized codons to increase biological activity and/or alteration of transcriptional and translational regulatory sequences to improve gene expression). In some embodiments, the GLA gene is modified to improve expression characteristics. Such modifications can include, but are not limited to, insertion of a translation start site (e.g. methionine), addition of an optimized Kozak sequence, insertion of a signal peptide, and/or codon optimization. In some embodiments, the signal peptide can be chosen from an albumin signal peptide, a F.IX signal peptide, a IDS signal peptide and/or an α-GalA signal peptide. In any embodiments described herein, the GLA donor may comprise a donor as shown in any of FIGS. 1B, 1C, 10 and/or 13.

In any of the methods described herein, the GLA transgene may be inserted into the genome of a target cell using a nuclease. Non-limiting examples of suitable nucleases include zinc-finger nucleases (ZFNs), TALENs (Transcription activator like protein nucleases) and/or CRISPR/Cas nuclease systems, which include a DNA-binding molecule that binds to a target site in a region of interest (e.g., a disease associated gene, a highly-expressed gene, an albumin gene or other or safe harbor gene) in the genome of the cell and one or more nuclease domains (e.g., cleavage domain and/or cleavage half-domain). Cleavage domains and cleavage half domains can be obtained, for example, from various restriction endonucleases, Cas proteins and/or homing endonucleases. In certain embodiments, the zinc finger domain recognizes a target site in an albumin gene or a globin gene in red blood precursor cells (RBCs). See, e.g., U.S. Publication No. 2014001721, incorporated by reference in its entirety herein. In other embodiments, the nuclease (e.g., ZFN, TALEN, and/or CRISPR/Cas system) binds to and/or cleaves a safe-harbor gene, for example a CCR5 gene, a PPP1R12C (also known as AAVS1) gene, albumin, HPRT or a Rosa gene. See, e.g., U.S. Pat. Nos. 7,888,121; 7,972,854; 7,914,796; 7,951,925; 8,110,379; 8,409,861; 8,586,526; U.S. Patent Publications 20030232410; 20050208489; 20050026157; 20060063231; 20080159996; 201000218264; 20120017290; 20110265198; 20130137104; 20130122591; 20130177983; 20130177960 and 20140017212. The nucleases (or components thereof) may be provided as a polynucleotide encoding one or more nucleases (e.g., ZFN, TALEN, and/or CRISPR/Cas system) described herein. The polynucleotide may be, for example, mRNA. In some aspects, the mRNA may be chemically modified (See e.g. Kormann et al, (2011) *Nature Biotechnology* 29(2):154-157). In other aspects, the mRNA may comprise an ARCA cap (see U.S. Pat. Nos. 7,074,596 and 8,153,773). In further embodiments, the mRNA may comprise a mixture of unmodified and modified nucleotides (see U.S. Patent Publication 20120195936). In still further embodiments, the mRNA may comprise a WPRE element (see U.S. Patent Publication No. 20160326548).

In another aspect, the invention includes genetically modified cells (e.g., stem cells, precursor cells, liver cells, muscle cells, etc.) with the desired GLA transgene (optionally integrated using a nuclease). In some aspects, the edited stem or precursor cells are then expanded and may be induced to differentiate into a mature edited cells ex vivo, and then the cells are given to the patient. Thus, cells descended from the genetically edited (modified) GLA-producing stem or precursor cells as described herein may be selected for use in this invention. In other aspects, the edited precursors (e.g., CD34+ stem cells) are given in a bone marrow transplant which, following successful implantation, proliferate producing edited cells that then differentiate and mature in vivo and contain the biologic expressed from the GLA transgene. In some embodiments, the edited CD34+ stem cells are given to a patient intravenously such that the edited cells migrate to the bone marrow, differentiate and mature, producing the α-Gal A protein. In other aspects, the edited stem cells are muscle stem cells which are then introduced into muscle tissue. In some aspects, the engineered nuclease is a Zinc Finger Nuclease (ZFN) (the term "ZFN" includes a pair of ZFNs) and in others, the nuclease is a TALE nuclease (TALEN) (the term "TALENs" include a pair of TALENs), and in other aspects, a CRISPR/Cas system is used. The nucleases may be engineered to have specificity for a safe harbor locus, a gene associated with a disease, or for a gene that is highly expressed in cells. By way of non-limiting example only, the safe harbor locus may be the AAVS1 site, the CCR5 gene, albumin or the HPRT gene while the disease associated gene may be the GLA gene encoding α-galactosidase A.

In another aspect, described herein is a nuclease (e.g., ZFN, ZFN pair, TALEN, TALEN pair and/or CRISPR/Cas system) expression vector comprising a polynucleotide, encoding one or more nucleases as described herein, operably linked to a promoter. In one embodiment, the expression vector is a viral vector. In a further aspect, described herein is a GLA expression vector comprising a polynucleotide encoding α-GalA as described herein, operably linked to a promoter. In one embodiment, the expression is a viral vector.

In another aspect, described herein is a host cell comprising one or more nucleases (e.g., ZFN, ZFN pair, TALEN, TALEN pair and/or CRISPR/Cas system) expression vectors and/or an α-GalA expression vector as described herein. The host cell may be stably transformed or transiently transfected or a combination thereof with one or more nuclease expression vectors. In some embodiments, the host cell is a liver cell.

In other embodiments, methods are provided for replacing a genomic sequence in any target gene with a therapeutic GLA transgene as described herein, for example using a nuclease (e.g., ZFN, ZFN pair, TALEN, TALEN pair and/or CRISPR/Cas system) (or one or more vectors encoding said nuclease) as described herein and a "donor" sequence or GLA transgene that is inserted into the gene following targeted cleavage with the nuclease. The donor GLA sequence may be present in the vector carrying the nuclease (or component thereof), present in a separate vector (e.g., Ad, AAV or LV vector or mRNA) or, alternatively, may be introduced into the cell using a different nucleic acid delivery mechanism. Such insertion of a donor nucleotide sequence into the target locus (e.g., highly expressed gene, disease associated gene, other safe-harbor gene, etc.) results in the expression of the GLA transgene under control of the target locus's (e.g., albumin, globin, etc.) endogenous genetic control elements. In some aspects, insertion of the GLA transgene, for example into a target gene (e.g., albumin), results in expression of an intact α-GalA protein sequence and lacks any amino acids encoded by the target (e.g., albumin). In other aspects, the expressed exogenous α-GalA protein is a fusion protein and comprises amino acids encoded by the GLA transgene and by the endogenous locus into which the GLA transgene is inserted (e.g., from the endogenous target locus or, alternatively from sequences on the transgene that encode sequences of the target locus). The target may be any gene, for example, a safe harbor gene such as an albumin gene, an AAVS1 gene, an HPRT gene; a CCR5 gene; or a highly-expressed gene such as a globin gene in an RBC precursor cell (e.g., beta globin or gamma globin). In some instances, the endogenous sequences will be present on the amino (N)-terminal portion of the exogenous α-GalA protein, while in others, the endogenous sequences will be present on the carboxy (C)-terminal portion of the exogenous α-GalA protein. In other instances, endogenous sequences will be present on both the N- and C-terminal portions of the α-GalA exogenous protein. In some embodiments, the endogenous sequences encode a secretion signal peptide that is removed during the process of secretion of the α-GalA protein from the cell. The endogenous sequences may include full-length wild-type or mutant endogenous sequences or, alternatively, may include partial endogenous amino acid sequences. In some embodiments, the endogenous gene-transgene fusion is located at the endogenous locus within the cell while in other embodiments, the endogenous sequence-transgene coding sequence is inserted into another locus within a genome (e.g., a GLA-transgene sequence inserted into an albumin, HPRT or CCR5 locus). In some embodiments, the GLA transgene is expressed such that a therapeutic α-GalA protein product is retained within the cell (e.g., precursor or mature cell). In other embodiments, the GLA transgene is fused to the extracellular domain of a membrane protein such that upon expression, a transgene α-GalA fusion will result in the surface localization of the therapeutic protein. In some aspects, the extracellular domain is chosen from those proteins listed in Table 1. In some aspects, the edited cells further comprise a trans-membrane protein to traffic the cells to a particular tissue type. In one aspect, the trans-membrane protein comprises an antibody, while in others, the trans-membrane protein comprises a receptor. In certain embodiments, the cell is a precursor (e.g., CD34+ or hematopoietic stem cell) or mature RBC (descended from a genetically modified GAL-producing cell as described herein). In some aspects, the therapeutic α-GalA protein product encoded on the transgene is exported out of the cell to affect or be taken up by cells lacking the transgene. In certain embodiments, the cell is a liver cell which releases the therapeutic α-GalA protein into the blood stream to act on distal tissues (e.g., kidney, spleen, heart, brain, etc.).

The invention also supplies methods and compositions for the production of a cell (e.g., RBC) carrying an α-GalA therapeutic protein for treatment of Fabry disease that can be used universally for all patients as an allogenic product. This allows for the development of a single product for the treatment of patients with Fabry disease, for example. These carriers may comprise trans-membrane proteins to assist in the trafficking of the cell. In one aspect, the trans-membrane protein comprises an antibody, while in others, the trans-membrane protein comprises a receptor.

In one embodiment, the GLA transgene is expressed from the albumin promoter following insertion into the albumin locus. The biologic encoded by the GLA transgene then may be released into the blood stream if the transgene is inserted into a hepatocyte in vivo. In some aspects, the GLA transgene is delivered to the liver in vivo in a viral vector through intravenous administration. In some embodiments, the donor GLA transgene comprises a Kozak consensus sequence prior to the α-GalA coding sequence (Kozak (1987) *Nucl Acid Res* 15(20):8125-48), such that the expressed product lacks the albumin signal peptide. In some embodiments, the donor α-GalA transgene contains an alternate signal peptide, such as that from the Albumin, IDS or F9 genes, in place of the native GLA signal sequence. Thus, the donor may include a signal peptide as shown in any of SEQ ID NO:1 to 5 or a sequence exhibiting homology to these sequences that acts as a signal peptide (see e.g. FIGS. 1B, 10, 13 and 25).

In some embodiments, the GLA transgene donor is transfected or transduced into a cell for episomal or extra-chromosomal maintenance of the transgene. In some aspects, the GLA transgene donor is maintained on a vector comprising regulatory domains to regulate expression of the transgene donor. In some instances, the regulatory domains to regulate transgene expression are the domains endogenous to the transgene being expressed while in other instances, the regulatory domains are heterologous to the transgene. In some embodiments, the GLA transgene is maintained on a viral vector, while in others, it is maintained on a plasmid or mini circle. In some embodiments, the viral vector is an AAV, Ad or LV. In further aspects, the vector comprising the transgene donor is delivered to a suitable target cell in vivo, such that the α-GalA therapeutic protein encoded by the transgene donor is released into the blood stream when the transgene donor vector is delivered to a hepatocyte.

In another embodiment, the invention describes precursor cells (muscle stem cells, progenitor cells or CD34+ hematopoietic stem cell (HSPC) cells) into which the GLA transgene has been inserted such that mature cells derived from these precursors contain high levels of the α-GalA product encoded by the transgene. In some embodiments, these precursors are induced pluripotent stem cells (iPSC).

In some embodiments, the methods of the invention may be used in vivo in transgenic animal systems. In some aspects, the transgenic animal may be used in model development where the transgene encodes a human α-GalA protein. In some instances, the transgenic animal may be knocked out at the corresponding endogenous locus, allowing the development of an in vivo system where the human protein may be studied in isolation. Such transgenic models may be used for screening purposes to identify small molecules, or large biomolecules or other entities which may interact with or modify the human protein of interest. In some aspects, the GLA transgene is integrated into the selected locus (e.g., highly expressed or safe-harbor) into a stem cell (e.g., an embryonic stem cell, an induced pluripotent stem cell, a hepatic stem cell, a neural stem cell etc.) or non-human animal embryo obtained by any of the methods described herein and those standard in the art, and then the embryo is implanted such that a live animal is born. The animal is then raised to sexual maturity and allowed to produce offspring wherein at least some of the offspring comprise the integrated GLA transgene.

In a still further aspect, provided herein is a method for site specific integration of a nucleic acid sequence into an endogenous locus (e.g., disease-associated, highly expressed such as an albumin locus in a liver cell or globin locus in RBC precursor cells of a chromosome, for example into the chromosome of a non-human embryo. In certain embodiments, the method comprises: (a) injecting a non-human embryo with (i) at least one DNA vector, wherein the DNA vector comprises an upstream sequence and a downstream sequence flanking the α-GalA encoding nucleic acid sequence to be integrated, and (ii) at least one polynucleotide molecule encoding at least one nuclease (zinc finger, ZFN pair, TALE nuclease, TALEN pair or CRISPR/Cas system) that recognizes the site of integration in the target locus, and (b) culturing the embryo to allow expression of the nuclease (ZFN, TALEN, and/or CRISPR/Cas system, wherein a double stranded break introduced into the site of integration by the nuclease is repaired, via homologous recombination with the DNA vector, so as to integrate the nucleic acid sequence into the chromosome. In some embodiments, the polynucleotide encoding the nuclease is an RNA.

In any of the previous embodiments, the methods and compounds of the invention may be combined with other therapeutic agents for the treatment of subjects with Fabry disease. In some embodiments, the methods and compositions include the use of a molecular chaperone (Hartl et al (2011) *Nature* 465: 324-332) to insure the correct folding of the Fabry protein. In some aspects, the chaperone can be chosen from well-known chaperone proteins such as AT1001 (Benjamin et al (2012) *Mol Ther* 20(4):717-726), AT2220 (Khanna et al (2014) *PLoS ONE* 9(7): e102092, doi:10.1371), and Migalastat (Benjamin et al (2016) *Genet Med* doi: 10.1038/gim.2016.122). In some aspects, the methods and compositions are used in combination with methods and compositions to allow passage across the blood brain barrier. In other aspects, the methods and compositions are used in combination with compounds known to suppress the immune response of the subject.

A kit, comprising a nuclease system and/or a GLA donor as described herein is also provided. The kit may comprise nucleic acids encoding the one or more nucleases (ZFNs, ZFN pairs, TALENs, TALEN pairs and/or CRISPR/Cas system), (e.g. RNA molecules or the ZFN, TALEN, and/or CRISPR/Cas system encoding genes contained in a suitable expression vector), donor molecules, expression vectors encoding the single-guide RNA suitable host cell lines, instructions for performing the methods of the invention, and the like.

These and other aspects will be readily apparent to the skilled artisan in light of disclosure as a whole.

BRIEF DESCRIPTION OF THE DRAWINGS

FIG. 1A shows the reaction performed by α-GalA where in wild type mammals, the Gb3 substrate is broken down. In Fabry organisms, the Gb3 substrate builds up to toxic levels. FIG. 1B shows the initial viral vector used for expressing α-GalA from a cDNA, while FIG. 1C shows the initial viral vector used for expressing the α-GalA following nuclease-mediated insertion into the albumin gene.

FIG. 3A shows the activity in the HepG2/C3A cell media detected over a period of 6 days at varying doses of AAV virus comprising the cDNA expression cassette shown in FIG. 1B (bars from left to right show mock transfections, 10K, 30K, 100K, 300K, 1000K, 3000K and 9000K). FIG. 3B is a graph showing the activity detected in the cell pellets of the cells from FIG. 3A at the last time point of the experiment.

FIG. 4A shows the results for each individual mouse treated with 2.0e12 vector genomes per kilogram body weight (VG/kg) AAV2/6 comprising the cDNA construct while FIG. 4B shows the results for each mouse treated with 2.0e13 VG/kg AAV2/6-cDNA. In FIG. 4A, one mouse was additionally treated with the molecular chaperone DGJ on the day indicated. Also shown by a dotted line in both figures, is the levels of α-GalA activity found in wild type mice. As shown, the treated mice show levels above wild-type indicative of therapeutically beneficial levels.

FIG. 5A shows substrate levels detected in plasma and FIG. 5B shows substrate in heart tissue. FIG. 5C shows substrate detected in the liver and FIG. 5D depicts the substrate detected in the kidney tissues. In all tissues shown, the levels of Gb3 are lower than in the untreated GLAKO mice. Also indicated in FIG. 5D is the lowest level of quantitation (LLOQ) for this assay. The levels of Gb3 and lyso-Gb3 in the treated mice were also expressed in terms of the amount of substrate found relative to the untreated mice. FIG. 5E shows the percent of Gb3 remaining in specific tissues relative to untreated GLAKO mice and FIG. 5F shows the percent of lyso-Gb3 remaining in specific tissues relative to the untreated GLAKO mice. The tissue data sets in 5E and 5F are shown in each treatment group (untreated GLAKO), low and high dose treated GLAKO and wild type mice) where the bars represent the data from (left to right) plasma, liver, heart and kidney.

FIG. 6A depicts the α-Gal A activity detected in the plasma of GLAKO mice treated with the AAV2/8 virus comprising the transgene donor shown in FIG. 1C over time, where some mice received immunosuppression (see Example 4). Also shown is the level found in wild type mice. FIG. 6C shows the activity in animals that were additionally treated with low amounts of immunosuppression while FIG. 6D shows the activity in animals treated with moderate immunosuppression and FIG. 6E shows the animals treated with high levels of immunosuppression. Also shown in FIGS. 6C, 6D and 6E and the levels found in wild type mice for comparison (dotted line).

FIG. 7A shows the results for the animals treated with low levels of immunosuppression, where the arrows depict the timing of the chaperone dose and the mice treated. In FIG. 7A, all mice were treated with the chaperone and the results demonstrate that the activity increased. FIG. 7B shows the results for animals under moderate immunosuppression where two mice were treated with the DGJ. Those two mice saw an increase in the α-Gal A activity in their plasma. FIG. 7C depicts the results for the mice under the high dose of immunosuppression, and again indicates when the three mice were treated with the DGJ. These results demonstrate that the chaperone increased the amount of activity detected. The dotted line indicates activity levels found in wild type mice for comparison.

FIG. 9A shows the average activity numbers detected from the different treatment groups. FIG. 9B shows the amount of the Gb3 detected in plasma, liver and heart tissues for the various groups, and demonstrates that the cDNA approach results in a decrease of Gb3 approaching the wild type mice, indicating the protein expressed from the transgene is effective in acting on its target substrate. FIG. 9C is a graph showing the amount of α-GalA activity in individual mice from the table in 9A (ZFN+Donor+DGJ group not shown). The cDNA high dose mice (2.0e13 vg/kg cDNA donor vector) are shown with black circles on a black line. The cDNA low dose mice (2e12 vg/kg cDNA donor vector) are shown with shaded triangles on a dashed line. The wild type mice are shown as black open circles on a grey line and the GLAKO mice are shown with the black squares on the black line. Three of the four high dose cDNA mice had levels over 100 times that of the wild type mice.

FIG. 11B is a graph showing α-GalA activity comparing Variants #A, #K, #J, #H and #I (Variants A, K, J, H and I) at either a low (300,000/600,000 VG/cell ZFN/donor) or high (600,000/1,200,000 VG/cell ZFN/donor) dose of the ZFNs and GLA donors. 'Donor only' data set represents cells treated with only the donor construct without any ZFNs. Bars represent group averages with the standard deviations indicated with the error bars. The data indicated that Variant #K lead to the highest activity in this set.

FIG. 12 shows the data for each group to day 56 post injection, and also shows the data for the cDNA approach for comparison. At day 28, the mice treated with the "new" variant donors had a great deal more α-GalA activity than the initial donor. "Initial" donor refers to the donor used prior to optimization, see FIG. 10 and is shown in FIG. 12 as the black bar at the left of each grouping. cDNA results are presented only for day 56 at far right of the graph. Dotted line indicates 50-fold the activity level in wild type mice, indicating that all samples displayed at least 40-fold more activity than wild type at day 28.

FIG. 13A shows the layout of a cDNA expression system described previously (see U.S. Publication No. 20170119906) where a GLA coding sequence has been inserted using a different codon optimization protocol (DNA 2.0 v1 versus GeneArt v2, "GLAco v.2"). FIG. 13B shows the cDNA expression cassette used in this work with the alternate codon optimization protocol, and shows Variants #1 to #6 (also referred to as Variants 1 to 6) using signal peptides from the IDS, FIX or ALB genes in combination with GLA coding sequences optimized using the two different protocols.

FIG. 14B shows α-Gal A activity at day 5 for Variants #1, #2, #4, #5 and #6. For these studies, cells received 3.0 e5 VG/cell of the AAV2/6 GLA cDNA vectors. The bars represent group averages and error bars show the standard deviations.

FIG. 15A depicts plasmid α-Gal A activity in mice that were followed for 2 months with weekly or bi-weekly assessment. The left panel shows results of animals receiving the initial donor, variant A, variant E or variant B. The right panel shows results of wild-type animals or animals receiving variant E or J. FIG. 15B shows α-Gal A activity as measured in liver, heart, kidney and spleen assayed after the animals shown in FIG. 15A were sacrificed. The graph on the left of FIG. 15B shows data 2 months after treatment with the initial GLA donor construct ("Initial" shown in left-most bars of each group), after treatment with variant A (bars second from the left in each group), Variant B (middle bars for each group), Variant E (bars second from the right in each group) and in wild-type animals ("Wild type" shown in right-most bars in each group). The graph on the right of FIG. 15B depicts the activity for Variants E and J, where in each data set, activity in the untreated GLAKO mice are shown in the left most bar; in the wild type mice, bars second from the left in each group; activity in GLAKO mice treated with Variant #E are shown in bars third from left while activity for Variant J is shown in the right most bar. α-Gal A was many-fold above wild type in plasma and all measured tissues for GLA donor variants A, B, E and J. FIG. 15C depicts the level of plasma α-Gal A activity where the data for each mouse treated with the ZFN pair and the Variant A donor is shown. Note that this is the same experiment as shown in FIG. 15A, labeled Variant A, except that in FIG. 15A, the data for the mice as a group is shown, while in FIG. 15C, the data for each treated mouse is shown.

FIGS. 17A through 17C show the effect of treating the α-Gal A protein with the deglycosylation enzyme PNGaseF or Endo H. FIG. 17A shows Western blots made from homogenate derived from the mouse livers of the animals treated by the IVPRP approach. Three mice samples are shown in the top panel (labeled 'GLA donor Variant A') as well as a sample from a wild type mouse ('WT'), an untreated GLAKO mouse ('GLAKO') and a sample of recombinant human Gal A ('rec. hGal A'). In the lower panel, labeled 'GLA donor Variant J', two mice samples are shown along with a wild type mouse sample and an untreated GLAKO mouse sample, as well as a sample of recombinant human Gal A. (+) and (−) on both blots indicate treatment with PNGase F or Endo H. FIG. 17B shows a Western blot made as described in FIG. 17A except that the mice were treated using the cDNA approach ("initial" construct). FIG. 17C is a schematic depicting PNGaseF cleavage of complex glycosylation structures. The data demonstrates that the Gal A enzyme expressed in the treated GLAKO animals following either the IVPRP® or cDNA approaches shows similar deglycosylation as the deglycosylated human recombinant protein after PNGaseF treatment.

FIG. 18A depicts the plasma α-GalA activity in GLAKO mice treated with 2e12 VG/kg GLA cDNA comprising AAV2/6 as indicated. Activity was measured for up to 60 days post injection. FIG. 18B indicates the α-GalA activity in tissues as indicated in the mice from FIG. 18A. The data sets, from left to right, show the α-GalA activity in GLAKO untreated mice (left most bar); wild type mice (second to left most bar); GLAKO mice treated with the initial cDNA variant (third to left bar); and the GLAKO mice treated with cDNA variant D. Horizontal dotted lines indicate the activity corresponding to 10× the wild type level for reference. FIG. 18C depicts a Western blot detecting human α-GalA in the liver of 3 GLAKO mice treated with cDNA Variant #4. For comparison are shown activity a wild type mouse ("WT") and an untreated GLAKO mouse. For comparison purposes, also shown is the recombinant hGalA. The samples were treated with PNGasdF or EndoH as described in FIG. 17.

FIG. 20A shows the α-Gal A activity detected in the plasma following treatment of GLAKO mice with ZFNs specific for albumin and either the Variant E or Variant J donors (see FIG. 10). FIG. 20B shows the α-Gal A activity detected in various tissues of interest (liver, heart, kidney and spleen). In each dataset of FIG. 20B, from left to right, the bars show the results for GLAKO mice, wildtype (WT) mice, Variant E donor or Variant J donor.

FIG. 21A depicts the amount of GB3 detected as a percent of that detected in GLAKO mice (set at 100%). FIG. 21B depicts the amount of lyso-Gb3 detected as a percent of that detected in GLAKO mice (set at 100%). In both FIGS. 21A and 21B, each dataset, from left to right, shows the results detected in the plasma, liver, heart and kidney.

FIG. 23A depicts GalA activity in plasma from animals treated with the indicated constructs or untreated animals. FIG. 23B shows GalA activity in the indicated tissues (liver, spleen, heart and kidney) under the indicated conditions. The left most bar shows activity in untreated animals; the bar second from the left shows activity in animals treated with Donor Variant E only; the middle bar shows activity in wild-type animals; the bar second from the right shows activity in animals treated with ZFN and Donor Variant A; and the right-most bar shows activity in animals treated with ZFN and Donor Variant E. Untreated GLAKO mice, untreated wild type mice and GLAKO mice treated with donor but no ZFNs were included as controls. Stable plasma activity reached up to 80-fold wild type. Graphs display plasma α-Gal A activity over time and tissue activity at study termination (Day 56).

FIG. 24A shows Gb3 content and FIG. 24B shows lyso-Gb3 content as % reduction from untreated GLAKO mice in the indicated conditions. The bars under each condition show levels in plasma, liver, heart and kidney from left to right. Mice treated with ZFNs and either variant of the hGLA donor have greatly reduced substrate content.

FIG. 25A depicts variants L and M and shows that Variant M differs from Variant L in that it comprises an IDS signal peptide rather than a GLA signal peptide. Abbreviations are as described in FIG. 10. FIG. 25B shows integration of the GLA transgene into the Albumin locus. “TI” is a 5' Next Generation Sequencing (NGS) primer binding sequence added at 3' end of transgene followed by a targeted integration (TI)-specific sequence with same base composition as the wild type locus, allowing next generation sequencing to measure indels and HDR-mediated transgene integration simultaneously.

FIG. 26A shows results using the Variant L donor and FIG. 26B shows results using the Variant M donor.

FIG. 27A depicts GalA activity in plasma from animals treated with the indicated constructs or untreated animals. FIG. 27B shows GalA activity in the indicated tissues (liver, spleen, heart and kidney) under the indicated conditions. The left most bar shows activity in untreated animals; the bar second from the left shows activity in animals treated with Donor Variant M only; the middle bar shows activity in wild-type animals; the bar second from the right shows activity in animals treated with ZFN and Donor Variant M at a low dose; and the right-most bar shows activity in animals treated with ZFN and Donor Variant M at a high dose. As shown, stable plasma activity up to 250-fold wild type was observed and α-Gal A activity in heart and kidney was over 20-fold wild type and 4-fold wild type, respectively.

FIG. 28A shows activity in HepG2 cell supernatant and FIG. 28B shows activity in K562 cell pellets cultured in the presence of supernatant from treated or untreated HepG2 cells as shown in FIG. 28A.

FIG. 32A depicts the amount of GB3 detected as a percent of that detected in untreated GLAKO mice (set at 100%). FIG. 32B depicts the amount of lyso-Gb3 detected as a percent of that detected in untreated GLAKO mice (set at 100%). In both FIGS. 32A and 32B, each dataset, from left to right, shows the results detected in the plasma, liver, heart and kidney.

FIG. 33A depicts the amount of GB3 detected as a percent of that detected in untreated GLAKO mice (set at 100%). FIG. 33B depicts the amount of lyso-Gb3 detected as a percent of that detected in untreated GLAKO mice (set at 100%). In both FIGS. 33A and 33B, each dataset, from left to right, shows the results detected in the plasma, liver, heart and kidney.

DETAILED DESCRIPTION

Figure 1A:
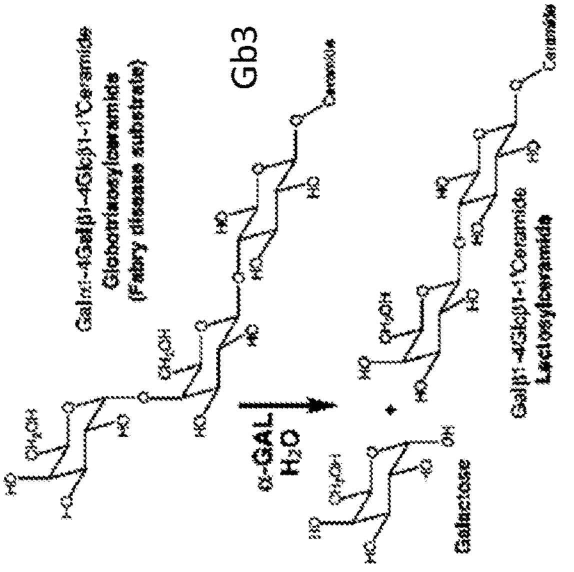
FIGS. 1A through 1C show the enzyme reaction performed by the wild type α-GalA enzyme and the initial donor and transgene expression cassettes.

Disclosed herein are methods and compositions for treating or preventing Fabry disease. The invention provides methods and compositions for insertion of a GLA transgene encoding a protein that is lacking or insufficiently expressed in the subject with Fabry disease such that the gene is expressed in the liver and the therapeutic (replacement) protein is expressed. The invention also describes the alteration of a cell (e.g., precursor or mature RBC, iPSC or liver cell) such that it produces high levels of the therapeutic and the introduction of a population of these altered cells into a patient will supply that needed protein. The transgene can encode a desired protein or structural RNA that is beneficial therapeutically in a patient in need thereof.

Thus, the methods and compositions of the invention can be used to express, from a transgene, one or more therapeutically beneficial α-GalA proteins from any locus (e.g., highly expressed albumin locus) to replace the enzyme that is defective and/or lacking in Fabry disease. Additionally, the invention provides methods and compositions for treatment (including the alleviation of one or more symptoms) of Fabry disease by insertion of the transgene sequences into highly-expressed loci in cells such as liver cells. Included in the invention are methods and compositions for delivery of the α-GalA encoding transgene via a viral vector to the liver of a subject in need thereof where the virus may be introduced via injection into the peripheral venus system or via direct injection into a liver-directed blood vessel (e.g. portal vein). The methods and compositions can be used to induce insertion of the transgene into a safe harbor locus (e.g. albumin) or can be used to cause extrachromosomal maintenance of a viral cDNA construct in a liver cell. In either case, the transgene is highly expressed and provides therapeutic benefit to the Fabry patient in need.

In addition, the transgene can be introduced into patient derived cells, e.g. patient derived induced pluripotent stem cells (iPSCs) or other types of stems cells (embryonic or hematopoietic) for use in eventual implantation. Particularly useful is the insertion of the therapeutic transgene into a hematopoietic stem cell for implantation into a patient in need thereof. As the stem cells differentiate into mature cells, they will contain high levels of the therapeutic protein for delivery to the tissues.

General

Practice of the methods, as well as preparation and use of the compositions disclosed herein employ, unless otherwise indicated, conventional techniques in molecular biology, biochemistry, chromatin structure and analysis, computational chemistry, cell culture, recombinant DNA and related fields as are within the skill of the art. These techniques are fully explained in the literature. See, for example, Sambrook et al. MOLECULAR CLONING: A LABORATORY MANUAL, Second edition, Cold Spring Harbor Laboratory Press, 1989 and Third edition, 2001; Ausubel et al., CURRENT PROTOCOLS IN MOLECULAR BIOLOGY, John Wiley & Sons, New York, 1987 and periodic updates; the series METHODS IN ENZYMOLOGY, Academic Press, San Diego; Wolffe, CHROMATIN STRUCTURE AND FUNCTION, Third edition, Academic Press, San Diego, 1998; METHODS IN ENZYMOLOGY, Vol. 304, "Chromatin" (P. M. Wassarman and A. P. Wolffe, eds.), Academic Press, San Diego, 1999; and METHODS IN MOLECULAR BIOLOGY, Vol. 119, "Chromatin Protocols" (P. B. Becker, ed.) Humana Press, Totowa, 1999.

Definitions

The terms "nucleic acid," "polynucleotide," and "oligonucleotide" are used interchangeably and refer to a deoxyribonucleotide or ribonucleotide polymer, in linear or circular conformation, and in either single- or double-stranded form. For the purposes of the present disclosure, these terms are not to be construed as limiting with respect to the length of a polymer. The terms can encompass known analogues of natural nucleotides, as well as nucleotides that are modified in the base, sugar and/or phosphate moieties (e.g., phosphorothioate backbones). In general, an analogue of a particular nucleotide has the same base-pairing specificity; i.e., an analogue of A will base-pair with T.

The terms "polypeptide," "peptide" and "protein" are used interchangeably to refer to a polymer of amino acid residues. The term also applies to amino acid polymers in which one or more amino acids are chemical analogues or modified derivatives of corresponding naturally-occurring amino acids.

"Binding" refers to a sequence-specific, non-covalent interaction between macromolecules (e.g., between a protein and a nucleic acid). Not all components of a binding interaction need be sequence-specific (e.g., contacts with phosphate residues in a DNA backbone), as long as the interaction as a whole is sequence-specific. Such interactions are generally characterized by a dissociation constant ($K_d$) of $10^{-6}$ $M^{-1}$ or lower. "Affinity" refers to the strength of binding: increased binding affinity being correlated with a lower $K_d$.

A "binding domain" is a molecule that is able to bind non-covalently to another molecule. A binding molecule can bind to, for example, a DNA molecule (a DNA-binding protein such as a zinc finger protein or TAL-effector domain protein or a single guide RNA), an RNA molecule (an RNA-binding protein) and/or a protein molecule (a protein-binding protein). In the case of a protein-binding molecule, it can bind to itself (to form homodimers, homotrimers, etc.) and/or it can bind to one or more molecules of a different protein or proteins. A binding molecule can have more than one type of binding activity. For example, zinc finger proteins have DNA-binding, RNA-binding and protein-binding activity. Thus, DNA-binding molecules, including DNA-binding components of artificial nucleases and transcription factors include but are not limited to, ZFPs, TALEs and sgRNAs.

A "zinc finger DNA binding protein" (or binding domain) is a protein, or a domain within a larger protein, that binds DNA in a sequence-specific manner through one or more zinc fingers, which are regions of amino acid sequence within the binding domain whose structure is stabilized through coordination of a zinc ion. The term zinc finger DNA binding protein is often abbreviated as zinc finger protein or ZFP. Artificial nucleases and transcription factors can include a ZFP DNA-binding domain and a functional domain (nuclease domain for a ZFN or transcriptional regulatory domain for ZFP-TF). The term "zinc finger nuclease" includes one ZFN as well as a pair of ZFNs that dimerize to cleave the target gene.

A "TALE DNA binding domain" or "TALE" is a polypeptide comprising one or more TALE repeat domains/units. The repeat domains are involved in binding of the TALE to its cognate target DNA sequence. A single "repeat unit" (also referred to as a "repeat") is typically 33-35 amino acids in length and exhibits at least some sequence homology with other TALE repeat sequences within a naturally occurring TALE protein. See, e.g., U.S. Pat. No. 8,586,526. Artificial nucleases and transcription factors can include a TALE DNA-binding domain and a functional domain (nuclease domain for a TALEN or transcriptional regulatory domain for TALEN-TF). The term "TALEN" includes one TALEN as well as a pair of TALENs that dimerize to cleave the target gene.

Zinc finger and TALE binding domains can be "engineered" to bind to a predetermined nucleotide sequence, for example via engineering (altering one or more amino acids) of the recognition helix region of a naturally occurring zinc finger or TALE protein. Therefore, engineered DNA binding proteins (zinc fingers or TALEs) are proteins that are non-naturally occurring. Non-limiting examples of methods for engineering DNA-binding proteins are design and selection. A designed DNA binding protein is a protein not occurring in nature whose design/composition results principally from rational criteria. Rational criteria for design include application of substitution rules and computerized algorithms for processing information in a database storing information of existing ZFP and/or TALE designs and binding data. See, for example, U.S. Pat. Nos. 8,568,526; 6,140,081; 6,453,242;

and 6,534,261; see also WO 98/53058; WO 98/53059; WO 98/53060; WO 02/016536 and WO 03/016496.

A "selected" zinc finger protein or TALE is a protein not found in nature whose production results primarily from an empirical process such as phage display, interaction trap or hybrid selection. See e.g., U.S. Pat. Nos. 8,586,526; 5,789,538; 5,925,523; 6,007,988; 6,013,453; 6,200,759; WO 95/19431; WO 96/06166; WO 98/53057; WO 98/54311; WO 00/27878; WO 01/60970; WO 01/88197; WO 02/099084.

"Recombination" refers to a process of exchange of genetic information between two polynucleotides. For the purposes of this disclosure, "homologous recombination (HR)" refers to the specialized form of such exchange that takes place, for example, during repair of double-strand breaks in cells via homology-directed repair mechanisms. This process requires nucleotide sequence homology, uses a "donor" molecule to template repair of a "target" molecule (i.e., the one that experienced the double-strand break), and is variously known as "non-crossover gene conversion" or "short tract gene conversion," because it leads to the transfer of genetic information from the donor to the target. Without wishing to be bound by any particular theory, such transfer can involve mismatch correction of heteroduplex DNA that forms between the broken target and the donor, and/or "synthesis-dependent strand annealing," in which the donor is used to re-synthesize genetic information that will become part of the target, and/or related processes. Such specialized HR often results in an alteration of the sequence of the target molecule such that part or all of the sequence of the donor polynucleotide is incorporated into the target polynucleotide.

In the methods of the disclosure, one or more targeted nucleases as described herein create a double-stranded break in the target sequence (e.g., cellular chromatin) at a predetermined site, and a "donor" polynucleotide, having homology to the nucleotide sequence in the region of the break, can be introduced into the cell. The presence of the double-stranded break has been shown to facilitate integration of the donor sequence. The donor sequence may be physically integrated or, alternatively, the donor polynucleotide is used as a template for repair of the break via homologous recombination, resulting in the introduction of all or part of the nucleotide sequence as in the donor into the cellular chromatin. Thus, a first sequence in cellular chromatin can be altered and, in certain embodiments, can be converted into a sequence present in a donor polynucleotide. Thus, the use of the terms "replace" or "replacement" can be understood to represent replacement of one nucleotide sequence by another, (i.e., replacement of a sequence in the informational sense), and does not necessarily require physical or chemical replacement of one polynucleotide by another.

In any of the methods described herein, additional pairs of zinc-finger or TALEN proteins can be used for additional double-stranded cleavage of additional target sites within the cell.

In certain embodiments of methods for targeted recombination and/or replacement and/or alteration of a sequence in a region of interest in cellular chromatin, a chromosomal sequence is altered by homologous recombination with an exogenous "donor" nucleotide sequence. Such homologous recombination is stimulated by the presence of a double-stranded break in cellular chromatin, if sequences homologous to the region of the break are present.

In any of the methods described herein, the first nucleotide sequence (the "donor sequence") can contain sequences that are homologous, but not identical, to genomic sequences in the region of interest, thereby stimulating homologous recombination to insert a non-identical sequence in the region of interest. Thus, in certain embodiments, portions of the donor sequence that are homologous to sequences in the region of interest exhibit between about 80 to 99% (or any integer there between) sequence identity to the genomic sequence that is replaced. In other embodiments, the homology between the donor and genomic sequence is higher than 99%, for example if only 1 nucleotide differs as between donor and genomic sequences of over 100 contiguous base pairs. In certain cases, a non-homologous portion of the donor sequence can contain sequences not present in the region of interest, such that new sequences are introduced into the region of interest. In these instances, the non-homologous sequence is generally flanked by sequences of 50-1,000 base pairs (or any integral value therebetween) or any number of base pairs greater than 1,000, that are homologous or identical to sequences in the region of interest. In other embodiments, the donor sequence is non-homologous to the first sequence, and is inserted into the genome by non-homologous recombination mechanisms.

Any of the methods described herein can be used for partial or complete inactivation of one or more target sequences in a cell by targeted integration of donor sequence that disrupts expression of the gene(s) of interest. Cell lines with partially or completely inactivated genes are also provided.

Furthermore, the methods of targeted integration as described herein can also be used to integrate one or more exogenous sequences. The exogenous nucleic acid sequence can comprise, for example, one or more genes or cDNA molecules, or any type of coding or non-coding sequence, as well as one or more control elements (e.g., promoters). In addition, the exogenous nucleic acid sequence may produce one or more RNA molecules (e.g., small hairpin RNAs (shRNAs), inhibitory RNAs (RNAis), microRNAs (miRNAs), etc.).

"Cleavage" refers to the breakage of the covalent backbone of a DNA molecule. Cleavage can be initiated by a variety of methods including, but not limited to, enzymatic or chemical hydrolysis of a phosphodiester bond. Both single-stranded cleavage and double-stranded cleavage are possible, and double-stranded cleavage can occur as a result of two distinct single-stranded cleavage events. DNA cleavage can result in the production of either blunt ends or staggered ends. In certain embodiments, fusion polypeptides are used for targeted double-stranded DNA cleavage.

A "cleavage half-domain" is a polypeptide sequence which, in conjunction with a second polypeptide (either identical or different) forms a complex having cleavage activity (preferably double-strand cleavage activity). The terms "first and second cleavage half-domains;" "+ and − cleavage half-domains" and "right and left cleavage half-domains" are used interchangeably to refer to pairs of cleavage half-domains that dimerize.

An "engineered cleavage half-domain" is a cleavage half-domain that has been modified so as to form obligate heterodimers with another cleavage half-domain (e.g., another engineered cleavage half-domain). See, U.S. Pat. Nos. 7,888,121; 7,914,796; 8,034,598 and 8,823,618, incorporated herein by reference in their entireties.

The term "sequence" refers to a nucleotide sequence of any length, which can be DNA or RNA; can be linear, circular or branched and can be either single-stranded or double stranded. The term "donor sequence" refers to a nucleotide sequence that is inserted into a genome. A donor sequence can be of any length, for example between 2 and 10,000 nucleotides in length (or any integer value therebetween or thereabove), preferably between about 100 and 1,000 nucleotides in length (or any integer therebetween), more preferably between about 200 and 500 nucleotides in length.

A "disease associated gene" is one that is defective in some manner in a monogenic disease. Non-limiting examples of monogenic diseases include severe combined immunodeficiency, cystic fibrosis, hemophilias, lysosomal storage diseases (e.g. Gaucher's, Hurler's, Hunter's, Fabry's, Neimann-Pick, Tay-Sach's etc.), sickle cell anemia, and thalassemia.

"Chromatin" is the nucleoprotein structure comprising the cellular genome. Cellular chromatin comprises nucleic acid, primarily DNA, and protein, including histones and non-histone chromosomal proteins. The majority of eukaryotic cellular chromatin exists in the form of nucleosomes, wherein a nucleosome core comprises approximately 150 base pairs of DNA associated with an octamer comprising two each of histones H2A, H2B, H3 and H4; and linker DNA (of variable length depending on the organism) extends between nucleosome cores. A molecule of histone H1 is generally associated with the linker DNA. For the purposes of the present disclosure, the term "chromatin" is meant to encompass all types of cellular nucleoprotein, both prokaryotic and eukaryotic. Cellular chromatin includes both chromosomal and episomal chromatin.

A "chromosome," is a chromatin complex comprising all or a portion of the genome of a cell. The genome of a cell is often characterized by its karyotype, which is the collection of all the chromosomes that comprise the genome of the cell. The genome of a cell can comprise one or more chromosomes.

An "episome" is a replicating nucleic acid, nucleoprotein complex or other structure comprising a nucleic acid that is not part of the chromosomal karyotype of a cell. Examples of episomes include plasmids and certain viral genomes.

A "target site" or "target sequence" is a nucleic acid sequence that defines a portion of a nucleic acid to which a binding molecule will bind, provided sufficient conditions for binding exist.

An "exogenous" molecule is a molecule that is not normally present in a cell, but can be introduced into a cell by one or more genetic, biochemical or other methods. "Normal presence in the cell" is determined with respect to the particular developmental stage and environmental conditions of the cell. Thus, for example, a molecule that is present only during embryonic development of muscle is an exogenous molecule with respect to an adult muscle cell. Similarly, a molecule induced by heat shock is an exogenous molecule with respect to a non-heat-shocked cell. An exogenous molecule can comprise, for example, a functioning version of a malfunctioning endogenous molecule or a malfunctioning version of a normally-functioning endogenous molecule.

An exogenous molecule can be, among other things, a small molecule, such as is generated by a combinatorial chemistry process, or a macromolecule such as a protein, nucleic acid, carbohydrate, lipid, glycoprotein, lipoprotein, polysaccharide, any modified derivative of the above molecules, or any complex comprising one or more of the above molecules. Nucleic acids include DNA and RNA, can be single- or double-stranded; can be linear, branched or circular; and can be of any length. Nucleic acids include those capable of forming duplexes, as well as triplex-forming nucleic acids. See, for example, U.S. Pat. Nos. 5,176,996 and 5,422,251. Proteins include, but are not limited to, DNA-binding proteins, transcription factors, chromatin remodeling factors, methylated DNA binding proteins, polymerases, methylases, demethylases, acetylases, deacetylases, kinases, phosphatases, integrases, recombinases, ligases, topoisomerases, gyrases and helicases.

An exogenous molecule can be the same type of molecule as an endogenous molecule, e.g., an exogenous protein or nucleic acid. For example, an exogenous nucleic acid can comprise an infecting viral genome, a plasmid or episome introduced into a cell, or a chromosome that is not normally present in the cell. Methods for the introduction of exogenous molecules into cells are known to those of skill in the art and include, but are not limited to, lipid-mediated transfer (i.e., liposomes, including neutral and cationic lipids), electroporation, direct injection, cell fusion, particle bombardment, calcium phosphate co-precipitation, DEAE-dextran-mediated transfer and viral vector-mediated transfer. An exogenous molecule can also be the same type of molecule as an endogenous molecule but derived from a different species than the cell is derived from. For example, a human nucleic acid sequence may be introduced into a cell line originally derived from a mouse or hamster.

By contrast, an "endogenous" molecule is one that is normally present in a particular cell at a particular developmental stage under particular environmental conditions. For example, an endogenous nucleic acid can comprise a chromosome, the genome of a mitochondrion, chloroplast or other organelle, or a naturally-occurring episomal nucleic acid. Additional endogenous molecules can include proteins, for example, transcription factors and enzymes.

A "fusion" molecule is a molecule in which two or more subunit molecules are linked, preferably covalently. The subunit molecules can be the same chemical type of molecule, or can be different chemical types of molecules. Examples of the first type of fusion molecule include, but are not limited to, fusion proteins (for example, a fusion between a ZFP or TALE DNA-binding domain and one or more activation domains) and fusion nucleic acids (for example, a nucleic acid encoding the fusion protein described supra). Examples of the second type of fusion molecule include, but are not limited to, a fusion between a triplex-forming nucleic acid and a polypeptide, and a fusion between a minor groove binder and a nucleic acid.

Expression of a fusion protein in a cell can result from delivery of the fusion protein to the cell or by delivery of a polynucleotide encoding the fusion protein to a cell, wherein the polynucleotide is transcribed, and the transcript is translated, to generate the fusion protein. Trans-splicing, polypeptide cleavage and polypeptide ligation can also be involved in expression of a protein in a cell. Methods for polynucleotide and polypeptide delivery to cells are presented elsewhere in this disclosure.

A "gene," for the purposes of the present disclosure, includes a DNA region encoding a gene product (see infra), as well as all DNA regions which regulate the production of the gene product, whether or not such regulatory sequences are adjacent to coding and/or transcribed sequences. Accordingly, a gene includes, but is not necessarily limited to, promoter sequences, terminators, translational regulatory sequences such as ribosome binding sites and internal ribosome entry sites, enhancers, silencers, insulators, boundary elements, replication origins, matrix attachment sites and locus control regions.

"Gene expression" refers to the conversion of the information, contained in a gene, into a gene product. A gene product can be the direct transcriptional product of a gene (e.g., mRNA, tRNA, rRNA, antisense RNA, ribozyme, structural RNA or any other type of RNA) or a protein produced by translation of an mRNA. Gene products also include RNAs which are modified, by processes such as capping, polyadenylation, methylation, and editing, and proteins modified by, for example, methylation, acetylation, phosphorylation, ubiquitination, ADP-ribosylation, myristilation, and glycosylation.

"Modulation" of gene expression refers to a change in the activity of a gene. Modulation of expression can include, but is not limited to, gene activation and gene repression. Genome editing (e.g., cleavage, alteration, inactivation, random mutation) can be used to modulate expression. Gene inactivation refers to any reduction in gene expression as compared to a cell that does not include a ZFP, TALE or CRISPR/Cas system as described herein. Thus, gene inactivation may be partial or complete.

A "region of interest" is any region of cellular chromatin, such as, for example, a gene or a non-coding sequence within or adjacent to a gene, in which it is desirable to bind an exogenous molecule. Binding can be for the purposes of targeted DNA cleavage and/or targeted recombination. A region of interest can be present in a chromosome, an episome, an organellar genome (e.g., mitochondrial, chloroplast), or an infecting viral genome, for example. A region of interest can be within the coding region of a gene, within transcribed non-coding regions such as, for example, leader sequences, trailer sequences or introns, or within non-transcribed regions, either upstream or downstream of the coding region. A region of interest can be as small as a single nucleotide pair or up to 2,000 nucleotide pairs in length, or any integral value of nucleotide pairs.

"Eukaryotic" cells include, but are not limited to, fungal cells (such as yeast), plant cells, animal cells, mammalian cells and human cells (e.g., liver cells, muscle cells, RBCs, T-cells, etc.), including stem cells (pluripotent and multipotent).

"Red Blood Cells" (RBCs) or erythrocytes are terminally differentiated cells derived from hematopoietic stem cells. They lack a nuclease and most cellular organelles. RBCs contain hemoglobin to carry oxygen from the lungs to the peripheral tissues. In fact, 33% of an individual RBC is hemoglobin. They also carry CO2 produced by cells during metabolism out of the tissues and back to the lungs for release during exhale. RBCs are produced in the bone marrow in response to blood hypoxia which is mediated by release of erythropoietin (EPO) by the kidney. EPO causes an increase in the number of proerythroblasts and shortens the time required for full RBC maturation. After approximately 120 days, since the RBC do not contain a nucleus or any other regenerative capabilities, the cells are removed from circulation by either the phagocytic activities of macrophages in the liver, spleen and lymph nodes (~90%) or by hemolysis in the plasma (~10%). Following macrophage engulfment, chemical components of the RBC are broken down within vacuoles of the macrophages due to the action of lysosomal enzymes. RBCs, in vitro or in vivo, can be descended from genetically modified stem or RBC precursor cells as described herein.

"Secretory tissues" are those tissues in an animal that secrete products out of the individual cell into a lumen of some type which are typically derived from epithelium. Examples of secretory tissues that are localized to the gastrointestinal tract include the cells that line the gut, the pancreas, and the gallbladder. Other secretory tissues include the liver, tissues associated with the eye and mucous membranes such as salivary glands, mammary glands, the prostate gland, the pituitary gland and other members of the endocrine system. Additionally, secretory tissues include individual cells of a tissue type which are capable of secretion.

The terms "operative linkage" and "operatively linked" (or "operably linked") are used interchangeably with reference to a juxtaposition of two or more components (such as sequence elements), in which the components are arranged such that both components function normally and allow the possibility that at least one of the components can mediate a function that is exerted upon at least one of the other components. By way of illustration, a transcriptional regulatory sequence, such as a promoter, is operatively linked to a coding sequence if the transcriptional regulatory sequence controls the level of transcription of the coding sequence in response to the presence or absence of one or more transcriptional regulatory factors. A transcriptional regulatory sequence is generally operatively linked in cis with a coding sequence, but need not be directly adjacent to it. For example, an enhancer is a transcriptional regulatory sequence that is operatively linked to a coding sequence, even though they are not contiguous.

With respect to fusion polypeptides, the term "operatively linked" can refer to the fact that each of the components performs the same function in linkage to the other component as it would if it were not so linked. For example, with respect to a fusion polypeptide in which a ZFP, TALE or Cas DNA-binding domain is fused to an activation domain, the ZFP or TALE DNA-binding domain and the activation domain are in operative linkage if, in the fusion polypeptide, the ZFP or TALE DNA-binding domain portion is able to bind its target site and/or its binding site, while the activation domain is able to up-regulate gene expression. When a fusion polypeptide in which a ZFP or TALE DNA-binding domain is fused to a cleavage domain, the ZFP or TALE DNA-binding domain and the cleavage domain are in operative linkage if, in the fusion polypeptide, the ZFP or TALE DNA-binding domain portion is able to bind its target site and/or its binding site, while the cleavage domain is able to cleave DNA in the vicinity of the target site.

A "functional fragment" of a protein, polypeptide or nucleic acid is a protein, polypeptide or nucleic acid whose sequence is not identical to the full-length protein, polypeptide or nucleic acid, yet retains the same function as the full-length protein, polypeptide or nucleic acid. A functional fragment can possess more, fewer, or the same number of residues as the corresponding native molecule, and/or can contain one or more amino acid or nucleotide substitutions. Methods for determining the function of a nucleic acid (e.g., coding function, ability to hybridize to another nucleic acid) are well-known in the art. Similarly, methods for determining protein function are well-known. For example, the DNA-binding function of a polypeptide can be determined, for example, by filter-binding, electrophoretic mobility-shift, or immunoprecipitation assays. DNA cleavage can be assayed by gel electrophoresis. See Ausubel et al., supra. The ability of a protein to interact with another protein can be determined, for example, by co-immunoprecipitation, two-hybrid assays or complementation, both genetic and biochemical. See, for example, Fields et al. (1989) *Nature* 340:245-246; U.S. Pat. No. 5,585,245 and PCT WO 98/44350.

A "vector" is capable of transferring gene sequences to target cells. Typically, "vector construct," "expression vector," and "gene transfer vector," mean any nucleic acid construct capable of directing the expression of a gene of interest and which can transfer gene sequences to target cells. Thus, the term includes cloning, and expression vehicles, as well as integrating vectors.

A "reporter gene" or "reporter sequence" refers to any sequence that produces a protein product that is easily measured, preferably although not necessarily in a routine assay. Suitable reporter genes include, but are not limited to, sequences encoding proteins that mediate antibiotic resistance (e.g., ampicillin resistance, neomycin resistance, G418 resistance, puromycin resistance), sequences encoding colored or fluorescent or luminescent proteins (e.g., green fluorescent protein, enhanced green fluorescent protein, red fluorescent protein, luciferase), and proteins which mediate enhanced cell growth and/or gene amplification (e.g., dihydrofolate reductase). Epitope tags include, for example, one or more copies of FLAG, His, myc, Tap, HA or any detectable amino acid sequence. "Expression tags" include sequences that encode reporters that may be operably linked to a desired gene sequence in order to monitor expression of the gene of interest.

The terms "subject" and "patient" are used interchangeably and refer to mammals such as human patients and non-human primates, as well as experimental animals such as rabbits, dogs, cats, rats, mice, and other animals. Accordingly, the term "subject" or "patient" as used herein means any mammalian patient or subject to which the altered cells of the invention and/or proteins produced by the altered cells of the invention can be administered. Subjects of the present invention include those having an LSD.

Nucleases

Any nuclease may be used in the practice of the present invention including but not limited to, at least one ZFNs, TALENs, homing endonucleases, and systems comprising CRISPR/Cas and/or Ttago guide RNAs, that are useful for in vivo cleavage of a donor molecule carrying a transgene and nucleases for cleavage of the genome of a cell such that the transgene is integrated into the genome in a targeted manner. Thus, described herein are compositions comprising one or more nucleases that cleave a selected gene, which cleavage results in genomic modification of the gene (e.g., insertions and/or deletions into the cleaved gene). In certain embodiments, one or more of the nucleases are naturally occurring. In other embodiments, one or more of the nucleases are non-naturally occurring, i.e., engineered in the DNA-binding molecule (also referred to as a DNA-binding domain) and/or cleavage domain. For example, the DNA-binding domain of a naturally-occurring nuclease may be altered to bind to a selected target site (e.g., a ZFP, TALE and/or sgRNA of CRISPR/Cas that is engineered to bind to a selected target site). In other embodiments, the nuclease comprises heterologous DNA-binding and cleavage domains (e.g., zinc finger nucleases; TAL-effector domain DNA binding proteins; meganuclease DNA-binding domains with heterologous cleavage domains). In other embodiments, the nuclease comprises a system such as the CRISPR/Cas of Ttago system.

A. DNA-Binding Domains

In certain embodiments, the composition and methods described herein employ a meganuclease (homing endonuclease) DNA-binding domain for binding to the donor molecule and/or binding to the region of interest in the genome of the cell. Naturally-occurring meganucleases recognize 15-40 base-pair cleavage sites and are commonly grouped into four families: the LAGLIDADG family, the GIY-YIG family, the His-Cyst box family and the HNH family. Exemplary homing endonucleases include I-SceI, I-CeuI, PI-PspI, PI-Sce, I-SceIV, I-CsmI, I-PanI, I-SceII, I-PpoI, I-SceIII, I-CreI, I-TevI, I-TevII and I-TevIII. Their recognition sequences are known. See also U.S. Pat. Nos. 5,420,032; 6,833,252; Belfort et al. (1997) *Nucleic Acids Res.* 25:3379-3388; Dujon et al. (1989) *Gene* 82:115-118; Perler et al. (1994) *Nucleic Acids Res.* 22, 1125-1127; Jasin (1996) *Trends Genet.* 12:224-228; Gimble et al. (1996) *J Mol. Biol.* 263:163-180; Argast et al. (1998) *J Mol. Biol.* 280:345-353 and the New England Biolabs catalogue. In addition, the DNA-binding specificity of homing endonucleases and meganucleases can be engineered to bind non-natural target sites. See, for example, Chevalier et al. (2002) *Molec. Cell* 10:895-905; Epinat et al. (2003) *Nucleic Acids Res.* 31:2952-2962; Ashworth et al. (2006) *Nature* 441:656-659; Paques et al. (2007) *Current Gene Therapy* 7:49-66; U.S. Patent Publication No. 20070117128. The DNA-binding domains of the homing endonucleases and meganucleases may be altered in the context of the nuclease as a whole (i.e., such that the nuclease includes the cognate cleavage domain) or may be fused to a heterologous cleavage domain.

In other embodiments, the DNA-binding domain of one or more of the nucleases used in the methods and compositions described herein comprises a naturally occurring or engineered (non-naturally occurring) TAL effector DNA binding domain. See, e.g., U.S. Pat. No. 8,586,526, incorporated by reference in its entirety herein. The plant pathogenic bacteria of the genus *Xanthomonas* are known to cause many diseases in important crop plants. Pathogenicity of *Xanthomonas* depends on a conserved type III secretion (T3 S) system which injects more than 25 different effector proteins into the plant cell. Among these injected proteins are transcription activator-like (TAL) effectors which mimic plant transcriptional activators and manipulate the plant transcriptome (see Kay et al (2007) *Science* 318:648-651). These proteins contain a DNA binding domain and a transcriptional activation domain. One of the most well characterized TAL-effectors is AvrBs3 from *Xanthomonas campestgris* pv. *Vesicatoria* (see Bonas et al (1989) *Mol Gen Genet* 218: 127-136 and WO2010079430). TAL-effectors contain a centralized domain of tandem repeats, each repeat containing approximately 34 amino acids, which are key to the DNA binding specificity of these proteins. In addition, they contain a nuclear localization sequence and an acidic transcriptional activation domain (for a review see Schornack S, et al (2006) *J Plant Physiol* 163(3): 256-272). In addition, in the phytopathogenic bacteria *Ralstonia solanacearum* two genes, designated brg11 and hpx17 have been found that are homologous to the AvrBs3 family of *Xanthomonas* in the *R. solanacearum* biovar 1 strain GMI1000 and in the biovar 4 strain RS1000 (See Heuer et al (2007) *Appl and Envir Micro* 73(13): 4379-4384). These genes are 98.9% identical in nucleotide sequence to each other but differ by a deletion of 1,575 bp in the repeat domain of hpx17. However, both gene products have less than 40% sequence identity with AvrBs3 family proteins of *Xanthomonas*. See, e.g., U.S. Pat. No. 8,586,526, incorporated by reference in its entirety herein.

Specificity of these TAL effectors depends on the sequences found in the tandem repeats. The repeated sequence comprises approximately 102 bp and the repeats are typically 91-100% homologous with each other (Bonas et al, ibid). Polymorphism of the repeats is usually located at positions 12 and 13 and there appears to be a one-to-one correspondence between the identity of the hypervariable diresidues (RVDs) at positions 12 and 13 with the identity of the contiguous nucleotides in the TAL-effector's target sequence (see Moscou and Bogdanove, (2009) *Science* 326:1501 and Boch et al (2009) *Science* 326:1509-1512). Experimentally, the natural code for DNA recognition of these TAL-effectors has been determined such that an HD sequence at positions 12 and 13 leads to a binding to cytosine (C), NG binds to T, NI to A, C, G or T, NN binds to A or G, and ING binds to T. These DNA binding repeats have been assembled into proteins with new combinations and numbers of repeats, to make artificial transcription factors that are able to interact with new sequences and activate the expression of a non-endogenous reporter gene in plant cells (Boch et al, ibid). Engineered TAL proteins have been linked to a FokI cleavage half domain to yield a TAL effector domain nuclease fusion (TALEN) exhibiting activity in a yeast reporter assay (plasmid based target). See, e.g., U.S. Pat. No. 8,586,526; Christian et al ((2010) *Genetics* epub 10.1534/genetics.110.120717).

In certain embodiments, the DNA binding domain of one or more of the nucleases used for in vivo cleavage and/or targeted cleavage of the genome of a cell comprises a zinc finger protein. Preferably, the zinc finger protein is non-naturally occurring in that it is engineered to bind to a target site of choice. See, for example, See, for example, Beerli et al. (2002) *Nature Biotechnol.* 20:135-141; Pabo et al. (2001) *Ann. Rev. Biochem.* 70:313-340; Isalan et al. (2001) Nature *Biotechnol.* 19:656-660; Segal et al. (2001) *Curr. Opin. Biotechnol.* 12:632-637; Choo et al. (2000) *Curr. Opin. Struct. Biol.* 10:411-416; U.S. Pat. Nos. 6,453,242; 6,534,261; 6,599,692; 6,503,717; 6,689,558; 7,030,215; 6,794,136; 7,067,317; 7,262,054; 7,070,934; 7,361,635; 7,253,273; and U.S. Patent Publication Nos. 2005/0064474; 2007/0218528; 2005/0267061, all incorporated herein by reference in their entireties.

An engineered zinc finger binding domain can have a novel binding specificity, compared to a naturally-occurring zinc finger protein. Engineering methods include, but are not limited to, rational design and various types of selection. Rational design includes, for example, using databases comprising triplet (or quadruplet) nucleotide sequences and individual zinc finger amino acid sequences, in which each triplet or quadruplet nucleotide sequence is associated with one or more amino acid sequences of zinc fingers which bind the particular triplet or quadruplet sequence. See, for example, co-owned U.S. Pat. Nos. 6,453,242 and 6,534,261, incorporated by reference herein in their entireties.

Exemplary selection methods, including phage display and two-hybrid systems, are disclosed in U.S. Pat. Nos. 5,789,538; 5,925,523; 6,007,988; 6,013,453; 6,410,248; 6,140,466; 6,200,759; and 6,242,568; as well as WO 98/37186; WO 98/53057; WO 00/27878; and WO 01/88197. In addition, enhancement of binding specificity for zinc finger binding domains has been described, for example, in co-owned WO 02/077227.

In addition, as disclosed in these and other references, zinc finger domains and/or multi-fingered zinc finger proteins may be linked together using any suitable linker sequences, including for example, linkers of 5 or more amino acids in length. See, also, U.S. Pat. Nos. 8,772,453; 6,479,626; 6,903,185; and 7,153,949 for exemplary linker sequences-. The proteins described herein may include any combination of suitable linkers between the individual zinc fingers of the protein.

Selection of target sites; ZFPs and methods for design and construction of fusion proteins (and polynucleotides encoding same) are known to those of skill in the art and described in detail in U.S. Pat. Nos. 6,140,081; 5,789,538; 6,453,242; 6,534,261; 5,925,523; 6,007,988; 6,013,453; 6,200,759; WO 95/19431; WO 96/06166; WO 98/53057; WO 98/54311; WO 00/27878; WO 01/60970; WO 01/88197; WO 02/099084; WO 98/53058; WO 98/53059; WO 98/53060; WO 02/016536 and WO 03/016496.

In addition, as disclosed in these and other references, zinc finger domains and/or multi-fingered zinc finger proteins may be linked together using any suitable linker sequences, including for example, linkers of 5 or more amino acids in length. See, also, U.S. Pat. Nos. 6,479,626; 6,903,185; and 7,153,949 for exemplary linker sequences 6 or more amino acids in length. The proteins described herein may include any combination of suitable linkers between the individual zinc fingers of the protein.

In certain embodiments, the DNA-binding domain is part of a CRISPR/Cas nuclease system, including, for example a single guide RNA (sgRNA). See, e.g., U.S. Pat. No. 8,697,359 and U.S. Patent Publication No. 20150056705. The CRISPR (clustered regularly interspaced short palindromic repeats) locus, which encodes RNA components of the system, and the Cas (CRISPR-associated) locus, which encodes proteins (Jansen et al., 2002. *Mol. Microbiol.* 43: 1565-1575; Makarova et al., 2002. *Nucleic Acids Res.* 30: 482-496; Makarova et al., 2006. *Biol. Direct* 1: 7; Haft et al., 2005. *PLoS Comput. Biol.* 1: e60) make up the gene sequences of the CRISPR/Cas nuclease system. CRISPR loci in microbial hosts contain a combination of CRISPR-associated (Cas) genes as well as non-coding RNA elements capable of programming the specificity of the CRISPR-mediated nucleic acid cleavage.

The Type II CRISPR is one of the most well characterized systems and carries out targeted DNA double-strand break in four sequential steps. First, two non-coding RNA, the pre-crRNA array and tracrRNA, are transcribed from the CRISPR locus. Second, tracrRNA hybridizes to the repeat regions of the pre-crRNA and mediates the processing of pre-crRNA into mature crRNAs containing individual spacer sequences. Third, the mature crRNA:tracrRNA complex directs Cas9 to the target DNA via Watson-Crick base-pairing between the spacer on the crRNA and the protospacer on the target DNA next to the protospacer adjacent motif (PAM), an additional requirement for target recognition. Finally, Cas9 mediates cleavage of target DNA to create a double-stranded break within the protospacer. Activity of the CRISPR/Cas system comprises of three steps: (i) insertion of alien DNA sequences into the CRISPR array to prevent future attacks, in a process called 'adaptation', (ii) expression of the relevant proteins, as well as expression and processing of the array, followed by (iii) RNA-mediated interference with the alien nucleic acid. Thus, in the bacterial cell, several of the so-called 'Cas' proteins are involved with the natural function of the CRISPR/Cas system and serve roles in functions such as insertion of the alien DNA etc.

In certain embodiments, Cas protein may be a "functional derivative" of a naturally occurring Cas protein. A "functional derivative" of a native sequence polypeptide is a compound having a qualitative biological property in common with a native sequence polypeptide. "Functional derivatives" include, but are not limited to, fragments of a native sequence and derivatives of a native sequence polypeptide and its fragments, provided that they have a biological activity in common with a corresponding native sequence polypeptide. A biological activity contemplated herein is the ability of the functional derivative to hydrolyze a DNA substrate into fragments. The term "derivative" encompasses both amino acid sequence variants of polypeptide, covalent modifications, and fusions thereof. Suitable derivatives of a Cas polypeptide or a fragment thereof include but are not limited to mutants, fusions, covalent modifications of Cas protein or a fragment thereof. Cas protein, which includes Cas protein or a fragment thereof, as well as derivatives of Cas protein or a fragment thereof, may be obtainable from a cell or synthesized chemically or by a combination of these two procedures. The cell may be a cell that naturally produces Cas protein, or a cell that naturally produces Cas protein and is genetically engineered to produce the endogenous Cas protein at a higher expression level or to produce a Cas protein from an exogenously introduced nucleic acid, which nucleic acid encodes a Cas that is same or different from the endogenous Cas. In some cases, the cell does not naturally produce Cas protein and is genetically engineered to produce a Cas protein. Additional non-limiting examples of RNA guided nucleases that may be used in addition to and/or instead of Cas proteins include Class 2 CRISPR proteins such as Cpf1. See, e.g., Zetsche et al. (2015) *Cell* 163:1-13.

The CRISPR-Cpf1 system, identified in *Francisella* spp, is a class 2 CRISPR-Cas system that mediates robust DNA interference in human cells. Although functionally conserved, Cpf1 and Cas9 differ in many aspects including in their guide RNAs and substrate specificity (see Fagerlund et al, (2015) *Genom Bio* 16:251). A major difference between Cas9 and Cpf1 proteins is that Cpf1 does not utilize tracrRNA, and thus requires only a crRNA. The FnCpf1 crRNAs are 42-44 nucleotides long (19-nucleotide repeat and 23-25-nucleotide spacer) and contain a single stem-loop, which tolerates sequence changes that retain secondary structure. In addition, the Cpf1 crRNAs are significantly shorter than the ~100-nucleotide engineered sgRNAs required by Cas9, and the PAM requirements for FnCpf1 are 5'-TTN-3' and 5'-CTA-3' on the displaced strand. Although both Cas9 and Cpf1 make double strand breaks in the target DNA, Cas9 uses its RuvC- and HNH-like domains to make blunt-ended cuts within the seed sequence of the guide RNA, whereas Cpf1 uses a RuvC-like domain to produce staggered cuts outside of the seed. Because Cpf1 makes staggered cuts away from the critical seed region, NHEJ will not disrupt the target site, therefore ensuring that Cpf1 can continue to cut the same site until the desired HDR recombination event has taken place. Thus, in the methods and compositions described herein, it is understood that the term '"Cas" includes both Cas9 and Cfp1 proteins. Thus, as used herein, a "CRISPR/Cas system" refers both CRISPR/Cas and/or CRISPR/Cfp1 systems, including both nuclease and/or transcription factor systems.

In some embodiments, the DNA binding domain is part of a TtAgo system (see Swarts et al, ibid; Sheng et al, ibid). In eukaryotes, gene silencing is mediated by the Argonaute (Ago) family of proteins. In this paradigm, Ago is bound to small (19-31 nt) RNAs. This protein-RNA silencing complex recognizes target RNAs via Watson-Crick base pairing between the small RNA and the target and endonucleolytically cleaves the target RNA (Vogel (2014) *Science* 344: 972-973). In contrast, prokaryotic Ago proteins bind to small single-stranded DNA fragments and likely function to detect and remove foreign (often viral) DNA (Yuan et al., (2005) *Mol. Cell* 19, 405; Olovnikov, et al. (2013) *Mol. Cell* 51, 594; Swarts et al., ibid). Exemplary prokaryotic Ago proteins include those from *Aquifex aeolicus, Rhodobacter sphaeroides*, and *Thermus thermophilus.*

One of the most well-characterized prokaryotic Ago protein is the one from *T. thermophilus* (TtAgo; Swarts et al. ibid). TtAgo associates with either 15 nt or 13-25 nt single-stranded DNA fragments with 5' phosphate groups. This "guide DNA" bound by TtAgo serves to direct the protein-DNA complex to bind a Watson-Crick complementary DNA sequence in a third-party molecule of DNA. Once the sequence information in these guide DNAs has allowed identification of the target DNA, the TtAgo-guide DNA complex cleaves the target DNA. Such a mechanism is also supported by the structure of the TtAgo-guide DNA complex while bound to its target DNA (G. Sheng et al., ibid). Ago from *Rhodobacter sphaeroides* (RsAgo) has similar properties (Olivnikov et al. ibid).

Exogenous guide DNAs of arbitrary DNA sequence can be loaded onto the TtAgo protein (Swarts et al. ibid.). Since the specificity of TtAgo cleavage is directed by the guide DNA, a TtAgo-DNA complex formed with an exogenous, investigator-specified guide DNA will therefore direct TtAgo target DNA cleavage to a complementary investigator-specified target DNA. In this way, one may create a targeted double-strand break in DNA. Use of the TtAgo-guide DNA system (or orthologous Ago-guide DNA systems from other organisms) allows for targeted cleavage of genomic DNA within cells. Such cleavage can be either single- or double-stranded. For cleavage of mammalian genomic DNA, it would be preferable to use of a version of TtAgo codon optimized for expression in mammalian cells. Further, it might be preferable to treat cells with a TtAgo-DNA complex formed in vitro where the TtAgo protein is fused to a cell-penetrating peptide. Further, it might be preferable to use a version of the TtAgo protein that has been altered via mutagenesis to have improved activity at 37 degrees Celsius. TtAgo-RNA-mediated DNA cleavage could be used to affect a panoply of outcomes including gene knock-out, targeted gene addition, gene correction, targeted gene deletion using techniques standard in the art for exploitation of DNA breaks.

Thus, the nuclease comprises a DNA-binding domain in that specifically binds to a target site in any gene into which it is desired to insert a donor (transgene).

B. Cleavage Domains

Any suitable cleavage domain can be operatively linked to a DNA-binding domain to form a nuclease. For example, ZFP DNA-binding domains have been fused to nuclease domains to create ZFNs—a functional entity that is able to recognize its intended nucleic acid target through its engineered (ZFP) DNA binding domain and cause the DNA to be cut near the ZFP binding site via the nuclease activity. See, e.g., Kim et al. (1996) *Proc Natl Acad Sci USA* 93(3):1156-1160. The term "ZFN" includes a pair of ZFNs that dimerize to cleave the target gene. More recently, ZFNs have been used for genome modification in a variety of organisms. See, for example, United States Patent Publications 20030232410; 20050208489; 20050026157; 20050064474; 20060188987; 20060063231; and International Publication WO 07/014275. Likewise, TALE DNA-binding domains have been fused to nuclease domains to create TALENs. See, e.g., U.S. Pat. No. 8,586,526. CRISPR/Cas nuclease systems comprising single guide RNAs (sgRNAs) that bind to DNA and associate with cleavage domains (e.g., Cas domains) to induce targeted cleavage have also been described. See, e.g., U.S. Pat. Nos. 8,697,359 and 8,932,814 and U.S. Patent Publication No. 20150056705.

As noted above, the cleavage domain may be heterologous to the DNA-binding domain, for example a zinc finger DNA-binding domain and a cleavage domain from a nuclease or a TALEN DNA-binding domain and a cleavage domain from a nuclease; a sgRNA DNA-binding domain and a cleavage domain from a nuclease (CRISPR/Cas); and/or meganuclease DNA-binding domain and cleavage domain from a different nuclease. Heterologous cleavage domains can be obtained from any endonuclease or exonuclease. Exemplary endonucleases from which a cleavage domain can be derived include, but are not limited to, restriction endonucleases and homing endonucleases. See, for example, 2002-2003 Catalogue, New England Biolabs, Beverly, MA; and Belfort et al. (1997) *Nucleic Acids Res.* 25:3379-3388. Additional enzymes which cleave DNA are known (e.g., 51 Nuclease; mung bean nuclease; pancreatic DNase I; micrococcal nuclease; yeast HO endonuclease; see also Linn et al. (eds.) *Nucleases*, Cold Spring Harbor Laboratory Press, 1993). One or more of these enzymes (or functional fragments thereof) can be used as a source of cleavage domains and cleavage half-domains.

Similarly, a cleavage half-domain can be derived from any nuclease or portion thereof, as set forth above, that requires dimerization for cleavage activity. In general, two fusion proteins are required for cleavage if the fusion proteins comprise cleavage half-domains. Alternatively, a single protein comprising two cleavage half-domains can be used. The two cleavage half-domains can be derived from the same endonuclease (or functional fragments thereof), or each cleavage half-domain can be derived from a different endonuclease (or functional fragments thereof). In addition, the target sites for the two fusion proteins are preferably disposed, with respect to each other, such that binding of the two fusion proteins to their respective target sites places the cleavage half-domains in a spatial orientation to each other that allows the cleavage half-domains to form a functional cleavage domain, e.g., by dimerizing. Thus, in certain embodiments, the near edges of the target sites are separated by 5-8 nucleotides or by 15-18 nucleotides. However, any integral number of nucleotides or nucleotide pairs can intervene between two target sites (e.g., from 2 to 50 nucleotide pairs or more). In general, the site of cleavage lies between the target sites.

Restriction endonucleases (restriction enzymes) are present in many species and are capable of sequence-specific binding to DNA (at a recognition site), and cleaving DNA at or near the site of binding. Certain restriction enzymes (e.g., Type IIS) cleave DNA at sites removed from the recognition site and have separable binding and cleavage domains. For example, the Type IIS enzyme Fok I catalyzes double-stranded cleavage of DNA, at 9 nucleotides from its recognition site on one strand and 13 nucleotides from its recognition site on the other. See, for example, U.S. Pat. Nos. 5,356,802; 5,436,150 and 5,487,994; as well as Li et al. (1992) *Proc. Natl. Acad. Sci. USA* 89:4275-4279; Li et al. (1993) *Proc. Natl. Acad. Sci. USA* 90:2764-2768; Kim et al. (1994a) *Proc. Natl. Acad. Sci. USA* 91:883-887; Kim et al. (1994b) *J. Biol. Chem.* 269:31,978-31,982. Thus, in one embodiment, fusion proteins comprise the cleavage domain (or cleavage half-domain) from at least one Type IIS restriction enzyme and one or more zinc finger binding domains, which may or may not be engineered.

An exemplary Type IIS restriction enzyme, whose cleavage domain is separable from the binding domain, is Fok I. This particular enzyme is active as a dimer. Bitinaite et al. (1998) *Proc. Natl. Acad. Sci. USA* 95: 10,570-10,575. Accordingly, for the purposes of the present disclosure, the portion of the Fok I enzyme used in the disclosed fusion proteins is considered a cleavage half-domain. Thus, for targeted double-stranded cleavage and/or targeted replacement of cellular sequences using zinc finger-Fok I fusions, two fusion proteins, each comprising a FokI cleavage half-domain, can be used to reconstitute a catalytically active cleavage domain. Alternatively, a single polypeptide molecule containing a zinc finger binding domain and two Fok I cleavage half-domains can also be used. Parameters for targeted cleavage and targeted sequence alteration using zinc finger-Fok I fusions are provided elsewhere in this disclosure.

A cleavage domain or cleavage half-domain can be any portion of a protein that retains cleavage activity, or that retains the ability to multimerize (e.g., dimerize) to form a functional cleavage domain.

Exemplary Type IIS restriction enzymes are described in U.S. Pat. No. 7,888,121, incorporated herein in its entirety. Additional restriction enzymes also contain separable binding and cleavage domains, and these are contemplated by the present disclosure. See, for example, Roberts et al. (2003) *Nucleic Acids Res.* 31:418-420.

In certain embodiments, the cleavage domain comprises one or more engineered cleavage half-domain (also referred to as dimerization domain mutants) that minimize or prevent homodimerization, as described, for example, in U.S. Pat. Nos. 8,772,453; 8,623,618; 8,409,861; 8,034,598; 7,914,796; and 7,888,121, the disclosures of all of which are incorporated by reference in their entireties herein. Amino acid residues at positions 446, 447, 479, 483, 484, 486, 487, 490, 491, 496, 498, 499, 500, 531, 534, 537, and 538 of FokI are all targets for influencing dimerization of the FokI cleavage half-domains.

Exemplary engineered cleavage half-domains of FokI that form obligate heterodimers include a pair in which a first cleavage half-domain includes mutations at amino acid residues at positions 490 and 538 of FokI and a second cleavage half-domain includes mutations at amino acid residues 486 and 499.

Thus, in one embodiment, a mutation at 490 replaces Glu (E) with Lys (K); the mutation at 538 replaces Iso (I) with Lys (K); the mutation at 486 replaced Gln (Q) with Glu (E); and the mutation at position 499 replaces Iso (I) with Lys (K). Specifically, the engineered cleavage half-domains described herein were prepared by mutating positions 490 (E→K) and 538 (I→K) in one cleavage half-domain to produce an engineered cleavage half-domain designated "E490K:1538K" ("KK") and by mutating positions 486 (Q→E) and 499 (I→L) in another cleavage half-domain to produce an engineered cleavage half-domain designated "Q486E:1499L", ("EL"). The engineered cleavage half-domains described herein are obligate heterodimer mutants in which aberrant cleavage is minimized or abolished. U.S. Pat. Nos. 7,914,796 and 8,034,598, the disclosures of which are incorporated by reference in their entireties. In certain embodiments, the engineered cleavage half-domain comprises mutations at positions 486, 499 and 496 (numbered relative to wild-type FokI), for instance mutations that replace the wild type Gln (Q) residue at position 486 with a Glu(E) residue, the wild type Iso (I) residue at position 499 with a Leu (L) residue and the wild-type Asn (N) residue at position 496 with an Asp (D) or Glu (E) residue (also referred to as a "ELD" and "ELE" domains, respectively). In other embodiments, the engineered cleavage half-domain comprises mutations at positions 490, 538 and 537 (numbered relative to wild-type FokI), for instance mutations that replace the wild type Glu (E) residue at position 490 with a Lys (K) residue, the wild type Iso (I) residue at position 538 with a Lys (K) residue, and the wild-type His (H) residue at position 537 with a Lys (K) residue or a Arg (R) residue (also referred to as "KKK" and "KKR" domains, respectively). In other embodiments, the engineered cleavage half-domain comprises mutations at positions 490 and 537 (numbered relative to wild-type FokI), for instance mutations that replace the wild type Glu (E) residue at position 490 with a Lys (K) residue and the wild-type His (H) residue at position 537 with a Lys (K) residue or a Arg (R) residue (also referred to as "KIK" and "KIR" domains, respectively). See, e.g., U.S. Pat. No. 8,772,453. In other embodiments, the engineered cleavage half domain comprises the "Sharkey" mutations (see Guo et al, (2010) *J Mol. Biol.* 400(1):96-107).

Engineered cleavage half-domains described herein can be prepared using any suitable method, for example, by site-directed mutagenesis of wild-type cleavage half-domains (Fok I) as described in U.S. Pat. Nos. 8,623,618; 8,409,861; 8,034,598; 7,914,796; and 7,888,121.

Methods and compositions are also used to increase the specificity of a nuclease pair for its intended target relative to other unintended cleavage sites, known as off-target sites (see U.S. Patent Publication No. US-2017-0218349-A1). Thus, nucleases described herein can comprise mutations in one or more of their DNA binding domain backbone regions and/or one or more mutations in their nuclease cleavage domains. These nucleases can include mutations to amino acid within the ZFP DNA binding domain ('ZFP backbone') that can interact non-specifically with phosphates on the DNA backbone, but they do not comprise changes in the DNA recognition helices. Thus, the invention includes mutations of cationic amino acid residues in the ZFP backbone that are not required for nucleotide target specificity. In some embodiments, these mutations in the ZFP backbone comprise mutating a cationic amino acid residue to a neutral or anionic amino acid residue. In some embodiments, these mutations in the ZFP backbone comprise mutating a polar amino acid residue to a neutral or non-polar amino acid residue. In preferred embodiments, mutations at made at position (−5), (−9) and/or position (−14) relative to the DNA binding helix. In some embodiments, a zinc finger may comprise one or more mutations at (−5), (−9) and/or (−14). In further embodiments, one or more zinc finger in a multi-finger zinc finger protein may comprise mutations in (−5), (−9) and/or (−14). In some embodiments, the amino acids at (−5), (−9) and/or (−14) (e.g. an arginine (R) or lysine (K)) are mutated to an alanine (A), leucine (L), Ser (S), Asp (N), Glu (E), Tyr (Y) and/or glutamine (Q).

In certain embodiments, the engineered cleavage half domains are derived from the FokI nuclease domain and comprise a mutation in one or more of amino acid residues 416, 422, 447, 448, and/or 525, numbered relative to the wild-type full length FokI. In some embodiments, the mutations in amino acid residues 416, 422, 447, 448, and/or 525 are introduced into the FokI "ELD", "ELE", "KKK", "KKR", "KK", "EL", "KIK", "KIR" and/or Sharkey as described above.

Further, described herein are methods to increase specificity of cleavage activity through independent titration of the engineered cleavage half-domain partners of a nuclease complex. In some embodiments, the ratio of the two partners (half cleavage domains) is given at a 1:2, 1:3, 1:4, 1:5, 1:6, 1:8, 1:9, 1:10 or 1:20 ratio, or any value therebetween. In other embodiments, the ratio of the two partners is greater than 1:30. In other embodiments, the two partners are deployed at a ratio that is chosen to be different from 1:1. When used individually or in combination, the methods and compositions of the invention provide surprising and unexpected increases in targeting specificity via reductions in off-target cleavage activity. The nucleases used in these embodiments may comprise ZFNs, a pair of ZFNs, TALENs, a pair of TALENs, CRISPR/Cas, CRISPR/dCas and TtAgo, or any combination thereof.

Alternatively, nucleases may be assembled in vivo at the nucleic acid target site using so-called "split-enzyme" technology (see, e.g. U.S. Patent Publication No. 20090068164). Components of such split enzymes may be expressed either on separate expression constructs, or can be linked in one open reading frame where the individual components are separated, for example, by a self-cleaving 2A peptide or IRES sequence. Components may be individual zinc finger binding domains or domains of a meganuclease nucleic acid binding domain.

Nucleases can be screened for activity prior to use, for example in a yeast-based chromosomal system as described in U.S. Pat. No. 8,563,314. Expression of the nuclease may be under the control of a constitutive promoter or an inducible promoter, for example the galactokinase promoter which is activated (de-repressed) in the presence of raffinose and/or galactose and repressed in presence of glucose.

The Cas9 related CRISPR/Cas system comprises two RNA non-coding components: tracrRNA and a pre-crRNA array containing nuclease guide sequences (spacers) interspaced by identical direct repeats (DRs). To use a CRISPR/Cas system to accomplish genome engineering, both functions of these RNAs must be present (see Cong et al, (2013) *Sciencexpress* 1/10.1126/science 1231143). In some embodiments, the tracrRNA and pre-crRNAs are supplied via separate expression constructs or as separate RNAs. In other embodiments, a chimeric RNA is constructed where an engineered mature crRNA (conferring target specificity) is fused to a tracrRNA (supplying interaction with the Cas9) to create a chimeric cr-RNA-tracrRNA hybrid (also termed a single guide RNA). (see Jinek ibid and Cong, ibid).

Target Sites

As described in detail above, DNA domains can be engineered to bind to any sequence of choice in a locus, for example an albumin or other safe-harbor gene. An engineered DNA-binding domain can have a novel binding specificity, compared to a naturally-occurring DNA-binding domain. Engineering methods include, but are not limited to, rational design and various types of selection. Rational design includes, for example, using databases comprising triplet (or quadruplet) nucleotide sequences and individual (e.g., zinc finger) amino acid sequences, in which each triplet or quadruplet nucleotide sequence is associated with one or more amino acid sequences of DNA binding domain which bind the particular triplet or quadruplet sequence. See, for example, co-owned U.S. Pat. Nos. 6,453,242 and 6,534,261, incorporated by reference herein in their entireties. Rational design of TAL-effector domains can also be performed. See, e.g., U.S. Publication No. 20110301073.

Exemplary selection methods applicable to DNA-binding domains, including phage display and two-hybrid systems, are disclosed in U.S. Pat. Nos. 5,789,538; 5,925,523; 6,007,988; 6,013,453; 6,410,248; 6,140,466; 6,200,759; and 6,242,568; as well as WO 98/37186; WO 98/53057; WO 00/27878; WO 01/88197 and GB 2,338,237.

Selection of target sites; nucleases and methods for design and construction of fusion proteins (and polynucleotides encoding same) are known to those of skill in the art and described in detail in U.S. Pat. Nos. 7,888,121 and 8,409,891, incorporated by reference in their entireties herein.

In addition, as disclosed in these and other references, DNA-binding domains (e.g., multi-fingered zinc finger proteins) may be linked together using any suitable linker sequences, including for example, linkers of 5 or more amino acids. See, e.g., U.S. Pat. Nos. 6,479,626; 6,903,185; and 7,153,949 for exemplary linker sequences 6 or more amino acids in length. The proteins described herein may include any combination of suitable linkers between the individual DNA-binding domains of the protein. See, also, U.S. Publication No. 20110301073.

Donors

As noted above, insertion of an exogenous sequence (also called a "donor sequence" or "donor"), for example for correction of a mutant gene or for increased expression of a gene encoding a protein lacking or deficient in Fabry disease (e.g., α-GalA) is provided. It will be readily apparent that the donor sequence is typically not identical to the genomic sequence where it is placed. A donor sequence can contain a non-homologous sequence flanked by two regions of homology ("homology arms") to allow for efficient HDR at the location of interest. Additionally, donor sequences can comprise a vector molecule containing sequences that are not homologous to the region of interest in cellular chromatin. A donor molecule can contain several, discontinuous regions of homology to cellular chromatin. For example, for targeted insertion of sequences not normally present in a region of interest, said sequences can be present in a donor nucleic acid molecule and flanked by regions of homology to sequence in the region of interest.

Described herein are methods of targeted insertion of a transgene encoding a α-GalA protein for insertion into a chosen location. The GLA transgene may encode a full-length α-GalA protein or may encode a truncated α-GalA protein. Polynucleotides for insertion can also be referred to as "exogenous" polynucleotides, "donor" polynucleotides or molecules or "transgenes." Non-limiting exemplary GLA donors are shown in FIGS. 1B, 1C, 10, 13, and 25.

The donor polynucleotide can be DNA or RNA, single-stranded and/or double-stranded and can be introduced into a cell in linear or circular form. See, e.g., U.S. Pat. Nos. 8,703,489 and 9,255,259. The donor sequence(s) can also be contained within a DNA MC, which may be introduced into the cell in circular or linear form. See, e.g., U.S. Patent Publication No. 20140335063. If introduced in linear form, the ends of the donor sequence can be protected (e.g., from exonucleolytic degradation) by methods known to those of skill in the art. For example, one or more dideoxynucleotide residues are added to the 3' terminus of a linear molecule and/or self-complementary oligonucleotides are ligated to one or both ends. See, for example, Chang et al. (1987) *Proc. Natl. Acad. Sci. USA* 84:4959-4963; Nehls et al. (1996) *Science* 272:886-889. Additional methods for protecting exogenous polynucleotides from degradation include, but are not limited to, addition of terminal amino group(s) and the use of modified internucleotide linkages such as, for example, phosphorothioates, phosphoramidates, and O-methyl ribose or deoxyribose residues.

A polynucleotide can be introduced into a cell as part of a viral or non-viral vector molecule having additional sequences such as, for example, replication origins, promoters and genes encoding antibiotic resistance. Moreover, donor polynucleotides can be introduced as naked nucleic acid, as nucleic acid complexed with an agent such as a liposome or poloxamer, or can be delivered by viruses (e.g., adenovirus, AAV, herpesvirus, retrovirus, lentivirus and integrase defective lentivirus (IDLV)).

The donor is generally inserted so that its expression is driven by the endogenous promoter at the integration site, namely the promoter that drives expression of the endogenous gene into which the donor is inserted (e.g., highly expressed, albumin, AAVS1, HPRT, etc.). However, it will be apparent that the donor may comprise a promoter and/or enhancer, for example a constitutive promoter or an inducible or tissue specific promoter. In some embodiments, the donor is maintained in the cell in an expression plasmid such that the gene is expressed extra-chromosomally.

The donor molecule may be inserted into an endogenous gene such that all, some or none of the endogenous gene is expressed. For example, a transgene as described herein may be inserted into an albumin or other locus such that some (N-terminal and/or C-terminal to the transgene encoding the lysosomal enzyme) or none of the endogenous albumin sequences are expressed, for example as a fusion with the transgene encoding the α-GalA protein(s). In other embodiments, the transgene (e.g., with or without additional coding sequences such as for albumin) is integrated into any endogenous locus, for example a safe-harbor locus.

When endogenous sequences (endogenous or part of the transgene) are expressed with the transgene, the endogenous sequences (e.g., albumin, etc.) may be full-length sequences (wild-type or mutant) or partial sequences. Preferably the endogenous sequences are functional. Non-limiting examples of the function of these full length or partial sequences (e.g., albumin) include increasing the serum half-life of the polypeptide expressed by the transgene (e.g., therapeutic gene) and/or acting as a carrier.

Furthermore, although not required for expression, exogenous sequences may also include transcriptional or translational regulatory sequences, for example, promoters, enhancers, insulators, internal ribosome entry sites, sequences encoding 2A peptides and/or polyadenylation signals.

Exogenous sequences linked to the transgene can also include signal peptides to assist in processing and/or secretion of the encoded protein. Non-limiting examples of these signal peptides include those from Albumin, IDS and Factor IX (see e.g. FIG. 13).

In certain embodiments, the exogenous sequence (donor) comprises a fusion of a protein of interest and, as its fusion partner, an extracellular domain of a membrane protein, causing the fusion protein to be located on the surface of the cell. This allows the protein encoded by the transgene to potentially act in the serum. In the case of Fabry disease, the α-GalA enzyme encoded by the transgene fusion acts on the metabolic products that are accumulating in the serum from its location on the surface of the cell (e.g., RBC). In addition, if the RBC is engulfed by a splenic macrophage as is the normal course of degradation, the lysosome formed when the macrophage engulfs the cell would expose the membrane bound fusion protein to the high concentrations of metabolic products in the lysosome at the pH more naturally favorable to that enzyme. Non-limiting examples of potential fusion partners are shown below in Table 1.

TABLE 1

Examples of potential fusion partners

| Name | Activity |
|---|---|
| Band 3 | Anion transporter, makes up to 25% of the RBC membrane surface protein |
| Aquaporin 1 | water transporter |
| Glut1 | glucose and L-dehydroascorbic acid transporter |
| Kidd antigen protein | urea transporter |
| RhAG | gas transporter |
| ATP1A1, ATP1B1 | Na+/K+ - ATPase |
| ATP2B1, ATP2B2, ATP2B3, ATP2B4 | Ca2+ - ATPase |
| NKCC1, NKCC2 | Na+ K+ 2Cl— - cotransporter |
| SLC12A3 | Na+—Cl— - cotransporter |

TABLE 1-continued

| Examples of potential fusion partners | |
|---|---|
| Name | Activity |
| SLC12A1, SLA12A2 | Na—K - cotransporter |
| KCC1 | K—Cl cotransporter |
| KCNN4 | Gardos Channel |

In some cases, the donor may be an endogenous gene (GLA) that has been modified. For instance, codon optimization may be performed on the endogenous gene to produce a donor. Furthermore, although antibody response to enzyme replacement therapy varies with respect to the specific therapeutic enzyme in question and with the individual patient, a significant immune response has been seen in many Fabry disease patients being treated with enzyme replacement with wild-type α-GalA. The transgene is considered to provide a therapeutic protein when it increases the amount of the protein (and/or its activity) as compared to subjects without the transgene. In addition, the relevance of these antibodies to the efficacy of treatment is also variable (see Katherine Ponder, (2008) *J Clin Invest* 118(8):2686). Thus, the methods and compositions of the current invention can comprise the generation of donor with modified sequences as compared to wild-type GLA, including, but not limited to, modifications that produce functionally silent amino acid changes at sites known to be priming epitopes for endogenous immune responses, and/or truncations such that the polypeptide produced by such a donor is less immunogenic.

Fabry disease patients often have neurological sequelae due the lack of the missing α-GalA enzyme in the brain. Unfortunately, it is often difficult to deliver therapeutics to the brain via the blood due to the impermeability of the blood brain barrier. Thus, the methods and compositions of the invention may be used in conjunction with methods to increase the delivery of the therapeutic into the brain, including but not limited to methods that cause a transient opening of the tight junctions between cells of the brain capillaries such as transient osmotic disruption through the use of an intracarotid administration of a hypertonic mannitol solution, the use of focused ultrasound and the administration of a bradykinin analogue (Matsukado et al (1996) *Neurosurgery* 39:125). Alternatively, therapeutics can be designed to utilize receptors or transport mechanisms for specific transport into the brain. Examples of specific receptors that may be used include the transferrin receptor, the insulin receptor or the low-density lipoprotein receptor related proteins 1 and 2 (LRP-1 and LRP-2). LRP is known to interact with a range of secreted proteins such as apoE, tPA, PAI-1 etc., and so fusing a recognition sequence from one of these proteins for LRP may facilitate transport of the enzyme into the brain, following expression in the liver of the therapeutic protein and secretion into the blood stream (see Gabathuler, (2010) ibid).

Cells

Also provided herein are genetically modified cells, for example, liver cells or stem cells comprising a transgene encoding a α-GalA protein, including cells produced by the methods described herein. The GLA transgene may be full-length or modified and can be expressed extra-chromosomally or can integrated in a targeted manner into the cell's genome using one or more nucleases. Unlike random integration, nuclease-mediated targeted integration ensures that the transgene is integrated into a specified gene. The transgene may be integrated anywhere in the target gene. In certain embodiments, the transgene is integrated at or near the nuclease binding and/or cleavage site, for example, within 1-300 (or any number of base pairs therebetween) base pairs upstream or downstream of the site of cleavage and/or binding site, more preferably within 1-100 base pairs (or any number of base pairs therebetween) of either side of the cleavage and/or binding site, even more preferably within 1 to 50 base pairs (or any number of base pairs therebetween) of either side of the cleavage and/or binding site. In certain embodiments, the integrated sequence does not include any vector sequences (e.g., viral vector sequences).

Any cell type can be genetically modified as described herein to comprise a transgene, including but not limited to cells or cell lines. Other non-limiting examples of genetically modified cells as described herein include T-cells (e.g., CD4+, CD3+, CD8+, etc.); dendritic cells; B-cells; autologous (e.g., patient-derived), muscle cells, brain cells and the like. In certain embodiments, the cells are liver cells and are modified in vivo. In certain embodiments, the cells are stem cells, including heterologous pluripotent, totipotent or multipotent stem cells (e.g., CD34+ cells, induced pluripotent stem cells (iPSCs), embryonic stem cells or the like). In certain embodiments, the cells as described herein are stem cells derived from patient.

The cells as described herein are useful in treating and/or preventing Fabry disease in a subject with the disorder, for example, by in vivo therapies. Ex vivo therapies are also provided, for example when the nuclease-modified cells can be expanded and then reintroduced into the patient using standard techniques. See, e.g., Tebas et al (2014) *New Eng J Med* 370(10):901. In the case of stem cells, after infusion into the subject, in vivo differentiation of these precursors into cells expressing the functional protein (from the inserted donor) also occurs.

Pharmaceutical compositions comprising the cells as described herein are also provided. In addition, the cells may be cryopreserved prior to administration to a patient.

Delivery

The nucleases, polynucleotides encoding these nucleases, donor polynucleotides and/or compositions (e.g., cells, proteins, polynucleotides, etc.) described herein may be delivered in vivo or ex vivo by any suitable means.

Methods of delivering nucleases as described herein are described, for example, in U.S. Pat. Nos. 6,453,242; 6,503,717; 6,534,261; 6,599,692; 6,607,882; 6,689,558; 6,824,978; 6,933,113; 6,979,539; 7,013,219; and 7,163,824, the disclosures of all of which are incorporated by reference herein in their entireties.

Nucleases and/or donor constructs as described herein may also be delivered using vectors containing sequences encoding one or more of the zinc finger, TALEN and/or Cas protein(s). Any vector systems may be used including, but not limited to, plasmid vectors, retroviral vectors, lentiviral vectors, adenovirus vectors, poxvirus vectors; herpesvirus vectors and adeno-associated virus vectors, etc. See, also, U.S. Pat. Nos. 6,534,261; 6,607,882; 6,824,978; 6,933,113; 6,979,539; 7,013,219; and 7,163,824, incorporated by reference herein in their entireties. Furthermore, it will be apparent that any of these vectors may comprise one or more of the sequences needed for treatment. Thus, when one or more nucleases and a donor construct are introduced into the cell, the nucleases and/or donor polynucleotide may be carried on the same vector or on different vectors. When multiple vectors are used, each vector may comprise a sequence encoding one or multiple nucleases and/or donor constructs.

Conventional viral and non-viral based gene transfer methods can be used to introduce nucleic acids encoding nucleases and donor constructs in cells (e.g., mammalian cells) and target tissues. Non-viral vector delivery systems include DNA plasmids, naked nucleic acid, and nucleic acid complexed with a delivery vehicle such as a liposome or poloxamer. Viral vector delivery systems include DNA and RNA viruses, which have either episomal or integrated genomes after delivery to the cell. For a review of gene therapy procedures, see Anderson, *Science* 256:808-813 (1992); Nabel & Felgner, *TIBTECH* 11:211-217 (1993); Mitani & Caskey, *TIBTECH* 11:162-166 (1993); Dillon, *TIBTECH* 11:167-175 (1993); Miller, *Nature* 357:455-460 (1992); Van Brunt, *Biotechnology* 6(10):1149-1154 (1988); Vigne, *Restorative Neurology and Neuroscience* 8:35-36 (1995); Kremer & Perricaudet, *British Medical Bulletin* 51(1):31-44 (1995); Haddada et al., in *Current Topics in Microbiology and Immunology* Doerfler and Bohm (eds.) (1995); and Yu et al., *Gene Therapy* 1:13-26 (1994).

Methods of non-viral delivery of nucleic acids include electroporation, lipofection, microinjection, biolistics, virosomes, liposomes, immunoliposomes, polycation or lipid: nucleic acid conjugates, naked DNA, artificial virions, and agent-enhanced uptake of DNA. Sonoporation using, e.g., the Sonitron 2000 system (Rich-Mar) can also be used for delivery of nucleic acids.

Additional exemplary nucleic acid delivery systems include those provided by Amaxa Biosystems (Cologne, Germany), Maxcyte, Inc. (Rockville, Maryland), BTX Molecular Delivery Systems (Holliston, MA) and Copernicus Therapeutics Inc, (see for example U.S. Pat. No. 6,008,336). Lipofection is described in e.g., U.S. Pat. Nos. 5,049,386; 4,946,787; and 4,897,355) and lipofection reagents are sold commercially (e.g., Transfectam™ and Lipofectin™). Cationic and neutral lipids that are suitable for efficient receptor-recognition lipofection of polynucleotides include those of Felgner, WO 91/17424, WO 91/16024.

The preparation of lipid:nucleic acid complexes, including targeted liposomes such as immunolipid complexes, is well known to one of skill in the art (see, e.g., Crystal, *Science* 270:404-410 (1995); Blaese et al., *Cancer Gene Ther.* 2:291-297 (1995); Behr et al., *Bioconjugate Chem.* 5:382-389 (1994); Remy et al., *Bioconjugate Chem.* 5:647-654 (1994); Gao et al., *Gene Therapy* 2:710-722 (1995); Ahmad et al., *Cancer Res.* 52:4817-4820 (1992); U.S. Pat. Nos. 4,186,183, 4,217,344, 4,235,871, 4,261,975, 4,485,054, 4,501,728, 4,774,085, 4,837,028, and 4,946,787).

The compositions described herein (cDNAs and/or nucleases) can also be delivered using nanoparticles, for example lipid nanoparticles (LNP). See, e.g., Lee et al (2016) *Am J Cancer Res* 6(5):1118-1134; U.S. Patent Publication No. 20170119904; and U.S. Provisional 62/559,186.

Additional methods of delivery include the use of packaging the nucleic acids to be delivered into EnGeneIC delivery vehicles (EDVs). These EDVs are specifically delivered to target tissues using bispecific antibodies where one arm of the antibody has specificity for the target tissue and the other has specificity for the EDV. The antibody brings the EDVs to the target cell surface and then the EDV is brought into the cell by endocytosis. Once in the cell, the contents are released (see MacDiarmid et al (2009) *Nature Biotechnology* 27(7):643).

The use of RNA or DNA viral based systems for the delivery of nucleic acids encoding engineered ZFPs take advantage of highly evolved processes for targeting a virus to specific cells in the body and trafficking the viral payload to the nucleus. Viral vectors can be administered directly to subjects (in vivo) or they can be used to treat cells in vitro and the modified cells are administered to subjects (ex vivo). Conventional viral based systems for the delivery of ZFPs include, but are not limited to, retroviral, lentivirus, adenoviral, adeno-associated, vaccinia and herpes simplex virus vectors for gene transfer. Integration in the host genome is possible with the retrovirus, lentivirus, and adeno-associated virus gene transfer methods, often resulting in long term expression of the inserted transgene. Additionally, high transduction efficiencies have been observed in many different cell types and target tissues.

The tropism of a retrovirus can be altered by incorporating foreign envelope proteins, expanding the potential target population of target cells. Lentiviral vectors are retroviral vectors that are able to transduce or infect non-dividing cells and typically produce high viral titers. Selection of a retroviral gene transfer system depends on the target tissue. Retroviral vectors are comprised of cis-acting long terminal repeats with packaging capacity for up to 6-10 kb of foreign sequence. The minimum cis-acting LTRs are sufficient for replication and packaging of the vectors, which are then used to integrate the therapeutic gene into the target cell to provide permanent transgene expression. Widely used retroviral vectors include those based upon murine leukemia virus (MuLV), gibbon ape leukemia virus (GaLV), Simian Immunodeficiency virus (SIV), human immunodeficiency virus (HIV), and combinations thereof (see, e.g., Buchscher et al., *J. Virol.* 66:2731-2739 (1992); Johann et al., *J. Virol.* 66:1635-1640 (1992); Sommerfelt et al., *Virol.* 176:58-59 (1990); Wilson et al., *J. Virol.* 63:2374-2378 (1989); Miller et al., *J. Virol.* 65:2220-2224 (1991)).

In applications in which transient expression is preferred, adenoviral based systems can be used. Adenoviral based vectors are capable of very high transduction efficiency in many cell types and do not require cell division. With such vectors, high titer and high levels of expression have been obtained. This vector can be produced in large quantities in a relatively simple system. Adeno-associated virus ("AAV") vectors are also used to transduce cells with target nucleic acids, e.g., in the in vitro production of nucleic acids and peptides, and for in vivo and ex vivo gene therapy procedures (see, e.g., West et al., *Virology* 160:38-47 (1987); U.S. Pat. No. 4,797,368; WO 93/24641; Kotin, Human Gene Therapy 5:793-801 (1994); Muzyczka, *J. Clin. Invest.* 94:1351 (1994). Construction of recombinant AAV vectors are described in a number of publications, including U.S. Pat. No. 5,173,414; Tratschin et al., *Mol. Cell. Biol.* 5:3251-3260 (1985); Tratschin, et al., *Mol. Cell. Biol.* 4:2072-2081 (1984); Hermonat & Muzyczka, *PNAS* 81:6466-6470 (1984); and Samulski et al., *J. Virol.* 63:03822-3828 (1989).

At least six viral vector approaches are currently available for gene transfer in clinical trials, which utilize approaches that involve complementation of defective vectors by genes inserted into helper cell lines to generate the transducing agent.

pLASN and MFG-S are examples of retroviral vectors that have been used in clinical trials (Dunbar et al., *Blood* 85:3048-305 (1995); Kohn et al., *Nat. Med.* 1:1017-102 (1995); Malech et al., *PNAS* 94:22 12133-12138 (1997)). PA317/pLASN was the first therapeutic vector used in a gene therapy trial. (Blaese et al., *Science* 270:475-480 (1995)). Transduction efficiencies of 50% or greater have been observed for MFG-S packaged vectors. (Ellem et al., *Immunol Immunother* 44(1):10-20 (1997); Dranoff et al., *Hum. Gene Ther.* 1:111-2 (1997).

Recombinant adeno-associated virus vectors (rAAV) are a promising alternative gene delivery systems based on the defective and nonpathogenic parvovirus adeno-associated type 2 virus. All vectors are derived from a plasmid that retains only the AAV 145 bp inverted terminal repeats flanking the transgene expression cassette. Efficient gene transfer and stable transgene delivery due to integration into the genomes of the transduced cell are key features for this vector system. (Wagner et al., *Lancet* 351:9117 1702-3 (1998), Kearns et al., *Gene Ther.* 9:748-55 (1996)). Other AAV serotypes, including by non-limiting example, AAV1, AAV3, AAV4, AAV5, AAV6, AAV8, AAV 8.2, AAV9, and AAV rh10 and pseudotyped AAV such as AAV2/8, AAV2/5 and AAV2/6 can also be used in accordance with the present invention.

Replication-deficient recombinant adenoviral vectors (Ad) can be produced at high titer and readily infect a number of different cell types. Most adenovirus vectors are engineered such that a transgene replaces the Ad Ela, E1b, and/or E3 genes; subsequently the replication defective vector is propagated in human 293 cells that supply deleted gene function in trans. Ad vectors can transduce multiple types of tissues in vivo, including non-dividing, differentiated cells such as those found in liver, kidney and muscle. Conventional Ad vectors have a large carrying capacity. An example of the use of an Ad vector in a clinical trial involved polynucleotide therapy for anti-tumor immunization with intramuscular injection (Sterman et al., *Hum. Gene Ther.* 7:1083-9 (1998)). Additional examples of the use of adenovirus vectors for gene transfer in clinical trials include Rosenecker et al., *Infection* 24:1 5-10 (1996); Sterman et al., *Hum. Gene Ther.* 9:7 1083-1089 (1998); Welsh et al., *Hum. Gene Ther.* 2:205-18 (1995); Alvarez et al., *Hum. Gene Ther.* 5:597-613 (1997); Topf et al., *Gene Ther.* 5:507-513 (1998); Sterman et al., *Hum. Gene Ther.* 7:1083-1089 (1998).

Packaging cells are used to form virus particles that are capable of infecting a host cell. Such cells include 293 cells, which package adenovirus, and ψ2 cells or PA317 cells, which package retrovirus. Viral vectors used in gene therapy are usually generated by a producer cell line that packages a nucleic acid vector into a viral particle. The vectors typically contain the minimal viral sequences required for packaging and subsequent integration into a host (if applicable), other viral sequences being replaced by an expression cassette encoding the protein to be expressed. The missing viral functions are supplied in trans by the packaging cell line. For example, AAV vectors used in gene therapy typically only possess inverted terminal repeat (ITR) sequences from the AAV genome which are required for packaging and integration into the host genome. Viral DNA is packaged in a cell line, which contains a helper plasmid encoding the other AAV genes, namely rep and cap, but lacking ITR sequences. The cell line is also infected with adenovirus as a helper. The helper virus promotes replication of the AAV vector and expression of AAV genes from the helper plasmid. The helper plasmid is not packaged in significant amounts due to a lack of ITR sequences. Contamination with adenovirus can be reduced by, e.g., heat treatment to which adenovirus is more sensitive than AAV.

In many gene therapy applications, it is desirable that the gene therapy vector be delivered with a high degree of specificity to a particular tissue type. Accordingly, a viral vector can be modified to have specificity for a given cell type by expressing a ligand as a fusion protein with a viral coat protein on the outer surface of the virus. The ligand is chosen to have affinity for a receptor known to be present on the cell type of interest. For example, Han et al., *Proc. Natl. Acad. Sci. USA* 92:9747-9751 (1995), reported that Moloney murine leukemia virus can be modified to express human heregulin fused to gp70, and the recombinant virus infects certain human breast cancer cells expressing human epidermal growth factor receptor. This principle can be extended to other virus-target cell pairs, in which the target cell expresses a receptor and the virus expresses a fusion protein comprising a ligand for the cell-surface receptor. For example, filamentous phage can be engineered to display antibody fragments (e.g., FAB or Fv) having specific binding affinity for virtually any chosen cellular receptor. Although the above description applies primarily to viral vectors, the same principles can be applied to nonviral vectors. Such vectors can be engineered to contain specific uptake sequences which favor uptake by specific target cells.

Gene therapy vectors can be delivered in vivo by administration to an individual patient, typically by systemic administration (e.g., intravenous, intraperitoneal, intramuscular, subdermal, or intracranial infusion) or topical application, as described below. Alternatively, vectors can be delivered to cells ex vivo, such as cells explanted from an individual patient (e.g., lymphocytes, bone marrow aspirates, tissue biopsy) or universal donor hematopoietic stem cells, followed by reimplantation of the cells into a patient, usually after selection for cells which have incorporated the vector.

Vectors (e.g., retroviruses, adenoviruses, liposomes, etc.) containing nucleases and/or donor constructs can also be administered directly to an organism for transduction of cells in vivo. Alternatively, naked DNA can be administered. Administration is by any of the routes normally used for introducing a molecule into ultimate contact with blood or tissue cells including, but not limited to, injection, infusion, topical application and electroporation. Suitable methods of administering such nucleic acids are available and well known to those of skill in the art, and, although more than one route can be used to administer a particular composition, a particular route can often provide a more immediate and more effective reaction than another route.

Vectors suitable for introduction of polynucleotides described herein include non-integrating lentivirus vectors (IDLV). See, for example, Ory et al. (1996) *Proc. Natl. Acad. Sci. USA* 93:11382-11388; Dull et al. (1998) *J. Virol.* 72:8463-8471; Zuffery et al. (1998) *J. Virol.* 72:9873-9880; Follenzi et al. (2000) *Nature Genetics* 25:217-222; U.S. Patent Publication No 2009/054985.

Pharmaceutically acceptable carriers are determined in part by the particular composition being administered, as well as by the particular method used to administer the composition. Accordingly, there is a wide variety of suitable formulations of pharmaceutical compositions available, as described below (see, e.g., *Remington's Pharmaceutical Sciences,* 17th ed., 1989).

It will be apparent that the nuclease-encoding sequences and donor constructs can be delivered using the same or different systems. For example, a donor polynucleotide can be carried by a plasmid, while the one or more nucleases can be carried by an AAV vector. Furthermore, the different vectors can be administered by the same or different routes (intramuscular injection, tail vein injection, other intravenous injection, intraperitoneal administration and/or intramuscular injection. The vectors can be delivered simultaneously or in any sequential order.

Formulations for both ex vivo and in vivo administrations include suspensions in liquid or emulsified liquids. The active ingredients often are mixed with excipients which are pharmaceutically acceptable and compatible with the active ingredient. Suitable excipients include, for example, water, saline, dextrose, glycerol, ethanol or the like, and combinations thereof. In addition, the composition may contain minor amounts of auxiliary substances, such as, wetting or emulsifying agents, pH buffering agents, stabilizing agents or other reagents that enhance the effectiveness of the pharmaceutical composition.

Applications

The methods of this invention contemplate the treatment and/or prevention of Fabry disease (e.g. lysosomal storage disease). Treatment can comprise insertion of the corrective disease associated GLA transgene in safe harbor locus (e.g. albumin) in a cell for expression of the needed enzyme and release into the blood stream. The corrective α-GalA encoding transgene may encode a wild type or modified protein; and/or may comprise a codon optimized GLA transgene; and/or a transgene in which epitopes may be removed without functionally altering the protein. In some cases, the methods comprise insertion of an episome expressing the α-GalA encoding transgene into a cell for expression of the needed enzyme and release into the blood stream. Insertion into a secretory cell, such as a liver cell for release of the product into the blood stream, is particularly useful. The methods and compositions of the invention also can be used in any circumstance wherein it is desired to supply a GLA transgene encoding one or more therapeutics in a hematopoietic stem cell such that mature cells (e.g., RBCs) derived from (descended from) these cells contain the therapeutic α-GalA protein. These stem cells can be differentiated in vitro or in vivo and may be derived from a universal donor type of cell which can be used for all patients. Additionally, the cells may contain a transmembrane protein to traffic the cells in the body. Treatment can also comprise use of patient cells containing the therapeutic transgene where the cells are developed ex vivo and then introduced back into the patient. For example, HSC containing a suitable α-GalA encoding transgene may be inserted into a patient via a bone marrow transplant. Alternatively, stem cells such as muscle stem cells or iPSC which have been edited using with the α-GalA encoding transgene maybe also injected into muscle tissue.

Thus, this technology may be of use in a condition where a patient is deficient in some protein due to problems (e.g., problems in expression level or problems with the protein expressed as sub- or non-functioning). Particularly useful with this invention is the expression of transgenes to correct or restore functionality in subjects with Fabry disease.

By way of non-limiting examples, different methods of production of a functional α-Gal A protein to replace the defective or missing α-Gal A protein is accomplished and used to treat Fabry disease. Nucleic acid donors encoding the proteins may be inserted into a safe harbor locus (e.g. albumin or HPRT) and expressed either using an exogenous promoter or using the promoter present at the safe harbor. Especially useful is the insertion of a GLA transgene in an albumin locus in a liver cell, where the GLA transgene further comprises sequences encoding a signal peptide that mediates the secretion of the expressed α-Gal A protein from the liver cell into the blood stream. Alternatively, donors can be used to correct the defective gene in situ. The desired α-GalA encoding transgene may be inserted into a CD34+ stem cell and returned to a patient during a bone marrow transplant. Finally, the nucleic acid donor maybe be inserted into a CD34+ stem cell at a beta globin locus such that the mature red blood cell derived from this cell has a high concentration of the biologic encoded by the nucleic acid donor. The biologic-containing RBC can then be targeted to the correct tissue via transmembrane proteins (e.g. receptor or antibody). Additionally, the RBCs may be sensitized ex vivo via electrosensitization to make them more susceptible to disruption following exposure to an energy source (see WO2002007752).

In some applications, an endogenous gene may be knocked out by use of the methods and compositions of the invention. Examples of this aspect include knocking out an aberrant gene regulator or an aberrant disease associated gene. In some applications, an aberrant endogenous gene may be replaced, either functionally or in situ, with a wild type version of the gene. The inserted gene may also be altered to improve the expression of the therapeutic α-GalA protein or to reduce its immunogenicity. In some applications, the inserted α-GalA encoding transgene is a fusion protein to increase its transport into a selected tissue such as the brain.

The following Examples relate to exemplary embodiments of the present disclosure in which the nuclease comprises a zinc finger nuclease (ZFN) (or a pair of ZFNs) or TALEN (or a pair of TALENs). It will be appreciated that this is for purposes of exemplification only and that other nucleases or nuclease systems can be used, for instance homing endonucleases (meganucleases) with engineered DNA-binding domains and/or fusions of naturally occurring of engineered homing endonucleases (meganucleases) DNA-binding domains and heterologous cleavage domains and/or a CRISPR/Cas system comprising an engineered single guide RNA. Similarly, it will be appreciated that suitable GLA donors are not limited to the ones exemplified below but include any GLA transgene.

EXAMPLES

Example 1: Design and Construction of α-GalA Encoding Transgenes

Two approaches were taken for the expression of the GLA transgenes. One approach, called In Vivo Protein Replacement Platform® ("IVPRP") utilizes engineered nucleases to insert the transgene at the albumin locus such that expression is driven by the albumin promoter (see, U.S. Pat. Nos. 9,394,545 and 9,150,847). The second approach involves transduction of a cell with an AAV comprising a cDNA copy of the transgene wherein the cDNA further comprises a promoter and other regulatory sequences. The GLA transgene expression cassette designs for these two approaches are illustrated in FIG. 1.

Example 2: Methods

HepG2/C3a and K562 Cell Transduction

HepG2 cells were transduced using standard techniques in both the cDNA and IVPRP® systems.

A. cDNA

The cDNA approach can include the use of an AAV delivered expression construct comprising an APOE enhancer linked to the hAAT promoter (Okuyama et al (1996) *Hum Gene Ther* 7(5):637-45), HBB-IGG intron (a chimeric intron composed of the 5'-donor site from the first intron of the human beta-globin gene and the branch and 3"-acceptor site from the intron of an immunoglobulin gene heavy chain variable region), a signal peptide, a coding sequence (wherein the coding sequence is optionally codon optimized) and a bovine growth hormone (bGH) poly A signal sequence.

For cDNA systems, HepG2 cells were transduced with AAV GLA cDNA vectors as described herein and the supernatant collected and tested for α-Gal A activity. In addition, K562 cells were cultured in the supernatant collected from the transduced HepG2 cells in the absence and presence of an excess of Mannose-6 Phosphate (M6P, 5 mM), which saturates the M6P receptors on the cell surface and blocks uptake of α-Gal A. The cell pellets were collected and tested for α-Gal A activity.

B. IVPRP®

There are three components to Fabry IVPRP®: two rAAV2/6 vectors that encode ZFNs SBS 47171 and SBS 47898, designed to cleave a specific locus in human Albumin intron 1, and one rAAV2/6 vector that encodes the hGLA donor template. The donor hGLA template is a codon optimized version of the hGLA cDNA flanked by homology arms to facilitate homology-directed repair (HDR) integration of the donor into human albumin.

HepG2/C3A cells (also referred to as "HepG2" cells) (ATCC, CRL 10741) were maintained in Minimum Essential Medium (MEM) with Earle's Salts and L glutamine (Corning,) with 10% Fetal Bovine Serum (FBS) (Life Technologies) and 1× Penicillin Streptomycin Glutamine (Life Technologies) and incubated at 37° C. and 5% CO2. Cells were passaged every 3 4 days.

For IVPRP® transduction, cells were rinsed and trypsinized with 0.25% Trypsin/2.21 mM EDTA (Corning) and re suspended in growth media. A small aliquot was mixed 1:1 with trypan blue solution 0.4% (w/v) in phosphate buffered saline (PBS; Corning) and counted on the TC20 Automated Cell Counter (Bio Rad). The cells were re suspended at a density of 2e5 per mL in growth media and seeded into a 24 well plate (Corning) at 1e5 in 0.5 mL media per well. Recombinant AAV2/6 particles were mixed at the appropriate multiplicity of infection (MOI) with growth media and added to the cells.

HepG2 cells were transduced with either hGLA donor only (in duplicate; control) or with the two hALB ZFNs SB 47171 and SB 47931 plus the SB IDS donor (in triplicate). The MOI for the donor only transduction was 6e5 vector genomes (vg)/cell. The MOI for the ZFN+Donor transduction was 3e5 vg/cell for each ZFN and 6e5 vg/cell for the hGLA Donor. This represents a ZFN1:ZFN2:Donor ratio of 1:1:2, which has been previously determined to be the optimal ratio for in vitro experiments. The hGLA donor was added 24 hours after the ZFN vectors to maximize the transduction efficiency in vitro.

Following transduction, cells were left in culture for 6-10 days. Supernatant was collected on Days 3, 5, 7 and 10 (where applicable) and replaced with fresh media. After the final supernatant collection step, cells were trypsinized and resuspended as described above, then centrifuged to create a cell pellet, washed with PBS, and stored at −80 C.

A similar method was used to transduce HepG2 cells with GLA cDNA constructs. The MOI for the GLA cDNA constructs was either 3e4, 1e5, 3e5 or 1e6 vg/cell.

α-GalA Activity Assay

α-GalA activity was assessed in a fluorometric assay using the synthetic substrate 4-methylumbelliferyl-α-D-galactopyranoside (4MU-α-Gal, Sigma).

Briefly, 10 microliters of HepG2 cell culture supernatant were mixed with 40 μL of 5 mM 4MU-α-Gal dissolved in phosphate buffer (0.1 M citrate/0.2 M phosphate buffer, pH 4.6, 1% Triton X-100). Reactions were incubated at 37° C. and terminated by addition of 100 μL of 0.5 M glycine buffer, pH 10.3. The release of 4 methylumbelliferone (4 MU) was determined by measurement of fluorescence (Ex365/Em450) using a SpectraMax Gemini XS fluorescent reader (Molecular Devices, Sunnyvale CA).

A standard curve was generated using serial 2 fold dilutions of 4 MU. The resulting data were fitted with a log curve; concentration of 4 MU in test samples was calculated using this best fit curve. Enzymatic activity is expressed as nmol 4 MU released per hour of assay incubation time, per mL of cell culture supernatant (nmol/hr/mL).

Detection of Gb3

Gb3 and Lyso-Gb3 Substrate Quantitation and Analysis:

Fabry substrate globotriaosylceramide (Gb3) was measured in selected murine plasma and tissues via mass spectrometry. Briefly, tissues were weighed and mechanically disrupted in tissue destruction fluid (5% MeOH, 95% water and 0.1% ascetic acid) at a ratio of 5 ml fluid per mg of tissue. 10 μl of plasma or tissue slurry were then added to 90 μl of precipitation solvent (MeOH with internal standard N-Tricosanoyl ceramide trihexoside (C23:0, Matreya) spiked into solution) in a siliconized tube, vortexed and placed on a shaking plate at room temp for 30 minutes. Samples were then centrifuged and 10 μl of sample added to 90 μl of single blank matrix (DMSO/MeOH 1:1+0.1% FA) in glass LC-MS vial. Samples were analyzed for Gb3 chain length 24:0, the predominant Gb3 species present in GLAKO mice and measured against a standard curve composed of ceramide trihexoside (Gb3, Matreya).

Globotriaosylsphingosine (lyso-Gb3) was measured in a similar manner using Glucosylsphingosine (Matreya) as the internal standard and lyso-Ceramide trihexoside (lyso-Gb3, Matreya) to create the standard curve.

Assessment of Gene Modification (% Indels)

The ZFN target site was subjected to sequence analysis using the MiSeq system (Illumina, San Diego CA). A pair of oligonucleotide primers were designed for amplification of a 194 bp fragment spanning the ZFN target site in the human albumin locus or mouse albumin locus, and to introduce binding sequences for a second round of amplification. The products of this PCR amplification were purified, and subjected to a second round of PCR with oligonucleotides designed to introduce an amplicon specific identifier sequence ("barcode"), as well as terminal regions designed for binding sequencing oligonucleotide primers. The mixed population of bar coded amplicons was then subjected to MiSeq analysis, a solid phase sequencing procedure that allows the parallel analysis of thousands of samples on a single assay chip.

In Vivo Testing of Fabry IVPRP® and cDNA Vectors in a GLAKO Mouse Model

To demonstrate the efficacy of these therapeutics in an animal model of Fabry disease, GLAKO mice were transduced with the same AAV2/6 GLA cDNA construct used in HepG2 cells. Other GLAKO mice were transduced with the mouse version of Fabry IVPRP, which consists of two rAAV2/8 vectors that encode ZFNs SB-48641 and SB-31523, designed for cleaving mouse Albumin, and one rAAV2/8 vector that encodes the hGLA cDNA donor template with mouse homology arms. As controls, additional GLAKO mice and wild type mice were injected with AAV vector formulation buffer (PBS, 35 nM NaCl, 1% sucrose, 0.05% pluronic) F-68, pH 7.1) containing no vector particles. Animals received 50 mg/kg cyclophosphamide every two weeks, starting on the day prior to AAV injection. All mice were 4-12 weeks old at the time of injection. Mice were monitored for 2-3 months, with plasma drawn weekly or bi-weekly via submandibular puncture to measure plasma α-GalA activity. Mice were euthanized at the end of the experiment and α-GalA activity was measured in plasma, liver, kidney, heart and spleen as described above. Gb3 and lyso-Gb3 substrate levels were measured in plasma, liver, kidney, heart and spleen via mass spectrometry. For mice treated with Fabry IVPRP, indels in liver tissue were measured via MiSeq as described above.

Western Blot and Deglycosylation Procedures:

Mouse livers were homogenized in 0.1 M citrate/0.2 M phosphate buffer, pH 4.6. Liver homogenates were boiled for 10 minutes, then aliquots of each sample were deglycosylated by treating with PNGase F (New England Biolabs, NEB) for 1 hour according to the NEB protocol.

1 ug total protein was loaded onto a NuPage 4-12% Bis-Tris Midi Gel (Invitrogen). 0.5 ng of recombinant human GLA loaded (R&D Systems) before and after PNGase F treatment was included as a size reference.

The antibodies used for the Western blot were: Primary antibody: α-GLA, Sino Biological rabbit monoclonal antibody, 1:1000; Secondary antibody: goat α-rabbit IgG-HRP, Thermo Fisher, 1:10,000.

Example 3: Expression of the GLA Transgene In Vitro

IVPRP® Approach: Methods are described above in Example 2. In brief, HepG2/C3a cells were transduced with AAV2/6 ZFNs and hGLA donor vectors at a dose of 100k vg/cell for each ZFN and 200k vg/cell for the GLA donor or a dose of 300k/600k for ZFNs and donor, respectively.

Figure 1B:
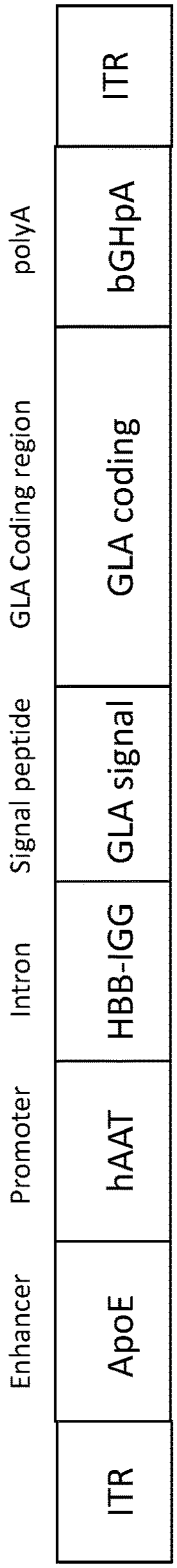
Figure 1C:
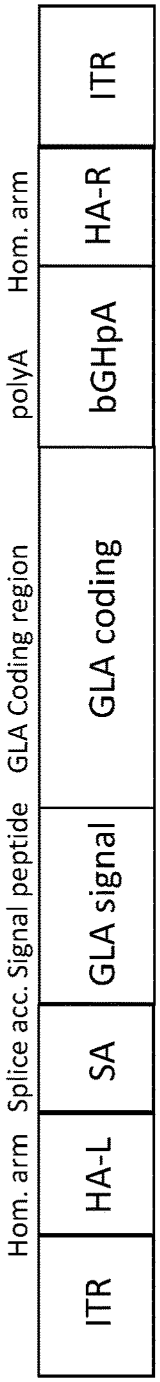
Figure 2:
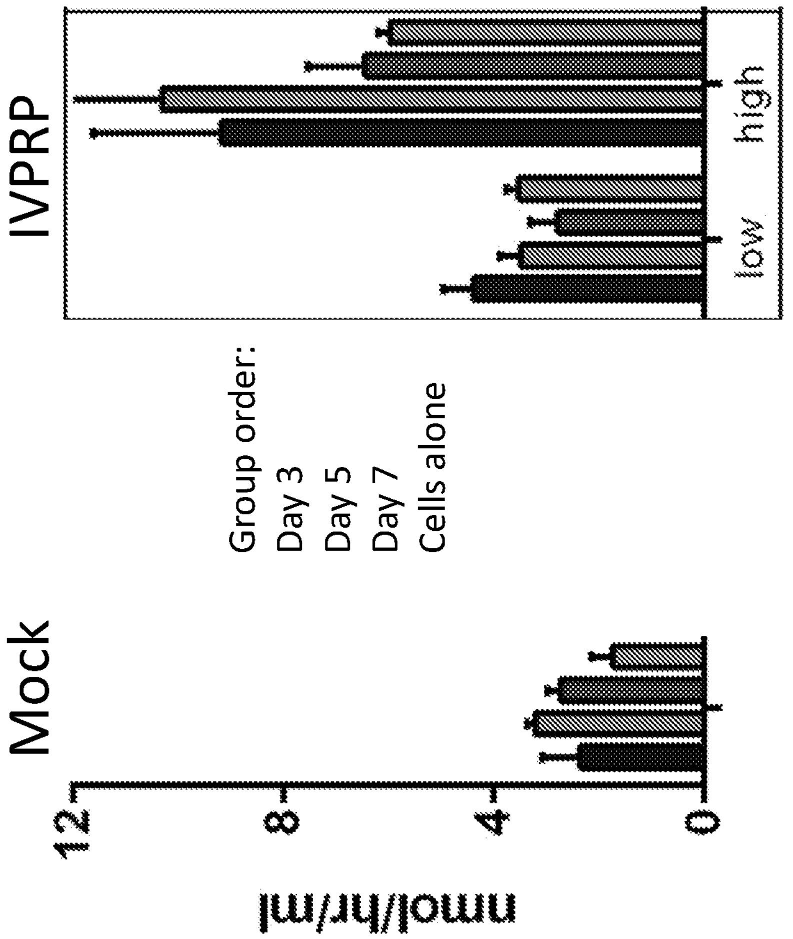
FIG. 2 is a graph showing the α-GalA activity detected in HepG2/C3A cell media over a period of seven days of cells transduced with albumin-specific nucleases (ZFNs) and the donor depicted in FIG. 1C (shown in the right panel labeled "IVPRP" an acronym of "In Vivo Protein Replacement Platform®"). The levels of activity in media from cells that have undergone a mock transduction procedure are shown in the left panel. The bars from left to right show activity at day 3, day 5, day 7 and cells only.
Figure 3A:
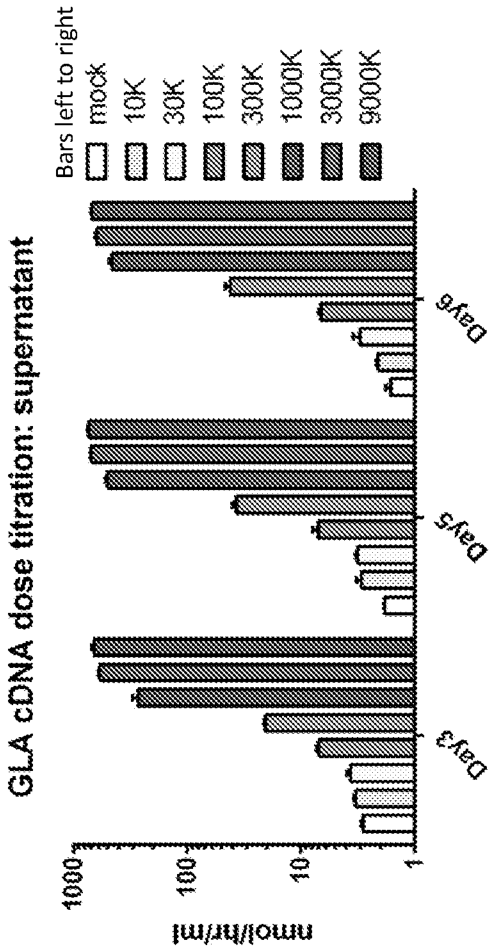
FIGS. 3A and 3B are graphs showing the levels of α-GalA activity detected using the cDNA approach.
Figure 3B:
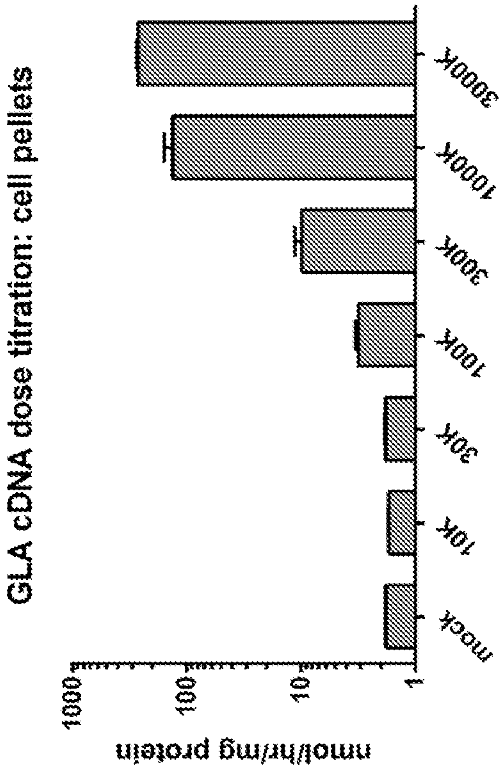

As shown in FIG. 2, transduced cells had increased α-GalA activity in supernatant and cell pellets, and activity reached 3× mock-transduced HepG2 levels in ZFN+donor groups. Indels at the albumin locus, a measure of ZFN activity, were measured at each vector dose for GLA donor constructs A and B. Indels in donors A and B were 43.46% and 39.81% for the 300/600 vector dose and 8.81% and 9.69% for the 100/200 vector dose.

cDNA Approach: the cDNA construct shown in FIG. 1B was also tested in HepG2/G3 cells as described above. As shown in FIG. 3, HepG2/C3a cells transduced with AAV2/6 GLA cDNA vectors had dose-dependent increased α-GalA activity in supernatant and cell pellets. Each dose is labeled in FIG. 3 and indicates the thousands (K) of viral vector copies per cell. Supernatant α-GalA activity reached 200× mock levels at high cDNA doses.

The proteins can be isolated and administered to subject in enzyme replacement therapies.

Example 4: In Vivo Testing of Two Approaches

Next the two types of approaches (cDNA and IVPRP®) were tested in vivo. The constructs were packaged into AAV 2/6 or AAV 2/8 and then injected intravenously into GLA knock out (GLAKO) mice. This is a mouse model of Fabry disease (Bangari et al (2015) *Am J Pathol.* 185(3):651-65). The test articles are shown below (Table 2) along with the dosing regimes (Table 3).

TABLE 2

Test articles for IVPRP ® and cDNA approaches

| | Test Article Label | Test Article | Titer (vg/mL) |
|---|---|---|---|
| IVPRP | Mouse AAV2/8 Surrogate Reagents for SB-GLA | AAV8-hAAT-pCI-Intron-3FN-48641-DNA2.0-FokELD | 3.55E+13 |
| | | AAV8-hAAT-pCI-Intron-3FN-31523-DNA2.0-FokKKR | 3.33E+13 |
| | | AAV2/8-AAV-Fabry-untagged-DNA2.0-MsAlb LS | 2.33E+13 |
| cDNA | Mouse AAV2/6 cDNA for SB-GLA | AAV2/6- AAV-hAAT-pCI-GLA-cDNA2.0 | 1.94E+13 |

TABLE 3

Dosing regimes for in vivo testing of IVPRP ® and cDNA approaches

| Group Designation | Genotype | AAV serotype | ZFN Each Dose Level (vg/mouse) | hGLA Donor Dose Level (vg/mouse) | hGLA cDNA Dose level (vg/mouse) | Total AAV Dose (vg/mouse) | Total AAV Dose* (vg/kg) |
|---|---|---|---|---|---|---|---|
| Formulation buffer control WT | wild type | N/A | $1.5 \times 10^{11}$ | $1.2 \times 10^{12}$ | 0 | $1.5 \times 10^{12}$ | $6.0 \times 10^{13}$ |
| Formulation buffer control KO | GLAKO | N/A | $1.5 \times 10^{11}$ | $1.2 \times 10^{12}$ | 0 | $1.5 \times 10^{12}$ | $6.0 \times 10^{13}$ |
| ZFN + donor | GLAKO | AAV 2/8 | $1.5 \times 10^{11}$ | $1.2 \times 10^{12}$ | 0 | $1.5 \times 10^{12}$ | $6.0 \times 10^{13}$ |
| cDNA low dose | GLAKO | AAV 2/6 | 0 | 0 | $5.0 \times 10^{10}$ | $5.0 \times 10^{10}$ | $2.0 \times 10^{12}$ |
| cDNA high dose | GLAKO | AAV 2/6 | 0 | 0 | $5.0 \times 10^{11}$ | $5.0 \times 10^{11}$ | $2.0 \times 10^{13}$ |

Figure 4A:
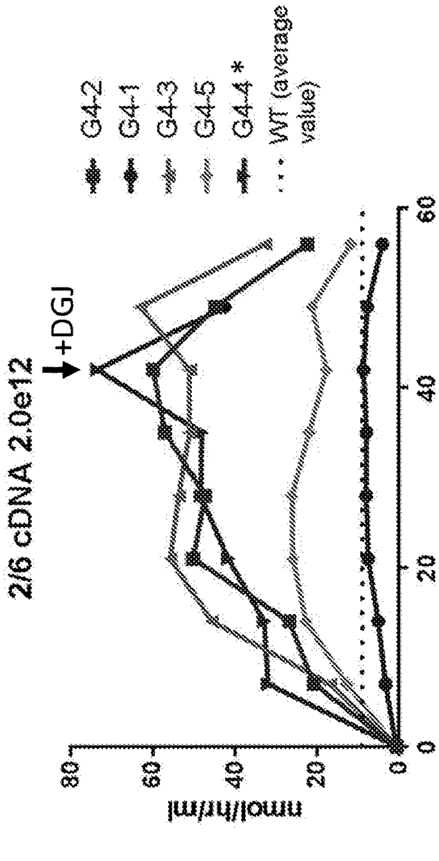
FIGS. 4A and 4B are graphs depicting the in vivo activity in GLAKO mice treated with the cDNA containing AAV.
Figure 4B:
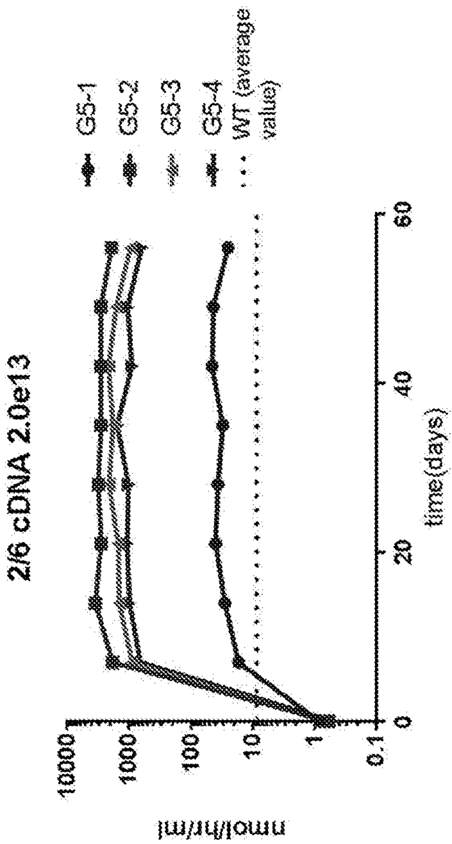
Figure 5A:
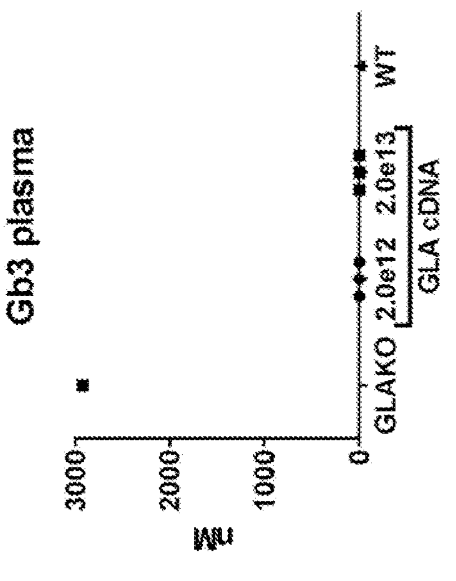
FIGS. 5A through 5F are graphs depicting the levels of the Gb3 lipid substrate in GLAKO mice and in mice treated with the AAV2/6 comprising the cDNA construct.
Figure 5B:
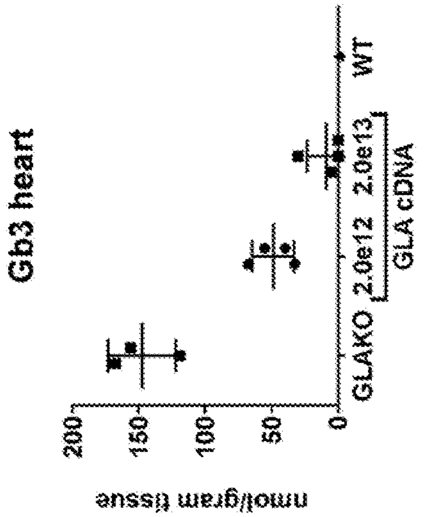
Figure 5C:
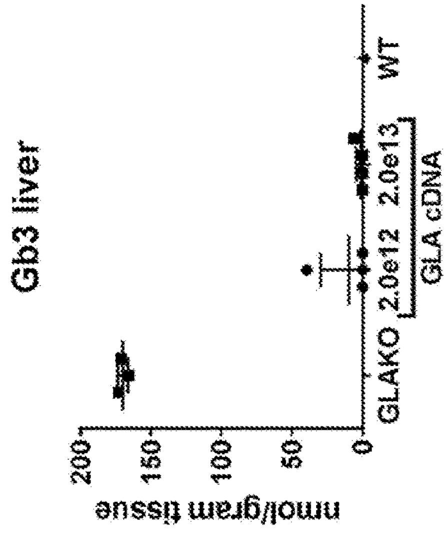
Figure 5D:
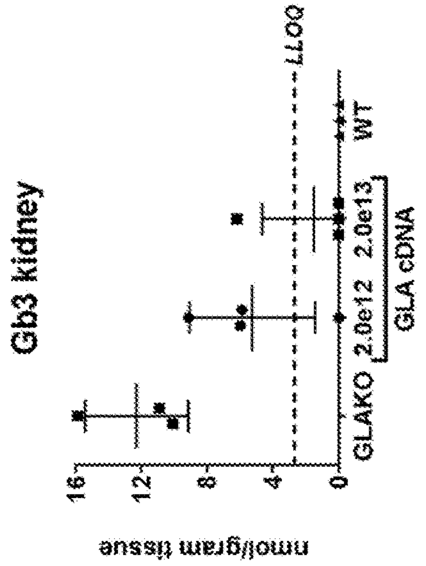
Figure 5E:
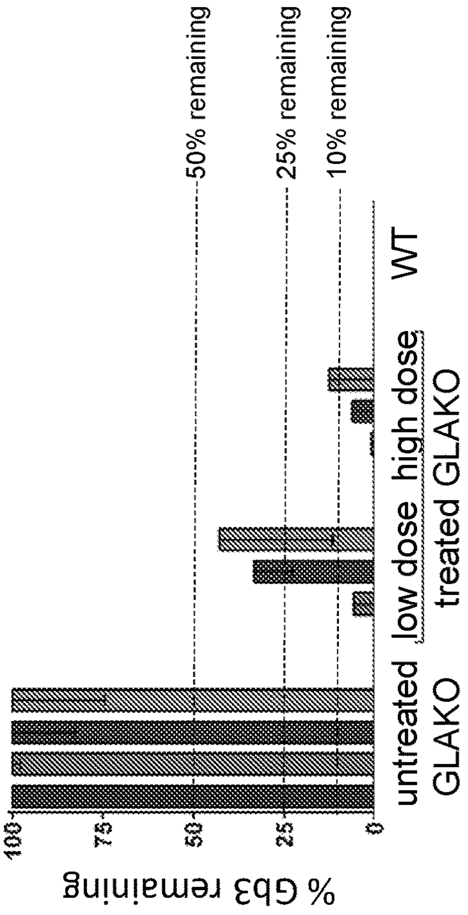
Figure 5F:
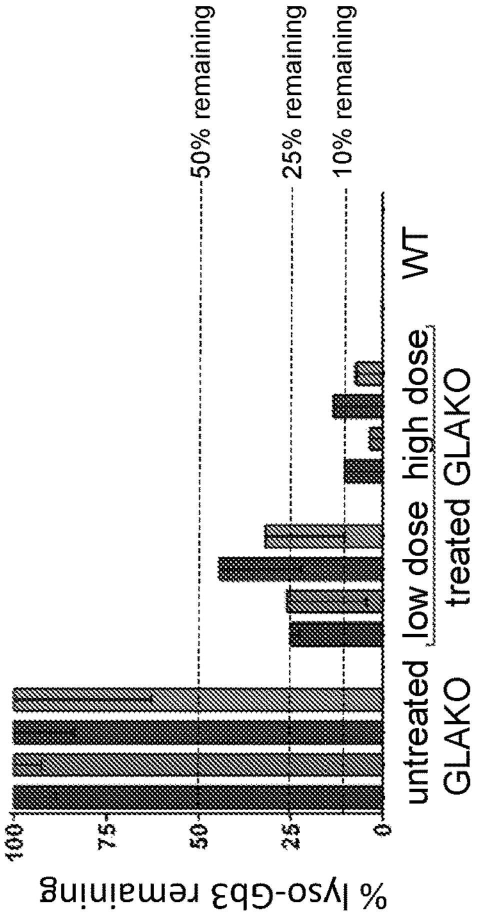

*Animals dosed on a vg/mouse basis. Assuming 0.020 kg body weight for all mice, the total AAV dose level is 7.5e13 vg/kg for animals receiving ZFNs + Donor cDNA Approach:

As shown in FIG. 4, GLAKO mice from cDNA treated groups displayed supraphysiological α-GalA activity in plasma as early as day 7 post-AAV administration. Shown in the figures are the results from the individual mice. Plasma α-GalA activity was measured weekly and high, dose-dependent levels of activity were sustained throughout the duration of the study. Plasma activity reached up to 6× wild type in the low dose (2.0e12 vg/kg) group and 280× wild type in the high dose (2.0e13 vg/kg) group. Mice were euthanized after two months and analyzed for α-GalA activity and Gb3 accumulation in the liver and secondary, distal tissues.

As shown in FIG. 5, dose-dependent increase in α-GalA activity was found in the liver, heart and kidneys along with a corresponding reduction in Gb3 substrate content. Gb3 was undetectable in the tissues of some GLAKO mice administered with the high AAV2/6 cDNA dose. The data was also analyzed in terms of the amount of clearance of the substrates relative to untreated GLAKO mice (FIG. 5E and FIG. 5F) and demonstrated that the mice treated with the high cDNA dose had on average less than 10% of the substrate found in untreated GLAKO mice.

Figures 6A, 6B, 6C, 6D, 6E:
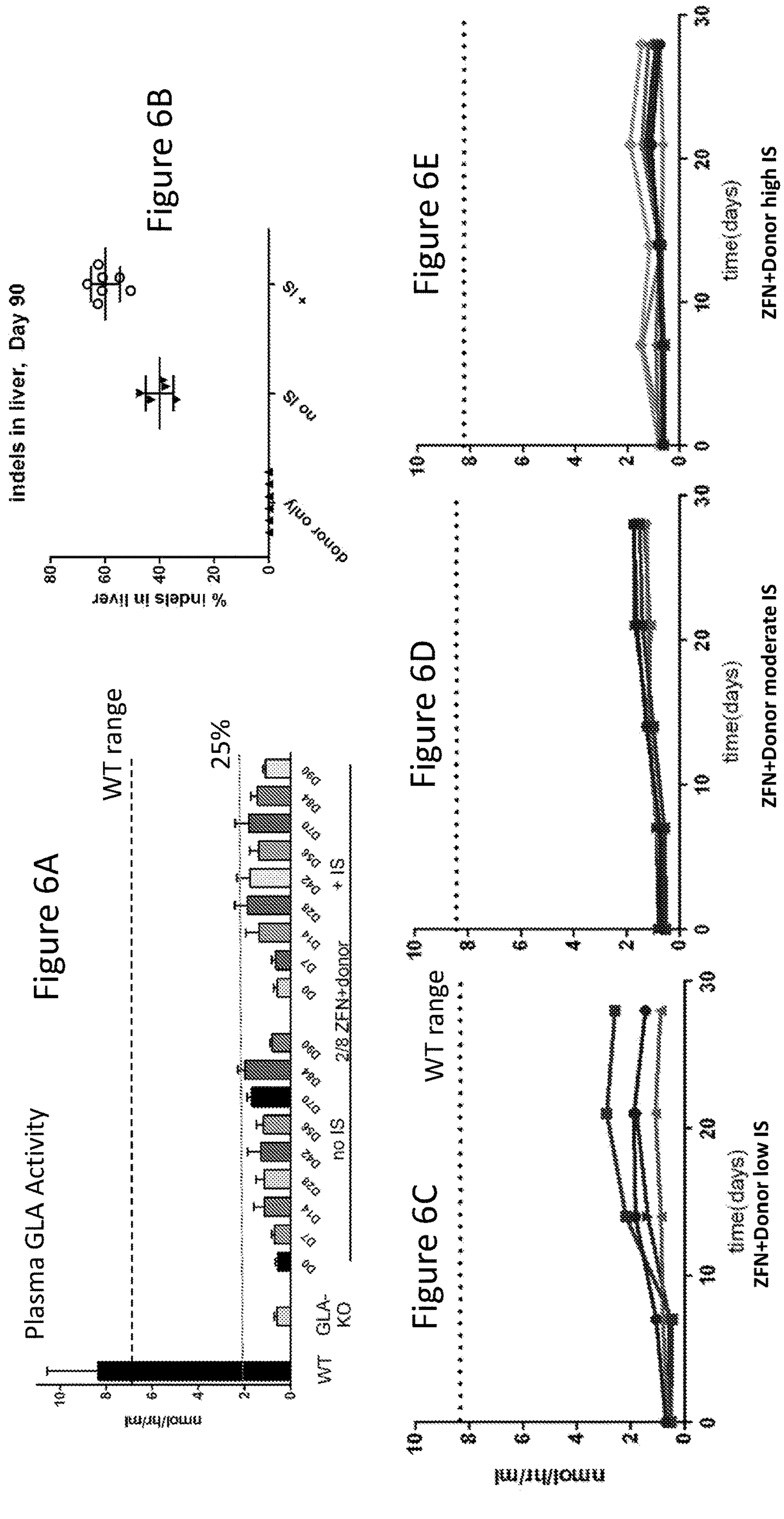
FIGS. 6A though 6E depict the results for the IVPRP approach as tested in vivo.
FIG. 6B is a graph showing the level of indels detected in the liver of the treated animals at day 90. Indels (insertions and/or deletions) are an indication of nuclease activity.
FIGS. 6C, 6D and 6E are time courses of activity detected in the plasma of the treated mice over a period of nearly 30 days.

IVPRP® Approach:

Plasma levels were taken for the IVPRP® approach dosed GALKO mice over a period of 90 days. The data (FIG. 6A) indicate that the α-Gla protein activity was detected in the serum at a level of approximately 25-30% of that seen for wild type mice. In this experiment, one group of cells was given a mild immunosuppression regime (50 mg/kg cyclophosphamide every 2 weeks). Measurement of the ZFN activity in the liver (Indels) found that the animals treated with the mild immunosuppression had a slightly higher level of indels (FIG. 6B), but both groups had the expected range of indels present.

A second experiment was performed using increasingly stringent immunosuppression (dosing shown below in Table 4) and the data (FIGS. 6C, 6D, and 6E) demonstrated that immunosuppression did not significantly increase the α-Gal A protein activity.

TABLE 4

IVPRP ® In vivo study #2, immune suppression titration

Figures 7A, 7B, 7C:
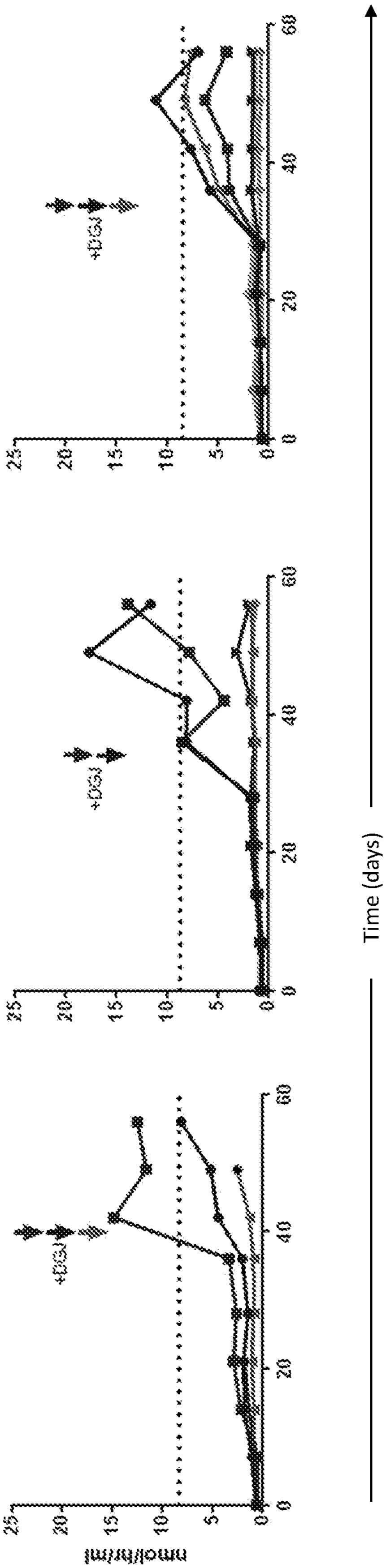
FIGS. 7A through 7C are graphs depicting the α-Gal A activity detected over time in animals treated with both immunosuppression ("IS") and the DGJ chaperone.

| Group | Group Designation | Immunosuppression | hGLA Donor (vg/mouse) | hGLA cDNA Dose level (vg/mouse) | Total AAV Dose (vg/kg) |
|---|---|---|---|---|---|
| 1 | Low IS | 50 mg/kg cyclophosphamide every 2 weeks | $1.2 \times 10^{12}$ | 0 | $6.0 \times 10^{13}$ |
| 2 | Moderate IS | 70 mg/kg cyclophosphamide weekly | $1.2 \times 10^{12}$ | 0 | $6.0 \times 10^{13}$ |
| 3 | High IS | 120 mg/kg cyclophosphamide weekly | $1.2 \times 10^{12}$ | 0 | $6.0 \times 10^{13}$ |
| 4 | cDNA 5e10 | 50 mg/kg cyclophosphamide every 2 weeks | 0 | $5.0 \times 10^{10}$ | $2.0 \times 10^{13}$ |
| 5 | cDNA 5e11 | 50 mg/kg cyclophosphamide every 2 weeks | 0 | $5.0 \times 10^{11}$ | $2.0 \times 10^{13}$ |

α-Gal A is thought to be susceptible to inactivation due to mis-folding as some mutations that are distal to the active site of the protein lead to Fabry Disease (Garman and Garboczi (2004) *J Mol Biol* 337(2):319-35), and that use of molecular chaperones including Deoxygalactonojirimycin (DGJ) have been proposed for use with some GLA mutants (Moise et al (2016) *J. Am. Soc. Mass Spectrom* 27(6): 1071-8). Thus, in the study described above, DGJ was added at approximately day 30-35. Specifically, 3 mg/kg diluted in 200 ul of water was given via oral gavage daily. A rapid rise in α-Gal A activity was detected in animals treated with DGJ (FIG. 7).

Figure 8:
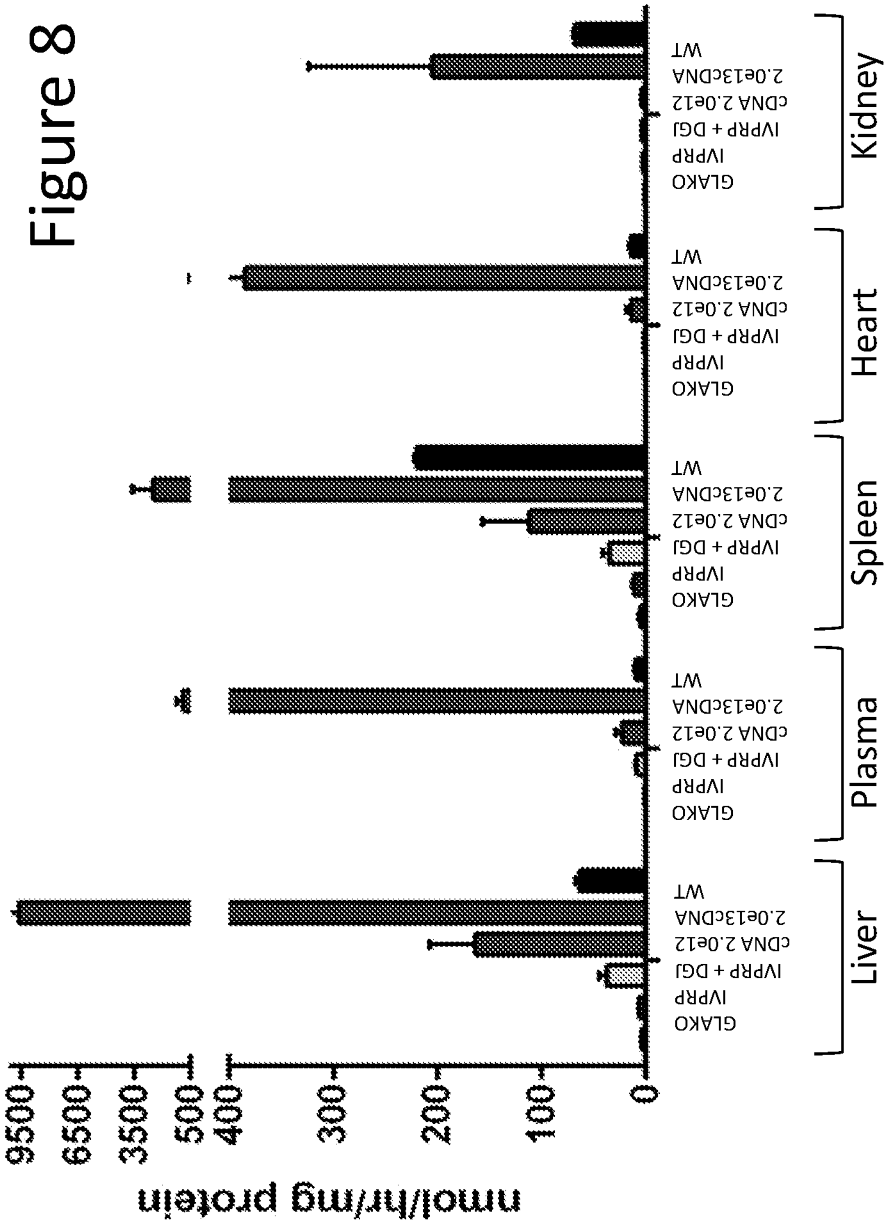
FIG. 8 is a graph showing the comparison of α-Gal A activity in the tissues of the mice treated either via the cDNA or IVPRP approach. Also shown for comparison are levels in wild type mice and in the untreated GLAKO mice. Tissues shown are liver, plasma, spleen, heart and kidney. Note that the Y axis is split, indicating that the cDNA approach at the 2.0e13 VG/kg dose produces α-GalA activity at nearly 100 times the wild-type level and that activity is detectable in all of the tested tissues.

Tissues from the animals in this study were also examined for α-GLA activity as described above. The results (FIG. 8) demonstrated that activity could be detected in the tissues, especially in the liver and spleen. In all tissues, the activity detected for the high dose cDNA approach was higher than for wild type mice.

Figures 9A, 9B:
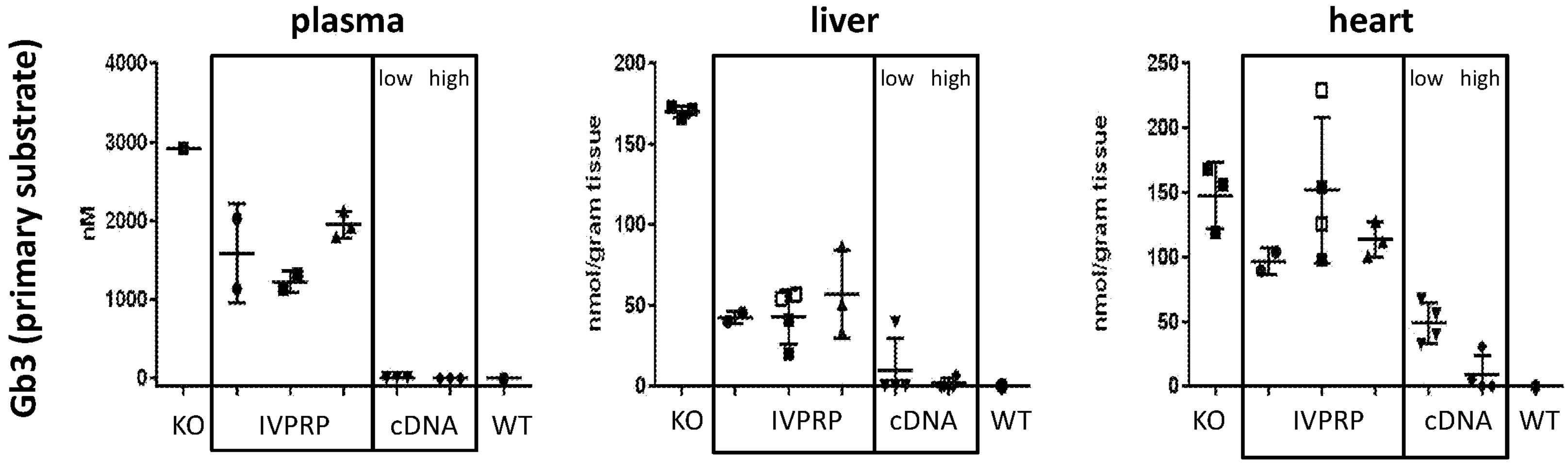
FIGS. 9A through 9C depict the levels of α-GalA activity and Gb3 lipid substrate detected as a result of both the cDNA and In Vivo Protein Replacement Platform® (IVPRP) approaches.
Figure 9C:
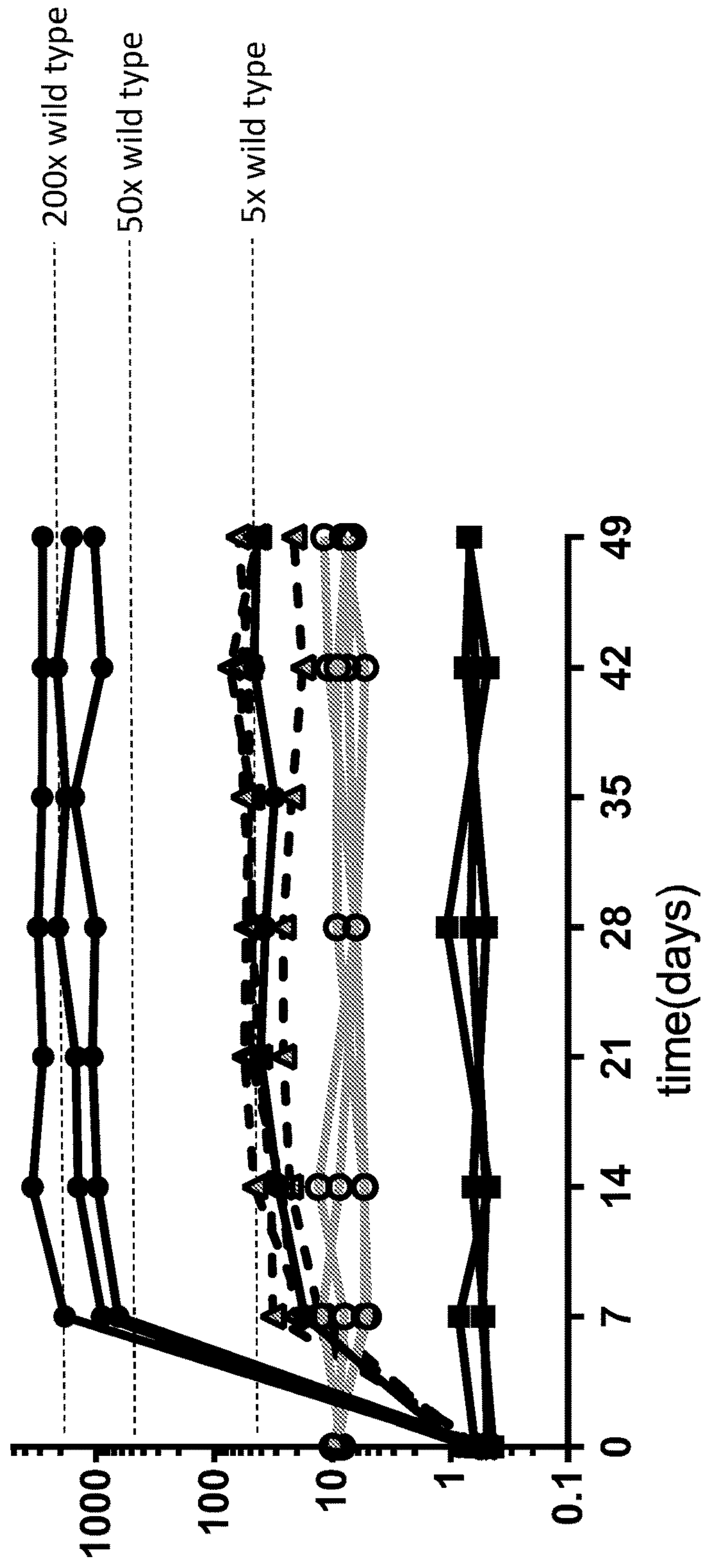
Figure 10:
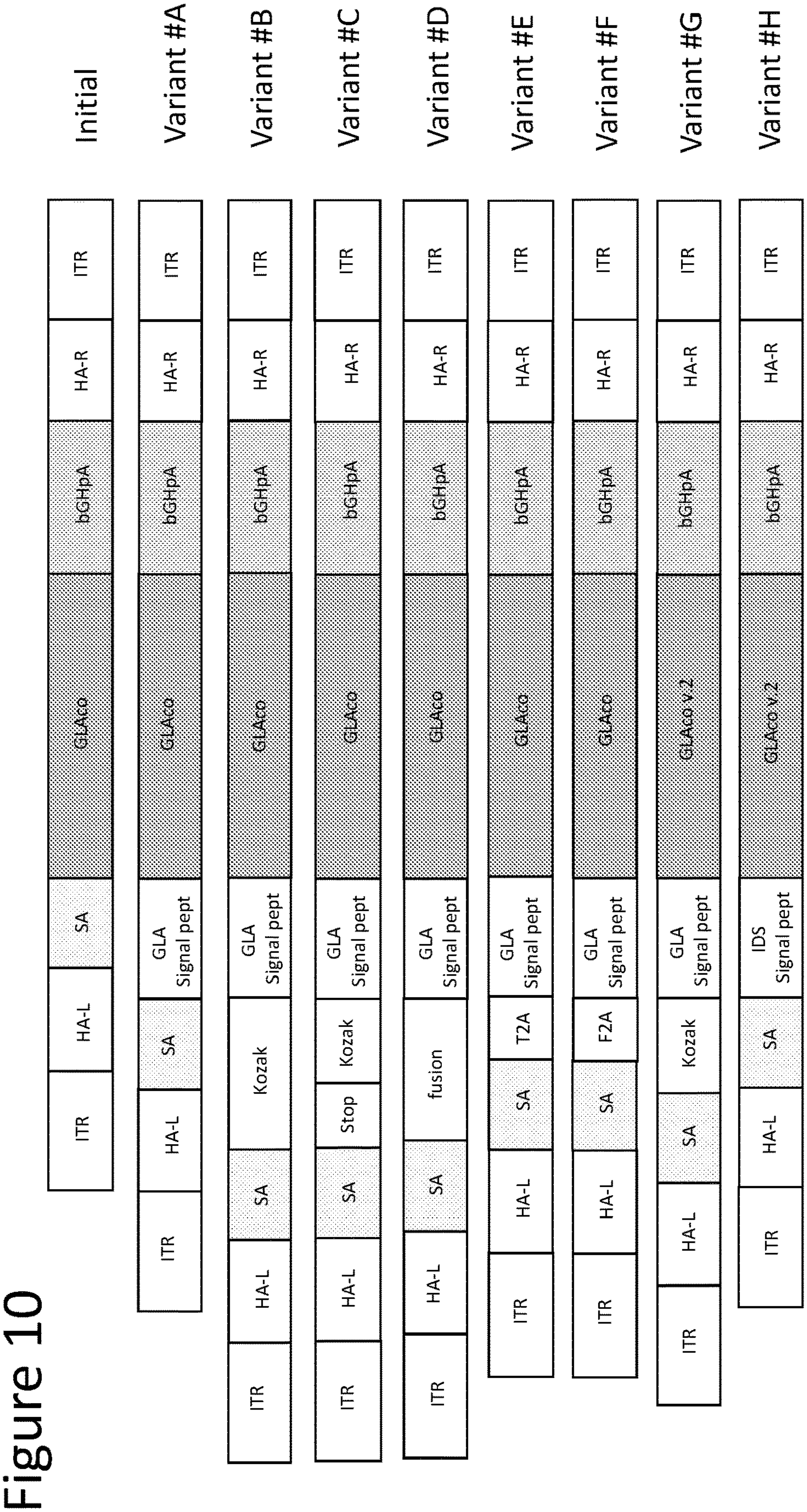
FIG. 10 is a schematic showing various exemplary donor constructs (Variants #A through #L, also referred to as Variants A through L) used for the IVPRP® approach. Abbreviations in the schematics are as follows: "ITR" is the AAV inverted terminal repeat region. "HA-R" and "HA-L" are the right (R) and left (L) homology arms that have homology to the albumin sequence flanking the ZFN cleavage site. "SA" is the splice acceptor site from the F9 gene while "HBB-IGG" is an intron sequence, "GLAco" is the codon optimized α-GalA coding sequence while "GLAco v.2" is an alternate codon optimization of the α-GalA coding sequence "bGHpA" is the poly A sequence from bovine growth hormone, "GLA Signal pept" is the signal peptide from the GLA gene, "fusion" refers to a construct with 2-5 additional amino acids inserted between the splice acceptor site and the GLA transgene, "T2A" and "F2A" are self-cleaving sequences from *T. assigna* and Foot and Mouth Disease virus, respectively. "IDS Signal pept" is the signal peptide for the IDS gene while "FIX Signal pept" is the signal peptide from the FIX gene. "TI" is a 5' NGS primer binding sequence added at 3' end of transgene followed by a targeted integration (TI)-specific sequence with the same base composition as the wild type locus, allowing next generation sequencing to measure indels and HDR-mediated transgene integration simultaneously. See Examples for more details.

The levels of α-Gal A primary substrate were also measured in plasma, liver and heart tissue as described above. The data (FIG. 9) showed a decrease in detectable Gb3 in the plasma for the IVPRP® samples, and no detectable Gb3 for the cDNA samples (equivalent to wild type mice). For liver and heart tissue, the IVPRP® samples also showed a decrease in detectable Gb3, which was also true for the low dose cDNA samples. For the high dose cDNA samples, the levels were nearly the same as the wild type samples.

These results show that the provision of a GLA transgene by either cDNA or IVPRP® approaches as described herein provides therapeutic benefits in vivo.

Example 5: Optimization of the IVPRP Donor Design

The donor design was also investigated for the IVPRP® approach to optimize the design of the GLA coding region and to optimize the signal peptide. To start, the donor design was varied to introduce an α-Gal A (GLA) signal peptide (sequence: MQLRNPELHLGCALALRFLALVSWDIPGARA, SEQ ID NO:1) prior to the GLA coding sequence, and a Kozak sequence (sequence: GCCACCATG, SEQ ID NO:2) was inserted prior to the α-Gal A signal peptide to instigate a new translational event separate from the albumin signal peptide (see FIG. 10, examples are Variant #A, Variant #B). In addition, the use of alternate IDS signal peptide (sequence: MPPPRTGRGLLWLGLVLSSVCVALG, SEQ ID NO:3) was analyzed (FIG. 10, Variant #H) including and the use of a 2A-like sequence from *T. asigna* ("T2A") (Luke et al (2008) *J Gen Virol.* 89(Pt 4): 1036-1042) to remove sequences 5' of the signal peptide during translation. The new constructs were tested in HepG2/C3A cells as described previously.

Figure 11A:
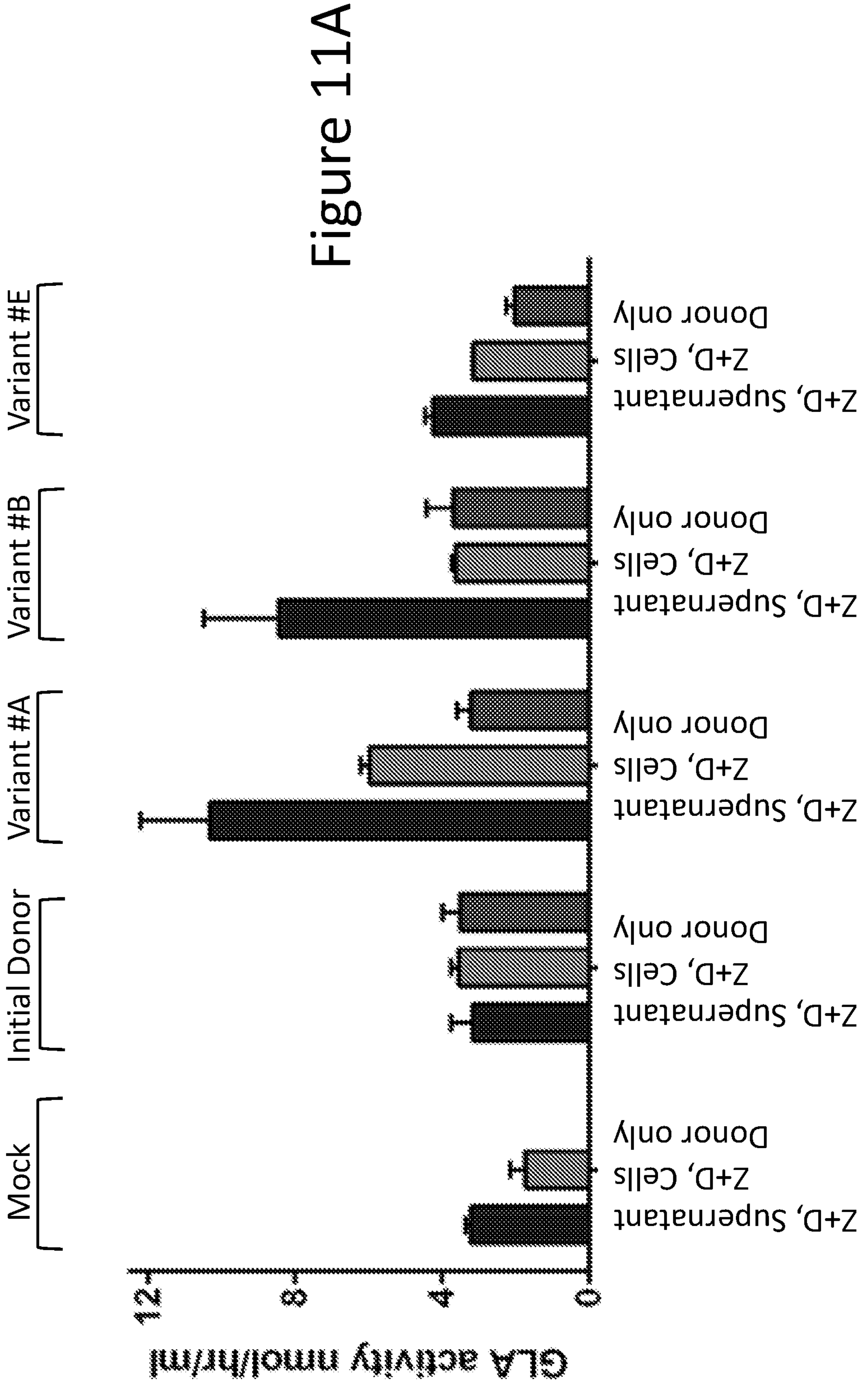
FIGS. 11A and 11B are graphs depicting α-GalA activity in vitro in HepG2/C3A cells. Shown in FIG. 11A are the activity detected in the cells and in the cell supernatant using the initial donor and the donor variants #A, #B, and #E as shown in FIG. 10. "Z+D" refers to ZFN and donor administration. The data indicate that Variants #A and #B had greater activity than the initial donor.
Figure 11B:
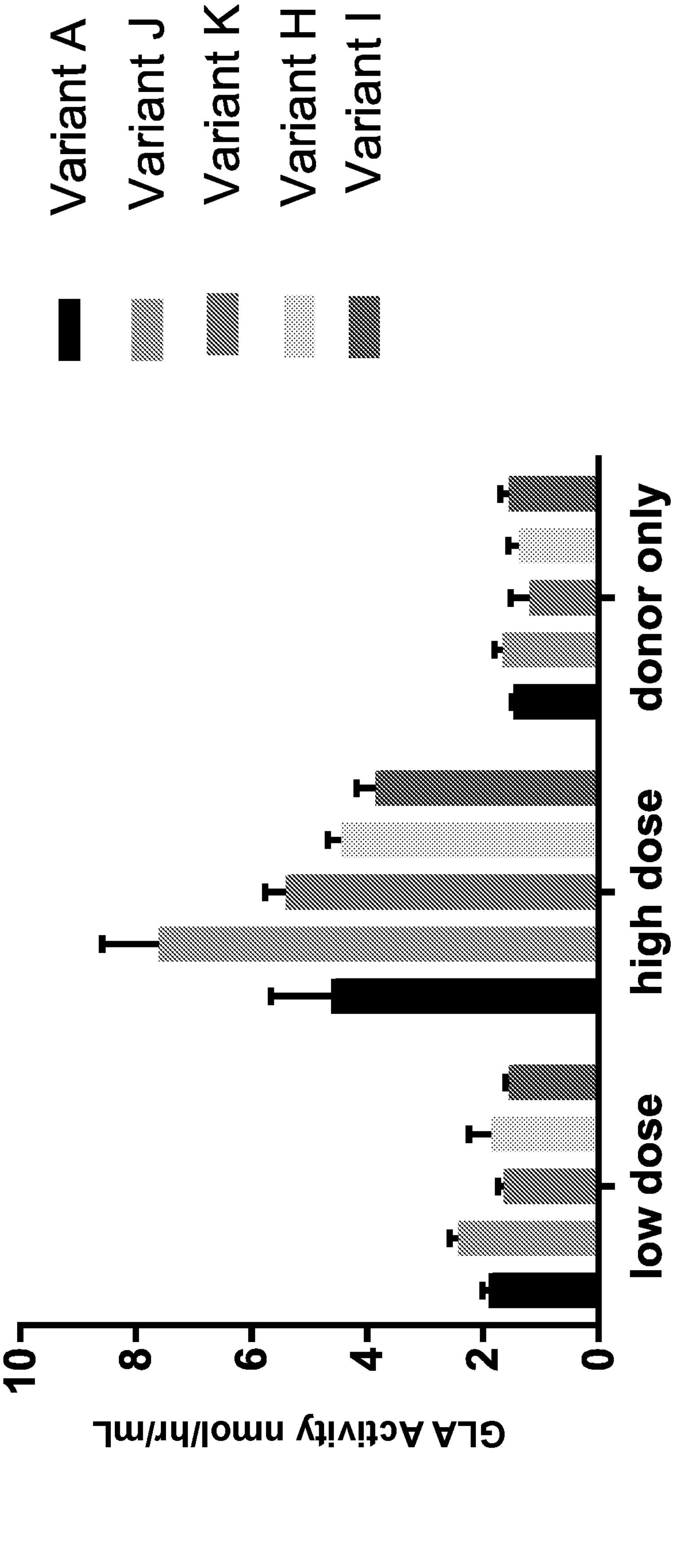

The results showed that the Variant #A and Variant #B had much higher levels of α-GalA activity than the initial donor (FIG. 11A) in vitro. In addition, Variant K demonstrated even higher levels of α-GalA activity as compared to Variant A or the initial donor (FIG. 11B).

The constructs were then tested in vivo in the GLAKO mice using the dosing protocol listed below in Table 5.

TABLE 5

In vivo testing of IVPRP ® donor designs in GLAKO mice

| Group# | Group Designation | Genotype | No. of Mice | ZFN Each Dose Level (vg/mouse) | hGLA Donor Dose Level (vg/mouse) | Total AAV Dose (vg/mouse) | Total AAV Dose* (vg/kg) |
|---|---|---|---|---|---|---|---|
| 1 | ZFN + initial Donor | GLAKO | 5 | $1.5 \times 10^{11}$ | $1.2 \times 10^{12}$ | $1.5 \times 10^{12}$ | $6.0 \times 10^{13}$ |
| 2 | ZFN + new Donor #A + GLAsp | GLAKO | 5 | $1.5 \times 10^{11}$ | $1.2 \times 10^{12}$ | $1.5 \times 10^{12}$ | $6.0 \times 10^{13}$ |
| 3 | ZFN + new Donor #B + Kozak, +GLAsp | GLAKO | 5 | $1.5 \times 10^{11}$ | $1.2 \times 10^{12}$ | $1.5 \times 10^{12}$ | $6.0 \times 10^{13}$ |
| 4 | ZFN + new Donor #E + T2A, +GLAsp | GLAKO | 5 | $1.5 \times 10^{11}$ | $1.2 \times 10^{12}$ | $1.5 \times 10^{12}$ | $6.0 \times 10^{13}$ |

Figure 12:
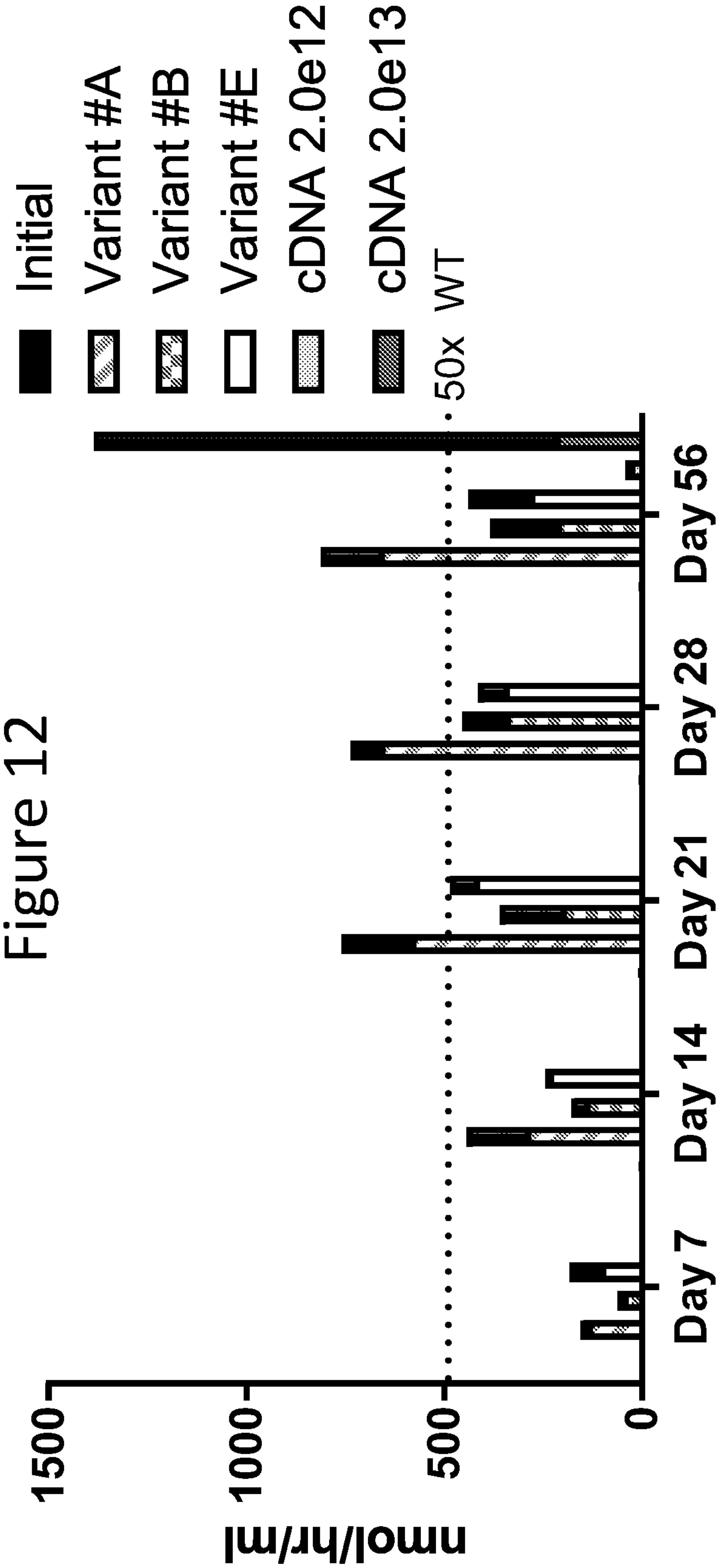
FIG. 12 is a graph showing the activity of the variants #A, #B and #E in vivo. GLAKO mice were used and plasma samples were taken once per week.

Plasma was taken once per week to measure α-Gal A activity as described above. Activity was found in all samples in each mouse, with the new designs showing improvement over the initial donor (FIG. 12), and levels were at least 40-fold higher than wild type at day 28 (indicated by the dotted line). Samples over time showed an increase, where activity was measure at approximately 80× wild type levels for Group 2 (Donor #A) and 50×WT for Group 4 (Donor #E). Tissue samples are taken from the mice and the levels of Gb3 are measured and are found to be reduced as compared to the untreated GLAKO mice.

Figure 15A:
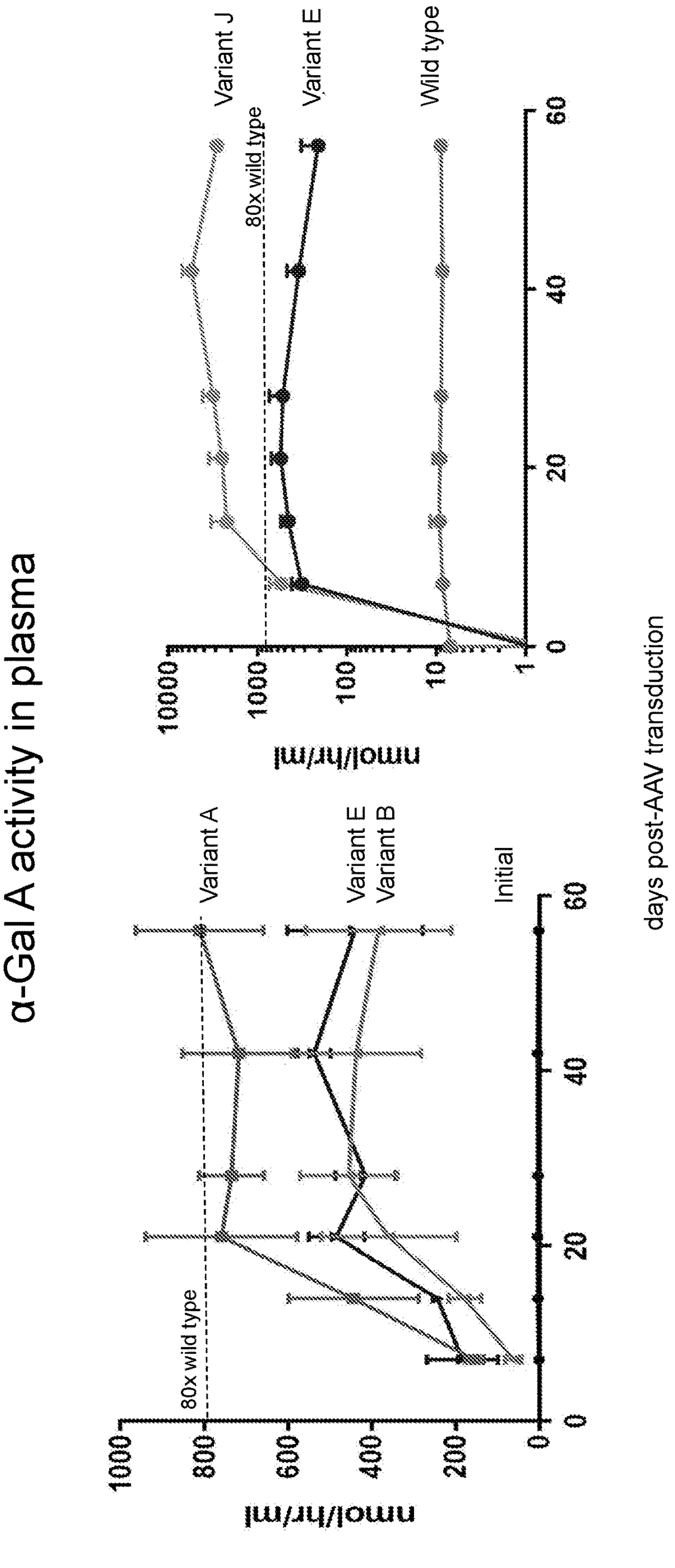
FIGS. 15A through 15C are graphs depicting α-Gal A activity in either plasma (FIG. 15A) or in select tissues (FIG. 15B). GLAKO mice were injected with 3e11 VG of ZFNs designed to create a double strand break in Albumin intron 1 and 1.2e12 VG of the initial GLA donor construct or variants A, B, E or J (total AAV dose/mouse=6e13 VG/kg).
Figure 15B:
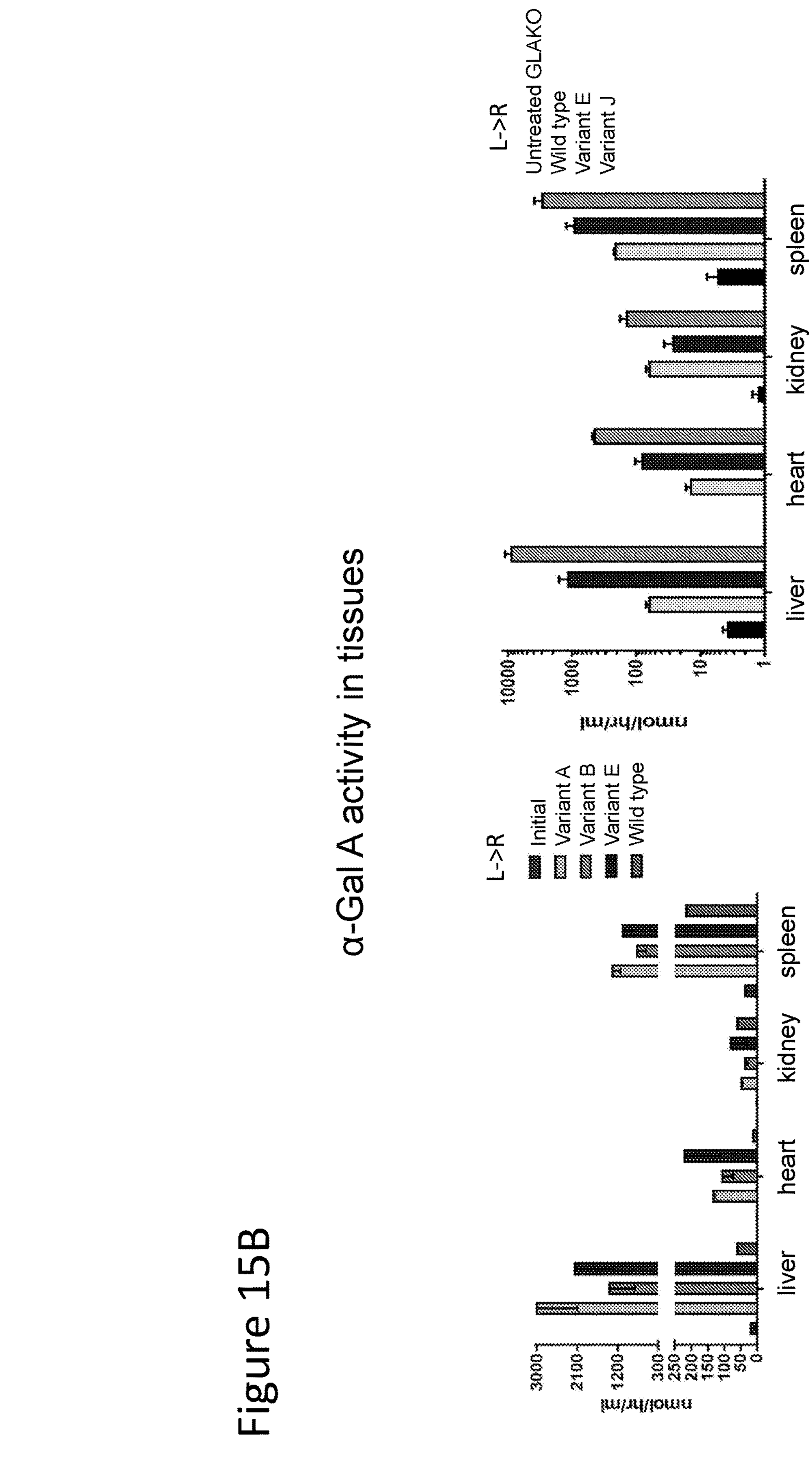
Figure 15C:
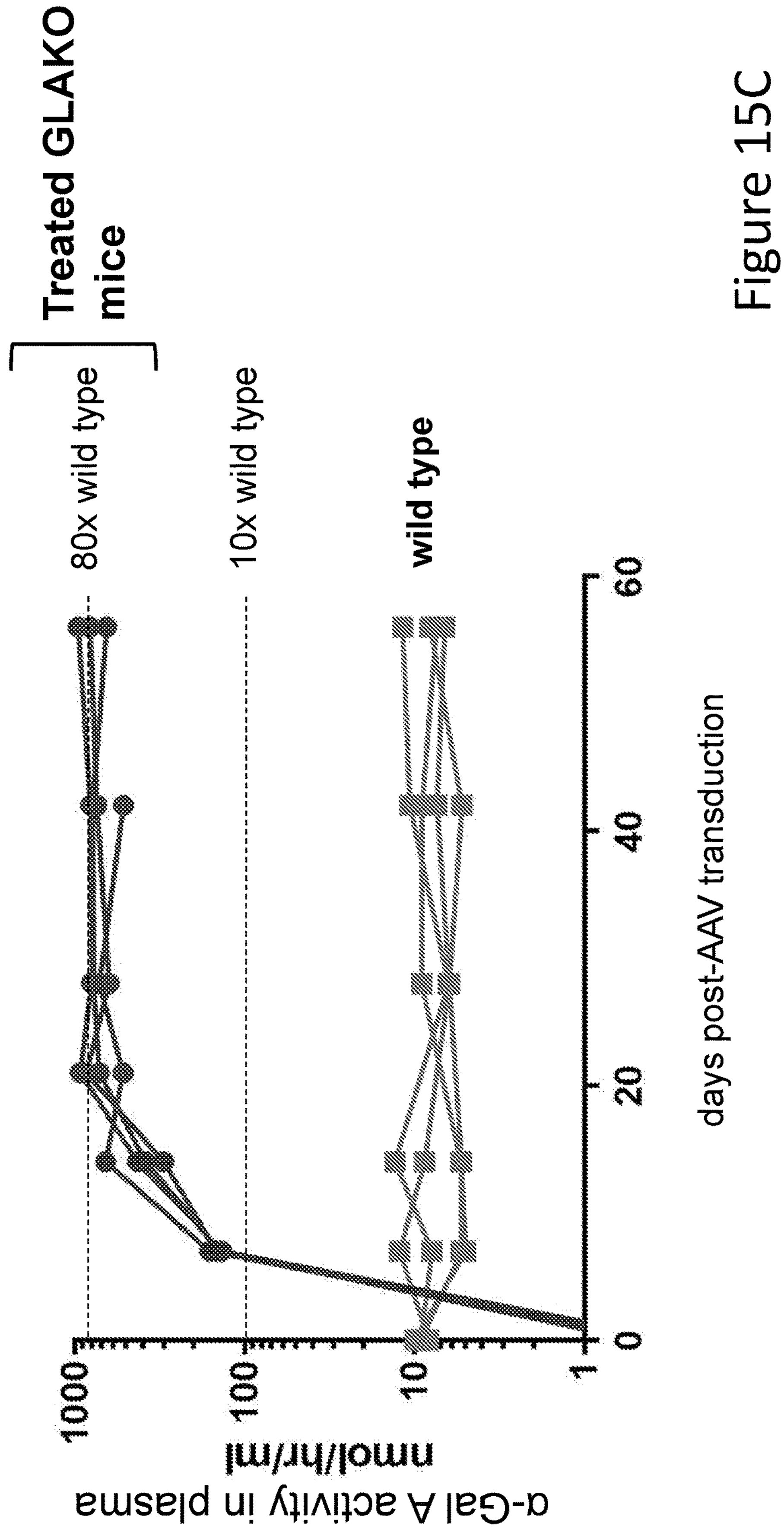

The experiment described above was carried out for 56 days, at which time the animals were sacrificed and analyzed for α-Gal A activity in the liver, heart, kidney and spleen. The extended data (FIG. 15) demonstrates that this approach resulted in increases in α-Gal A activity in tested tissues, including a 100-fold increase in α-Gal A activity in plasma of treated animals as compared to plasma of wild-type animals, a 9-fold increase in α-Gal A activity in the heart of treated animals as compared to the hearts of wild-type (untreated) animals, and an 80% increase in α-Gal A activity in the kidneys of treated animals as compared to untreated (wild-type) animals.

Figure 16B:
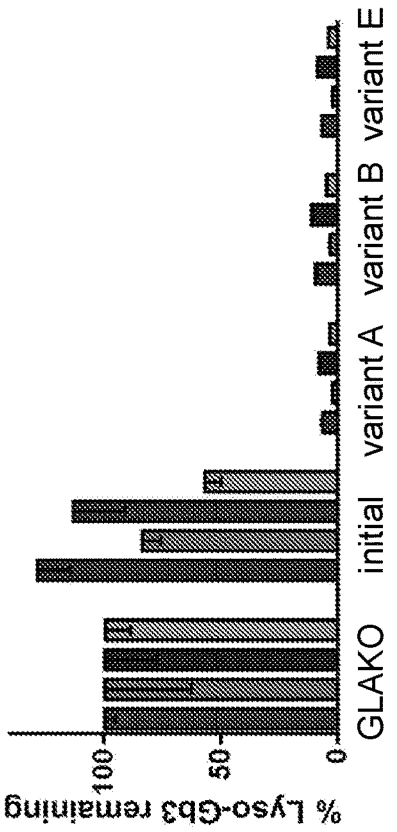
FIGS. 16A and 16B are graphs depicting the amount of α-Gal A glycolipid substrate (Gb3 and lyso-Gb3) remaining following treatment with the ZFN+different donor variants. Gb3 (FIG. 16A) and lyso-Gb3 (FIG. 16B) content was measured in plasma, heart, liver, kidney and spleen (spleen data not shown) via mass spectrophotometry. Each dataset is shown in groups of 4, depicting the levels (from left to right in each group) in plasma, liver, heart and kidney. The amount of substrate is expressed as the fraction remaining, compared to untreated GLAKO mice. The amount of both Gb3 and lyso-Gb3 was greatly reduced in the tissues of mice treated with GLA donor variants A, B or E.
Figure 16A:
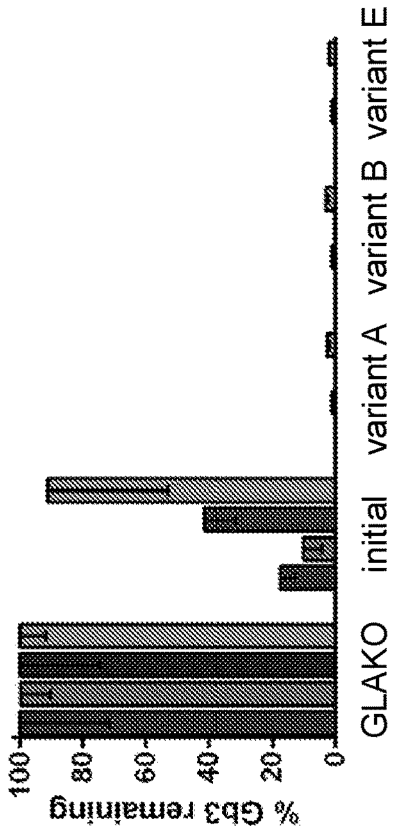

Tissue analysis was then done to determine the levels of α-Gal A glycolipid substrates (Gb3 (FIG. 16A) and lyso-Gb3 (FIG. 16B)) in various tissues (plasma, liver, heart and kidney) following treatment. As shown in FIG. 16, treatment as described herein resulted in decreased levels of both substrates (Gb3 and lyso-Gb3) in all tested tissues (plasma, liver, heart and kidney) for animals treated with A, B or E variants as compared to before treatment (initial) and untreated (wild-type) animals, indicating that the compositions and methods described herein provide therapeutically beneficial levels of protein in vivo.

Figure 20A:
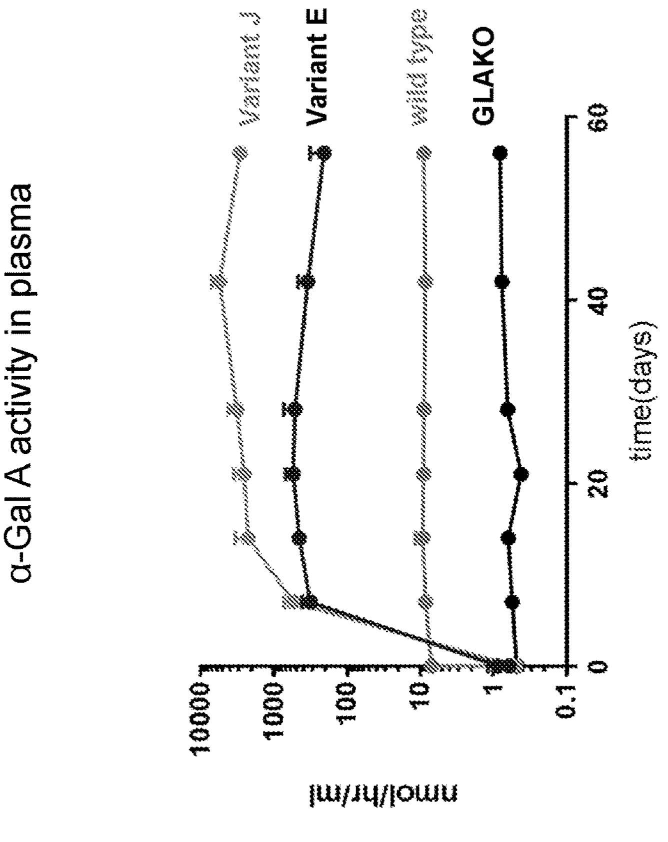
FIGS. 20A and 20B are graphs depicting the α-Gal A activity detected following in vivo expression of Variants E and J.
Figure 20B:
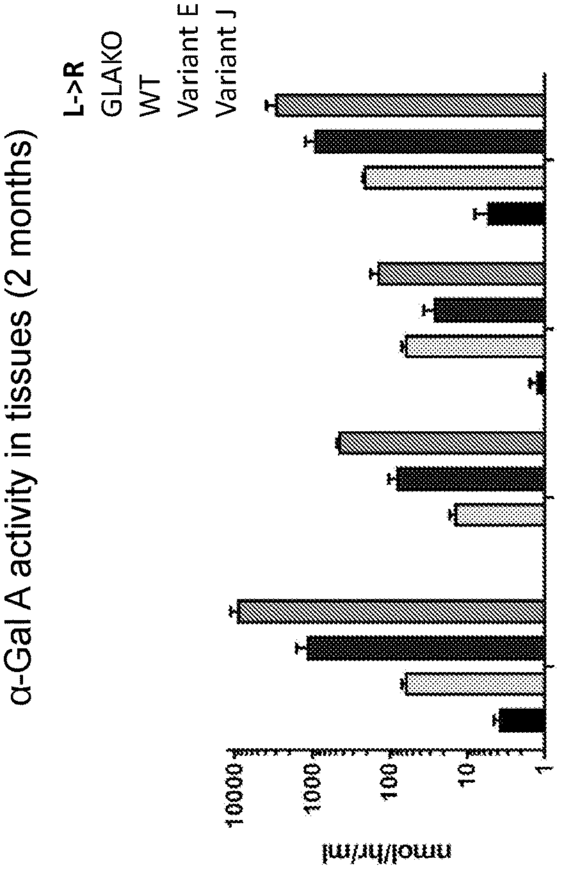

The experiments were repeated as described above to assay α-Gal A activity in plasma and in various tissues (liver, hear, kidney and spleen) following administration of Variant E and Variant J (see FIG. 10) with albumin-targeted ZFNs. As shown in FIGS. 20 and 21, α-Gal A activity in plasma (FIG. 20A) and in liver, heart, kidney and spleen (FIG. 20B) of animals receiving Variant J donor produced plasma α-Gal A activity nearly 300× that of wildtype and tissue α-Gal A activity 10-100× or more than that of wildtype in liver, heart and spleen.

Figure 21A:
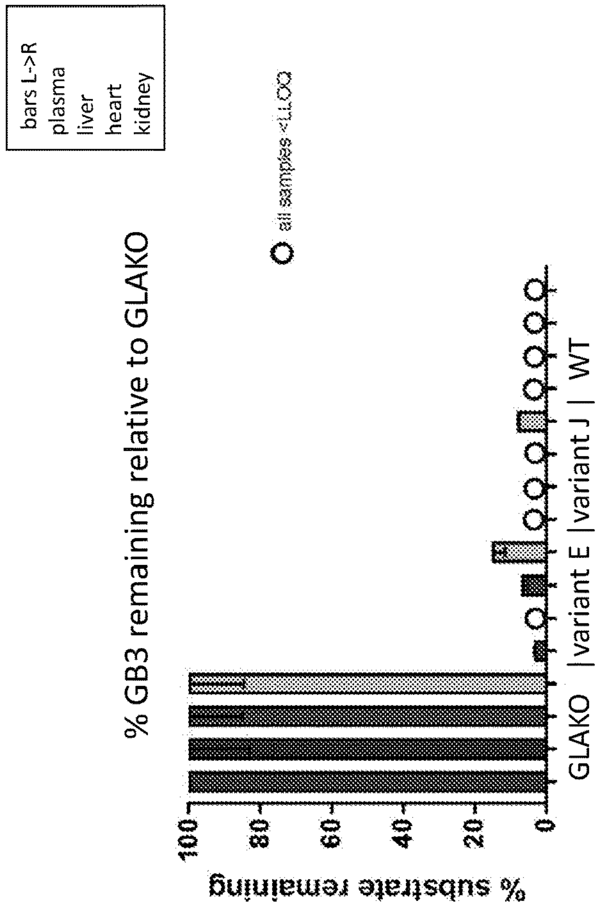
FIGS. 21A and 21B are graphs depicting the amount of α-Gal A substrate detected in various tissues of interest (plasma, liver, heart and kidney).
Figure 21B:
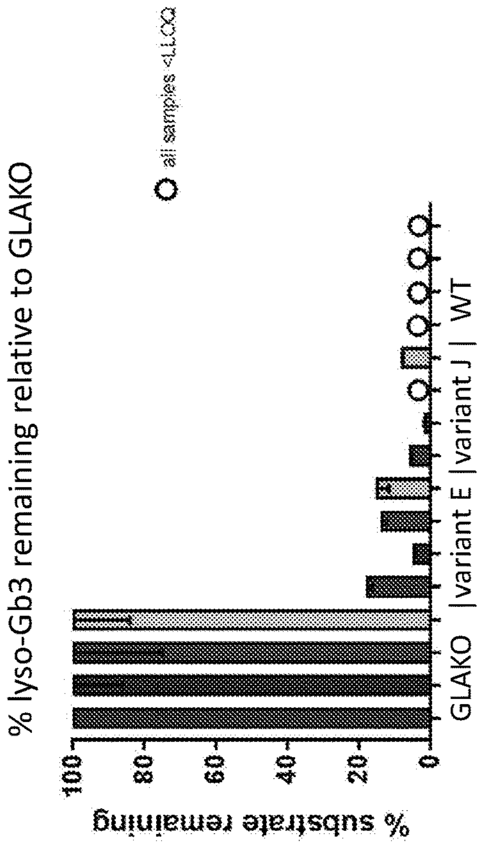

The concentrations of α-Gal A glycolipid substrates (Gb3 (FIG. 21A) and lyso-Gb3 (FIG. 21B)) in various tissues (plasma, liver, heart and kidney) following treatment were measured as described herein. As shown in FIG. 21, expression of Variant J greatly reduced the substrate levels.

Example 6: Optimization of GLA Transgene Cassette Design for cDNA Approach

Figures 13A, 13B:
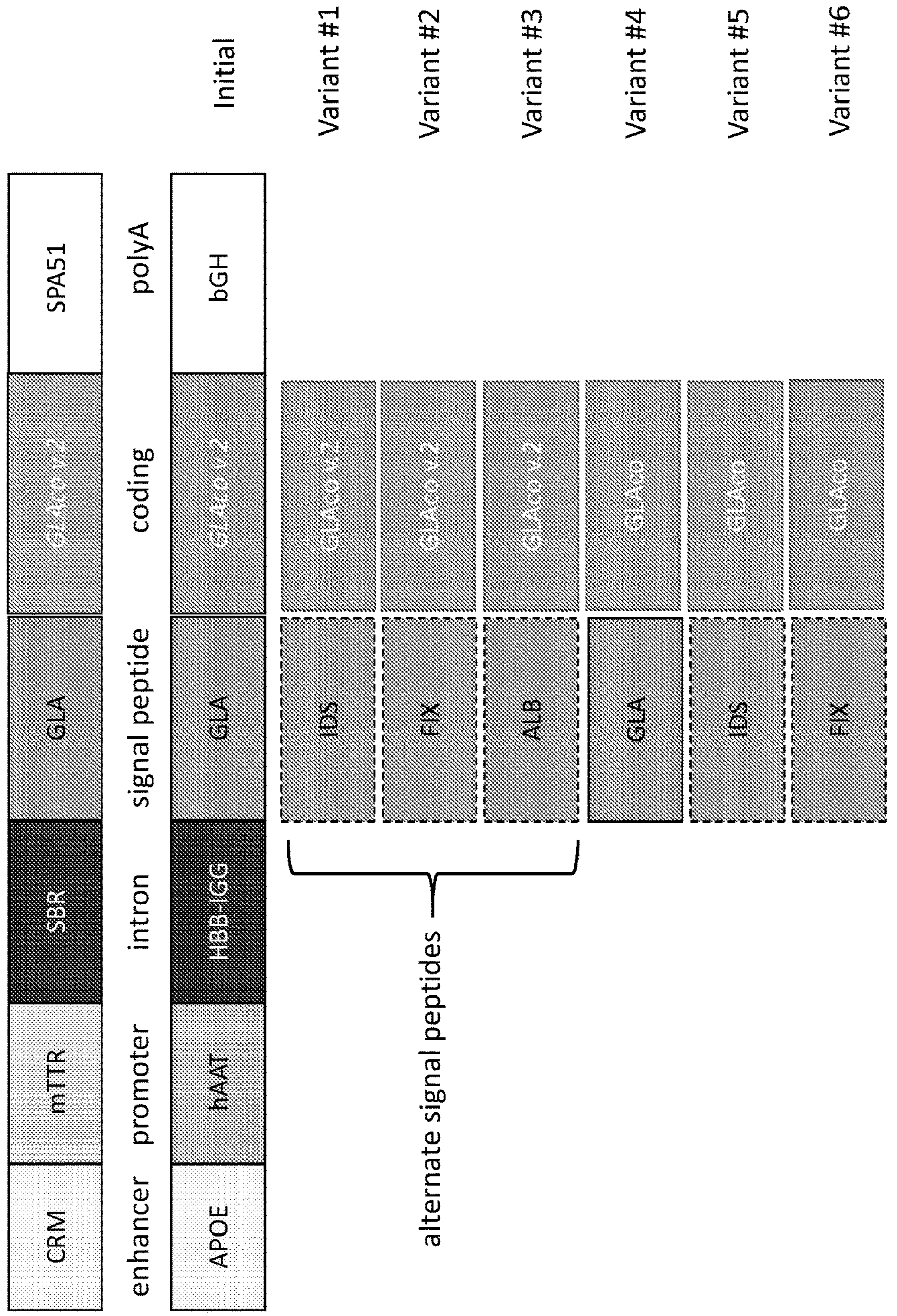
FIGS. 13A and 13B are schematics of exemplary cDNA expression cassettes.
Figure 14B:
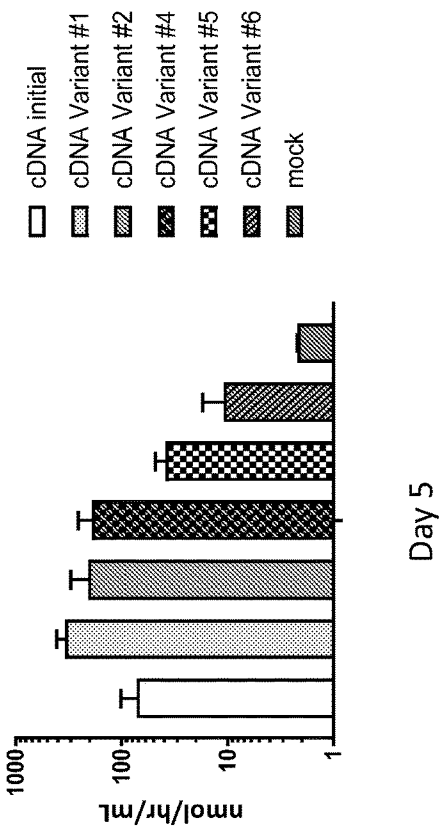
FIGS. 14A and 14B are graphs showing the expression of α-GalA activity using the cDNA approach. In the figure, HepG2/C3A cells were transduced with AAV comprising the indicated cDNA construct, where the effects of varying the signal peptides as shown in FIG. 13B were tested. α-Gal A activity was measured in the cell supernatant at day 3 and day 5, and the results indicated that the IDS and FIX (F9) leader sequence lead to higher levels of activity than either the GLA or albumin (ALB) leader sequences.
Figure 14A:
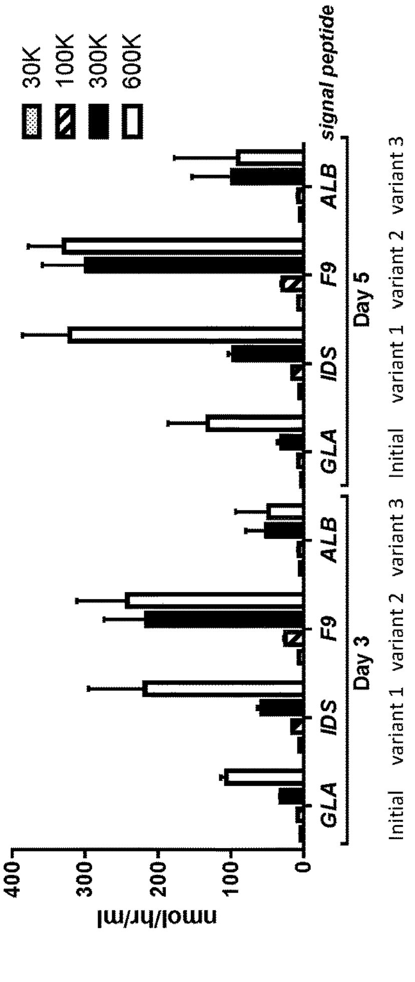

The GLA transgene cassette for the cDNA approach was also optimized. The transgene was linked to sequences encoding different signal peptides, including the α-Gal A peptide, the signal peptide for the IDS gene (iduronate 2-sulfatase), the FIX gene (Factor IX, (sequence: MQRVN-MIMAESPGLITICLLGYLLSAEC, SEQ ID NO:4)) and the albumin (sequence: MKWVTFISLLFLFSSAYS, SEQ ID NO:5) signal peptides (FIG. 13B). In addition, the GLA transgene was inserted into an alternate optimized cDNA expression vector (FIG. 13A, also U.S. Publication No. 20170119906). All constructs were tested as described above in HepG2/C3A cells in vitro at doses ranging from 30 to 600 thousand (K) of viral vector copies per cell, and indicated that the IDS and FIX (F9) leader sequences lead to greater α-GalA activity than use of the GLA or ALB (albumin) leader sequences (FIG. 14A). The data for the cDNA variants #4, #5 and #6 (FIG. 13) is shown in FIG. 14B.

The constructs are also tested in GLAKO mice as described above and are active in vivo.

Example 7: Analysis of α-Gal a Protein by Western Blot and Deglycosylation

Plasma from the mice treated with either the IVPRP® approach or the cDNA approach was analyzed for the presence of the α-GalA protein as described in Example 2. Further, the samples were also treated with PNGaseF to cause deglycosylation.

Figure 17A:
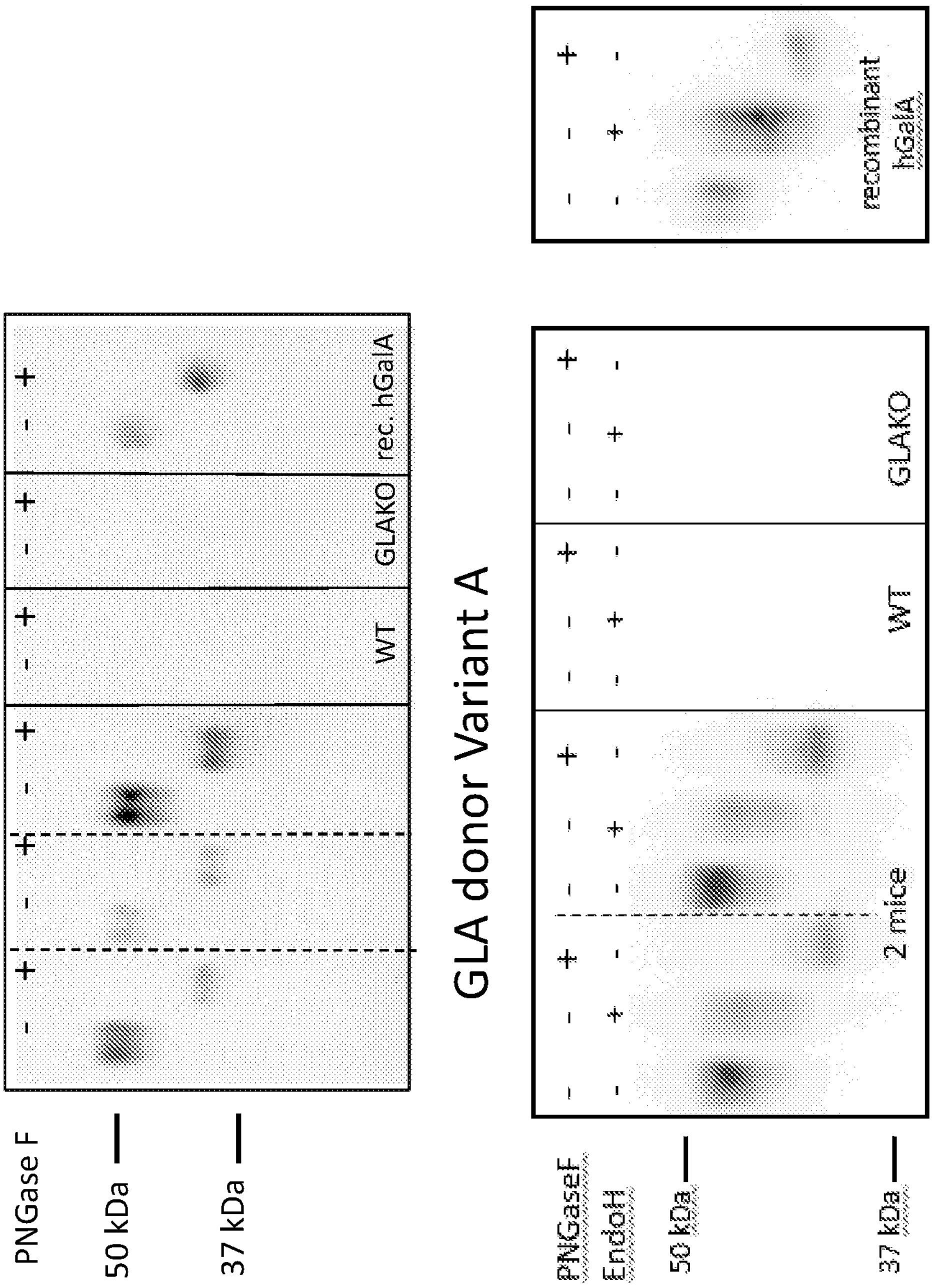

As shown in FIG. 17, the α-GalA protein produced in vivo in the GLAKO mice following either IVPRP® (FIG. 17A depicting the results for Variant A and Variant J) or the initial cDNA construct (construct depicted in FIG. 13B, data shown in FIG. 17B) treatment behaved similarly to the recombinant hGalA protein, indicating the composition and methods described herein provides proteins at clinically relevant levels, namely therapeutic levels similar to those recombinant therapeutic proteins currently in use in enzyme replacement therapies.

Example 8: In Vitro Protein Production Following cDNA Administration

Hep2G cells were transduced with AAV GLA cDNA Variant #4 and the supernatant was collected after 5 days and tested for α-Gal A activity and the supernatant used in culture of K562 cells as described in Example 2.

Figure 28A:
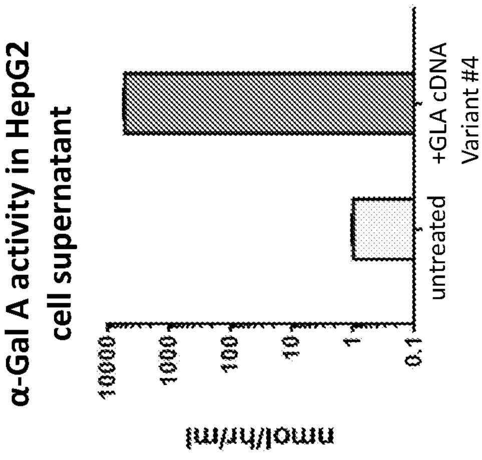
FIGS. 28A and 28B are graphs depicting α-GAL A activity in cells treated with liver specific constructs comprising a GLA construct.
Figure 28B:
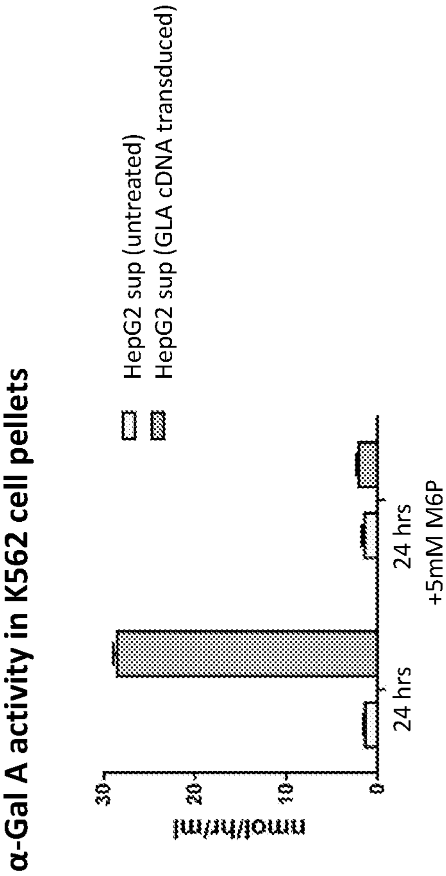

As shown in FIG. 28A, supernatant collected 5 days after transduction of HepG2 cells with the AAV GLA cDNA Variant #4 showed high amounts of α-Gal A activity. FIG. 28B shows α-Gal A from the HepG2 supernatant was taken up by the K562 within 24 hours and that uptake was blocked by M6P.

Therefore, cells as described herein produce and secrete α-Gal A in high amounts, which secreted α-Gal A is then taken up by other cells. Accordingly, the systems described herein can be used for the production of α-Gal A for administration of the subjects in need thereof, for example in enzyme replacement therapies.

Example 9: In Vivo Activity of Mice Treated with cDNA Variant #4

Figure 18A:
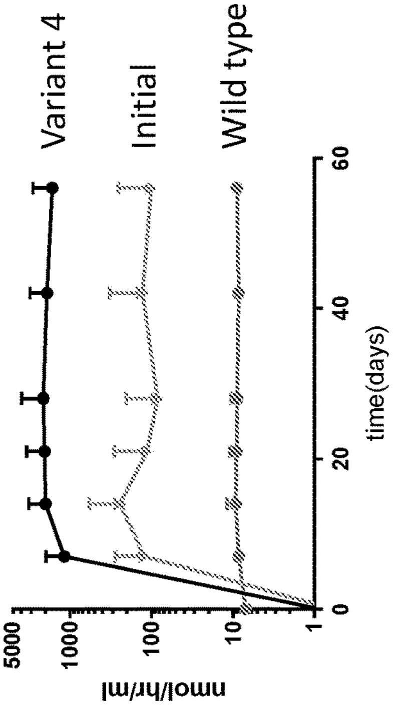
FIGS. 18A through 18C are graphs depicting activities measured using the initial cDNA construct as compared to Variant #4 (shown in 13B above).
Figure 18B:
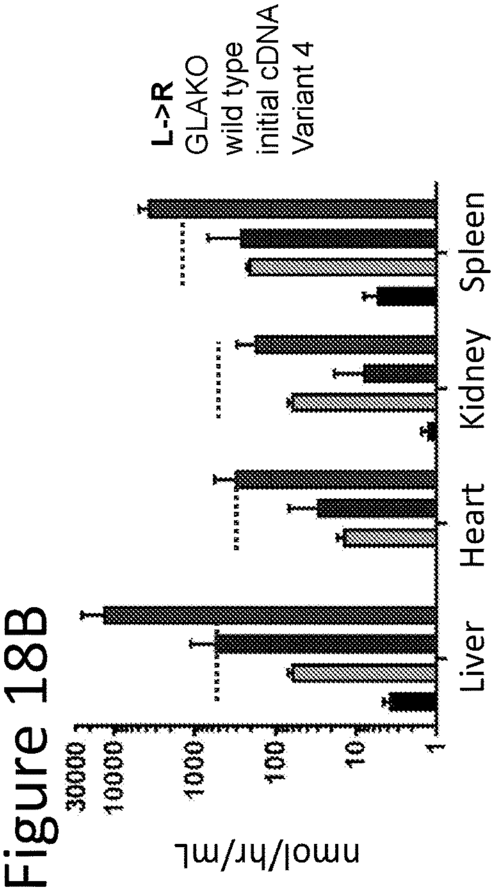
Figure 18C:
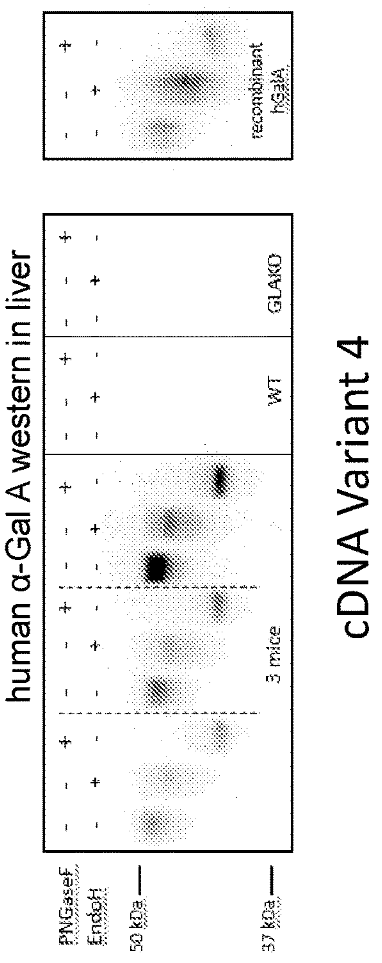
Figure 32B:
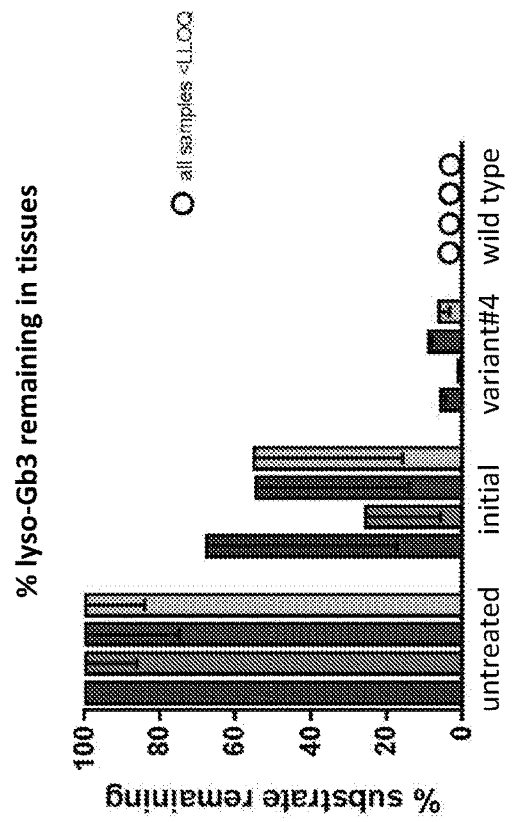
FIGS. 32A and 32B graphs depicting the percent of Gb3 substrate remaining in various tissues of interest (plasma, liver, heart and kidney) after the indicated treatment protocol (see also FIG. 18).
Figure 32A:
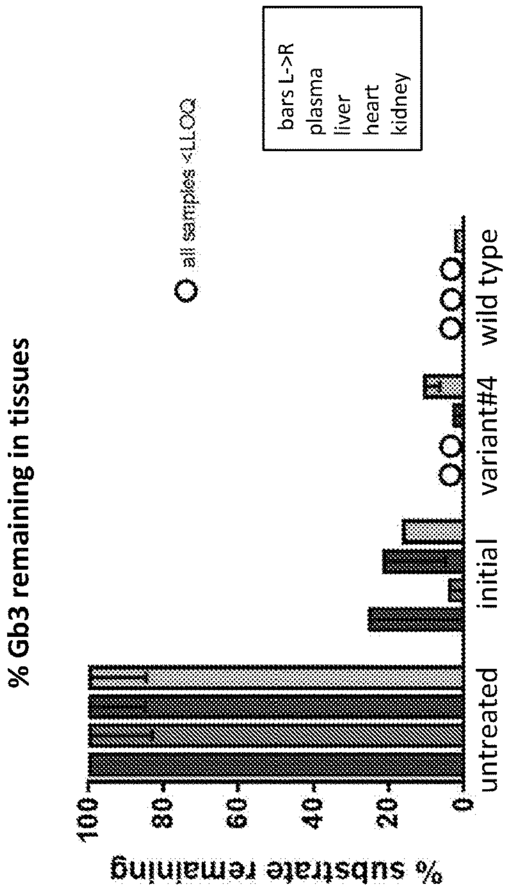
Figure 33A:
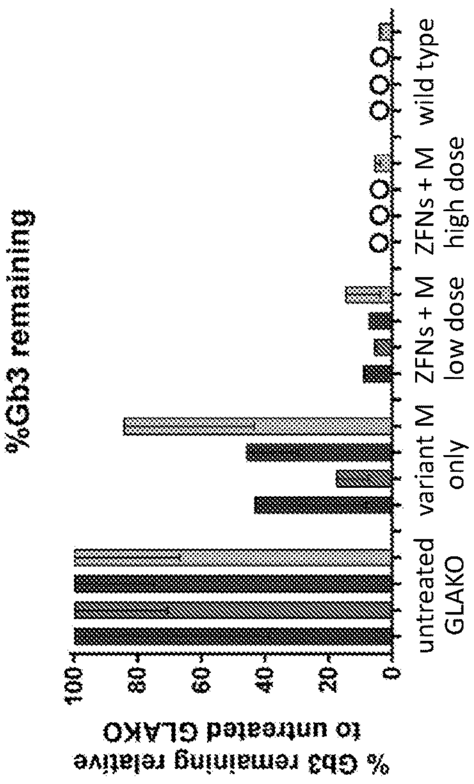
FIGS. 33A and 33B are graphs depicting the percent of Gb3 substrate remaining in various tissues of interest (plasma, liver, heart and kidney) after the indicated treatment protocol (see also FIG. 27).
Figure 33B:
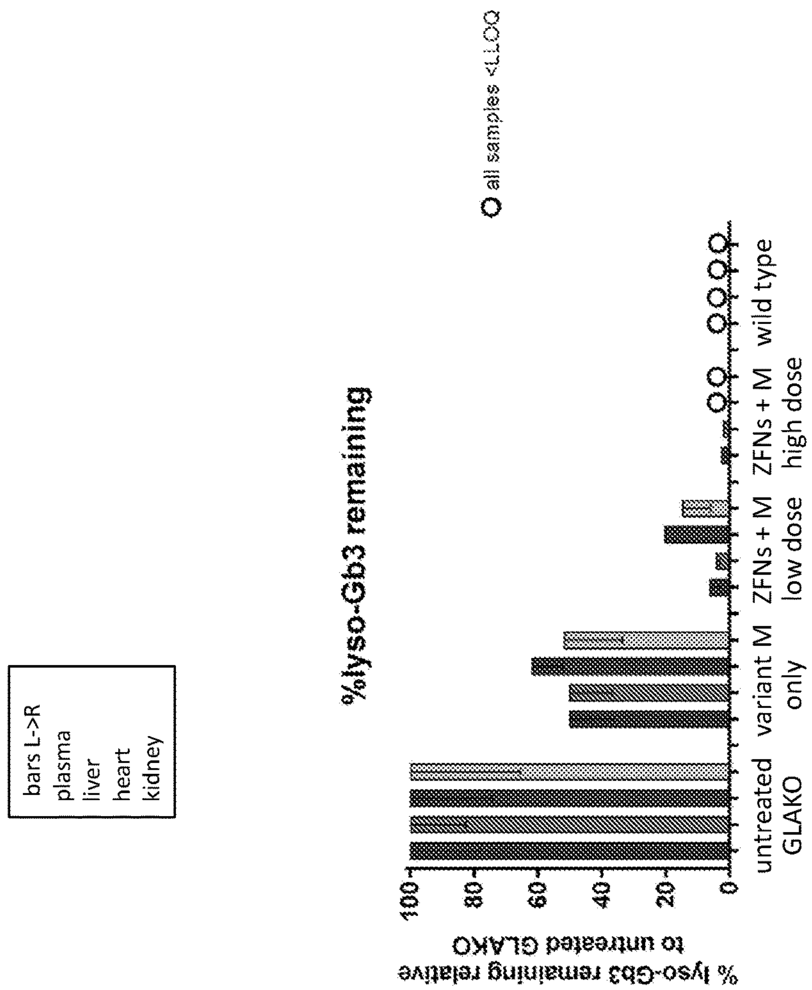

GLAKO mice were treated intravenously with 2004, of formulation buffer containing 5.0e10 VG (2.0e12 VG/kg) of AAV comprising the cDNA variant #4 (see, FIG. 13) or the initial cDNA construct (FIG. 13B) and plasma α-GalA activity was analyzed for a period of 2 months. α-GalA activity in the plasma of GLAKO mice treated with Variant #4 was approximately 10× that observed for the initial cDNA construct (FIG. 18A). As described above, activity was also measured in the liver, heart, kidney and spleen for the two treatment groups and is displayed in FIG. 18B. Further, α-GalA protein was analyzed in the livers of the treated mice and changes in molecular weight were observed following treatment with PNGase F or Endo H as discussed above (FIG. 18C). Additionally, as shown in FIG. 32, GLAKO mice treated with both the initial and Variant #4 cDNAs exhibited reduced Fabry substrate concentration in all tissues tested.

These data demonstrate that the cDNA approach is also a robust platform for the production of α-GalA protein at therapeutically beneficial levels in vivo.

Example 10: In Vivo Dose Titration in Mice Treated with the Initial cDNA Construct GLAKO mice were treated intravenously with a dose of AAV comprising the initial cDNA construct (FIG. 13B) ranging from 1.25e11 VG/kg to 5.0e12 VG/kg and plasma α-GalA activity was analyzed for a period of 6 months as described in Examples 4 and 5.

Figure 19:
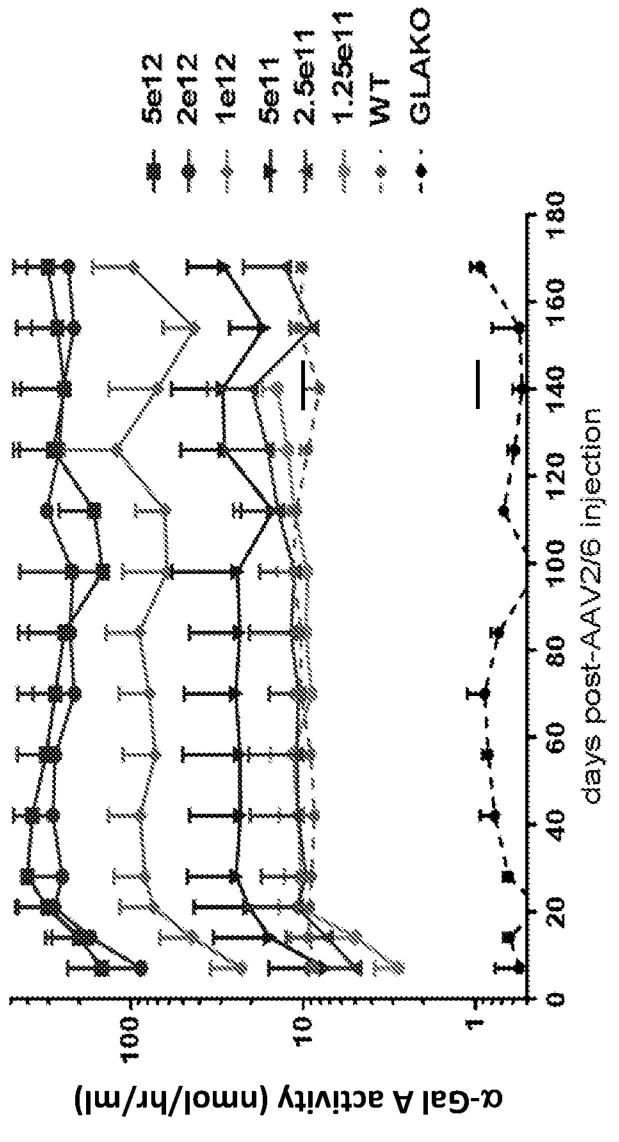
FIG. 19 is a graph depicting the level of α-Gal A activity in the plasma of mice treated with the initial cDNA construct (shown in FIG. 13). Each group was treated with AAV comprising the construct at the doses indicated, from 1.25e11 to 5.0e12 vg/kg (solid lines, group averages indicated by the error bars.) Wild type and untreated GLAKO mice were included as well and are indicated on the figure.
Figure 29:
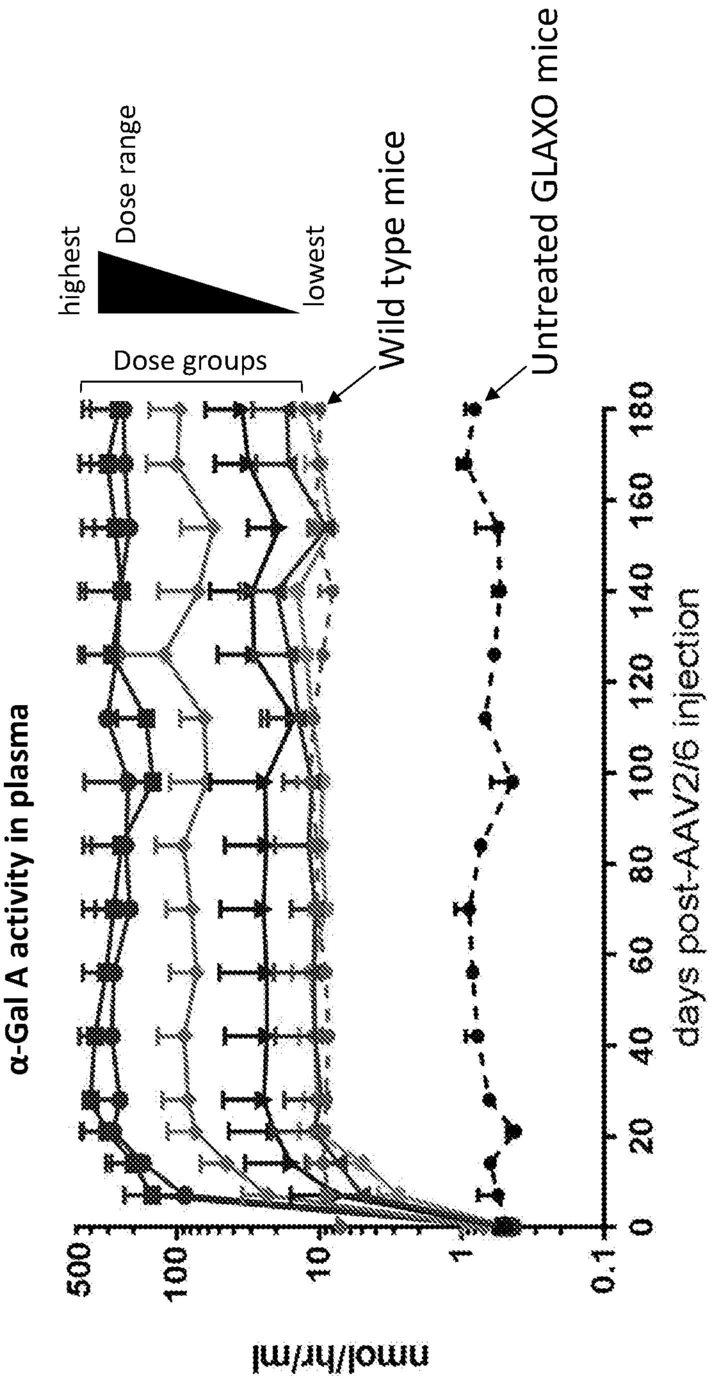
FIG. 29 is a graph depicting α-GAL A activity in plasma of GLAXO mice dosed with 1.25e11 to 5.0e12 VG/KG of the initial cDNA construct (solid lines, group averages, n=4 to 7 per group) and followed for 6 months. Wild type (grey dotted line, indicated by an arrow) and untreated GLAKO mice (black dotted line, indicated by an arrow) are also shown.
Figure 30:
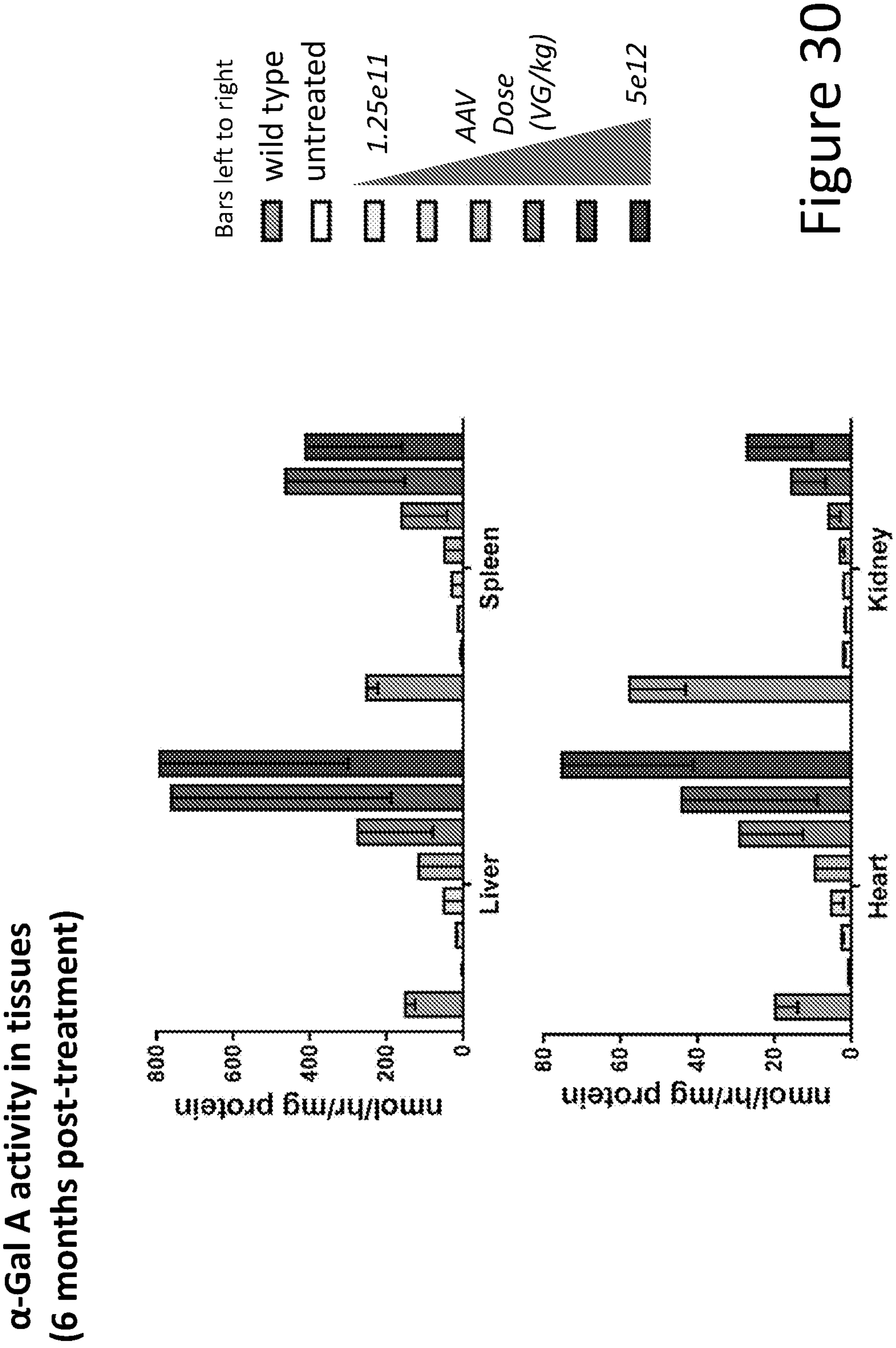
FIG. 30 shows graphs depicting α-Gal A activity in the indicated tissues (liver, spleen, heart and kidney) at 6 months post-treatment with the indicated dosages. Also shown are wild-type and untreated animals.
Figure 31:
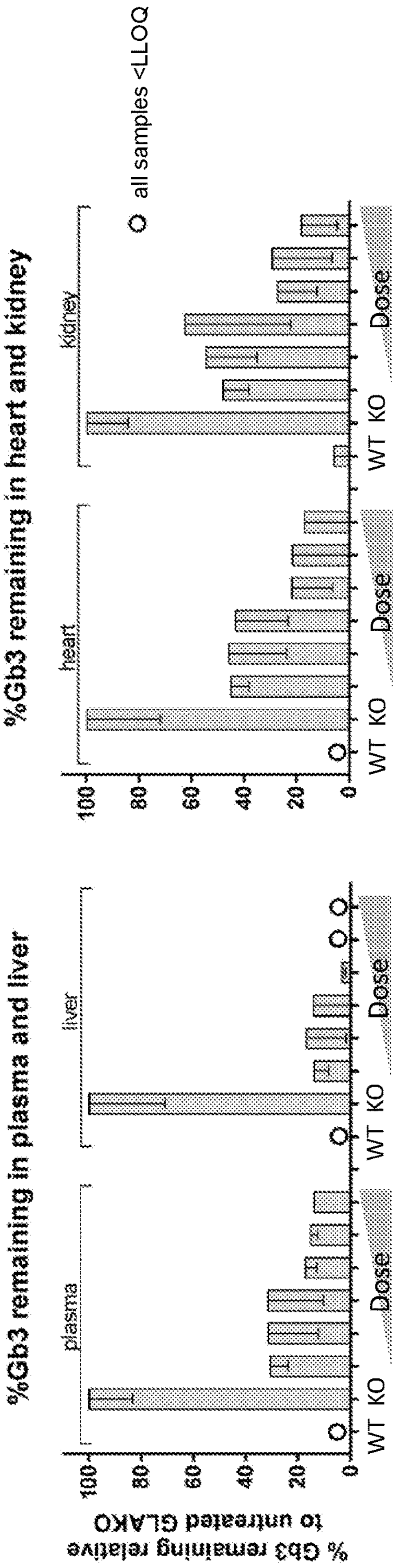
FIG. 31 shows graphs depicting a dose-dependent reduction in Fabry substrate Gb3 content in the indicated tissues (liver, spleen, heart and kidney) in GLAKO mice with 1.25e11 to 5.0e12 VG/KG of the initial cDNA construct as % reduction from untreated GLAKO mice (group averages, n=4 to 7 per group). Mice displayed a dose-dependent reduction in Gb3 content in all tissues measured.

GLAKO mice treated with the initial cDNA had dose-dependent α-GalA activity in the plasma ranging from 1× of wild type up to 40× wild type (FIG. 19). In addition, as shown in FIG. 29, α-Gal A activity remained at therapeutic levels (in a dose-dependent manner) for 6 months post-transduction, indicating long-term therapeutic benefit. FIG. 30 shows α-Gal A activity in liver, spleen, heart and kidney at day 180 (6 months post-treatment) and also shows therapeutic levels in these tissues. The dose-dependent increase in α-Gal A activity also corresponded to a reduction in Gb3 substrate content. See, FIGS. 31 and 32, showing a dose-dependent reduction in Gb3 content in all tissues evaluated.

The data demonstrate that therapeutic levels of α-Gal A protein are generated in subjects treated with the cDNA approach described herein.

Example 11: Further In Vivo IVPRP Studies

GLAKO mice were treated with ZFNs and various exemplary hGLA donor constructs and evaluated as described above for genomic modification, GLA activity in vivo and reduction of Fabry substrates in vivo. See, Example 5.

Figure 22:
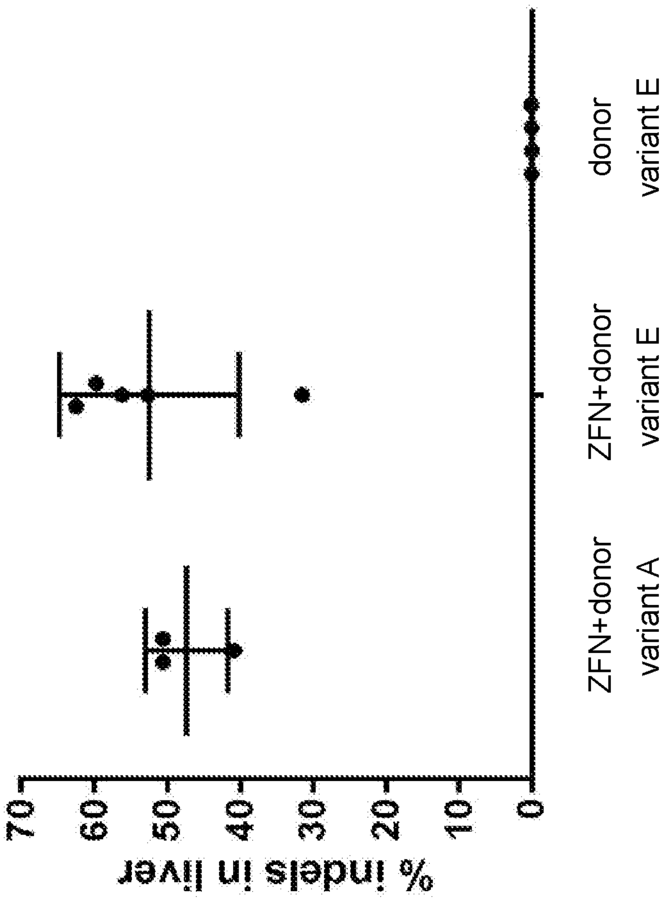
FIG. 22 is a graph depicting permanent modification of hepatocytes in a GLAKO mouse model of Fabry disease following nuclease-mediated targeted integration of a GLA transgene and shows the percentage of indels in liver cells treated under the indicated conditions.
Figure 23A:
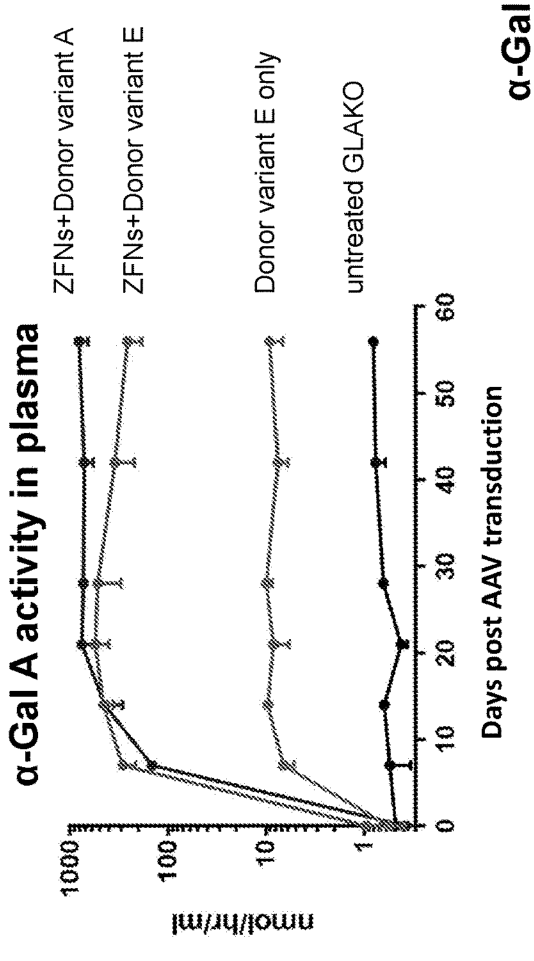
FIGS. 23A and 23B are graphs depicting α-Gal A expressed from the integrated transgene, secreted into the bloodstream and taken up by secondary tissues. GLAKO mice were treated with ZFNs and one of two hGLA donor constructs.
Figure 23B:
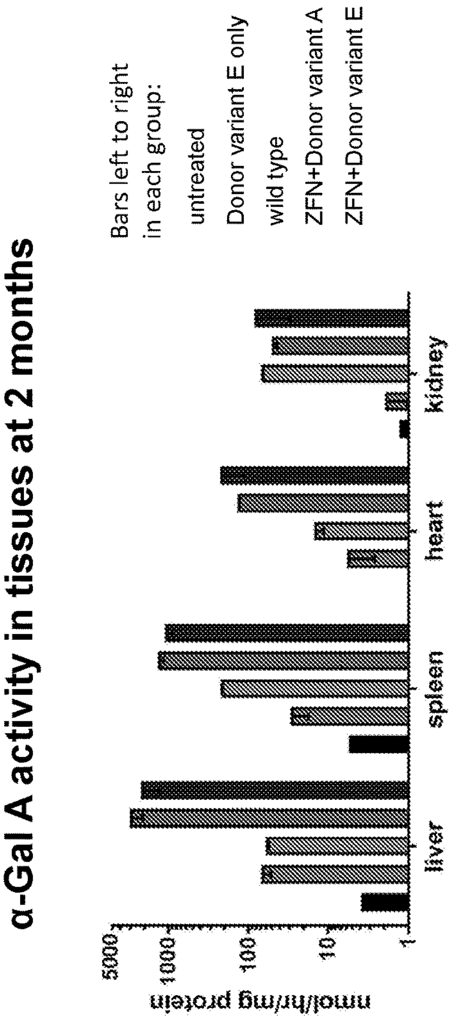
Figure 24B:
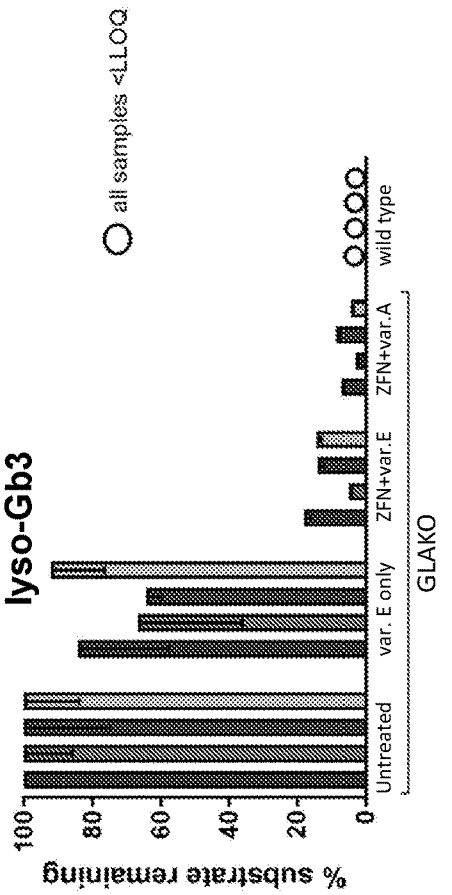
FIGS. 24A and 24B are graphs depicting Fabry substrate content in the indicated tissues.
Figure 24A:
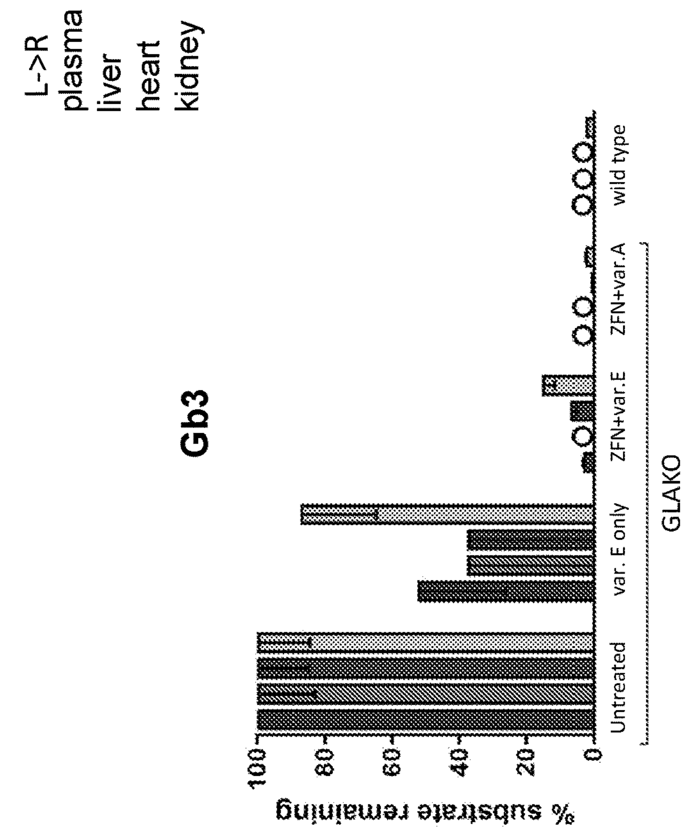
Figure 25A:
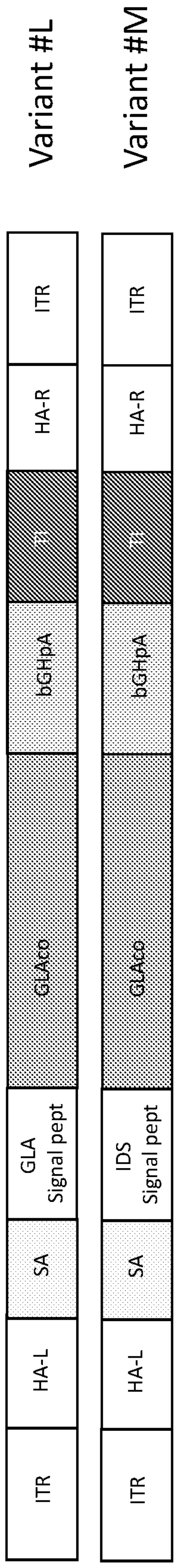
FIGS. 25A and 25B show schematics of Variant L and Variant M and targeted integration into the wild-type albumin locus.
Figure 25B:
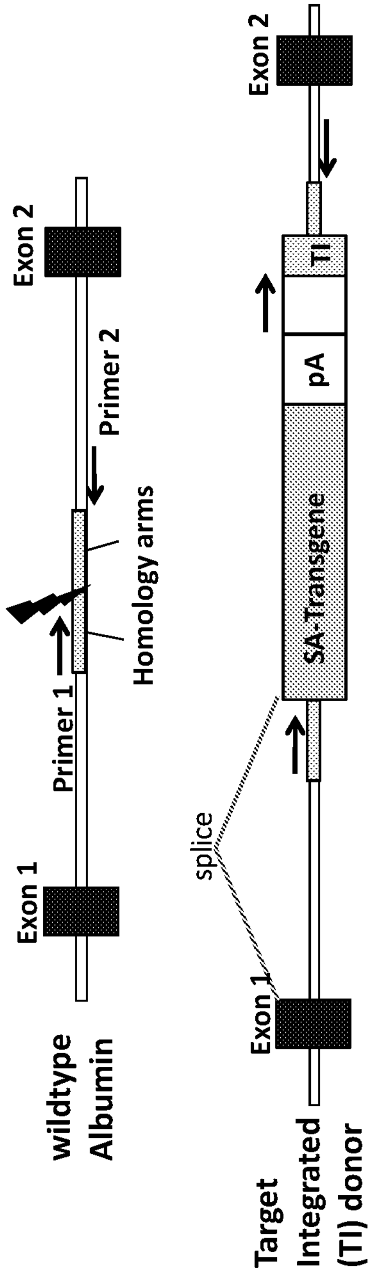

As shown in FIG. 22, nuclease-mediated integration of GLA donors resulted in permanent modification of hepatocytes in the GLAKO mouse model of Fabry disease. FIG. 23 shows α-Gal A activity in the indicated tissues over time (FIG. 23A) and at two months (FIG. 23B) post-administration of nuclease and GLA donors to the animals. As shown, liver-produced α-Gal A is secreted into the bloodstream and taken up by secondary tissues, including that stable plasma activity reached up to 80-fold wild type. FIG. 24 shows the animals treated with nucleases and donors exhibited greatly reduced substrate concentration in all tissues tested, as compared to untreated animals, wild-type animals and animals treated with the donors only.

Experiments in HepG2 and GLAKO mice were conducted using Variant L and a modified donor designated Variant M (FIG. 25) which includes an IDS signal peptide in place of the GLA signal peptide of Variant L.

For detection of L and M donor integration, a NGS approach was used, based on an unbiased PCR scheme that generates different products when the donor has integrated versus the product generated for the wild type gene devoid of an integration event. Briefly, a 5-NGS primer sequences (identical to Primer 1 in FIG. 25B) was added at the 3' end of the transgene (see FIG. 25A). Immediately downstream of the NGS primer sequence, a Targeted Integration (TI) sequence was added. The TI sequence has the same base composition and length as the corresponding sequence in the albumin locus, but the base sequence is scrambled such that no PCR bias is introduced for the amplification of the PCR product associated with the wild type locus without an integration as compared with to the locus comprising the transgene integration. The two PCR products thus utilize identical primers, and produce PCR products of identical size and composition, but have differing sequences, allowing ready identification of TI events by NGS, as well as simultaneous analysis of indels and TI events by NGS.

For analysis of integration events in human cells, the primers used are the following:

```
Primer 1:
                               (SEQ ID NO: 6)
5' GCACTAAGGAAAGTGCAAAG

Primer 2:
                               (SEQ ID NO: 7)
5' TAATACTCTTTTAGTGTCTA
```

The TI sequence used in human cells is shown below where the scrambled sequence is shown in italics, and the location of the Primer 1 binding site is shown in underline:

(SEQ ID NO: 8)

5'GCACTAAGGAAAGTGCAAAGTAA*GATTGACCAGACCAGATAGAAGAAT*

*GTAACTGTAGTTCTAATAGGACTTAT*TATCCCAAAGAC.

Amplification using the two primers produces a 222 bp amplicon as shown below:

Wild Type Amplicon (No Insertion):

```
                                          (SEQ ID NO: 9)
5'GCACTAAGGAAAGTGCAAAGTAACTTAGAGTGACTGAAACTTCACAGA

ATAGGGTTGAAGATTGAATTCATAACTATCCCAAAGACCTATCCATTGCA
```

-continued

CTATGCTTTATTTAAAAACCACAAAACCTGTGCTGTTGATCTCATAAATA

GAACTTGTATTTATATTTATTTTCATTTTAGTCTGTCTTCTTGGTTGCTG

TTGATAGACACTAAAAGAGTATTA.

TI Amplicon (Italics Indicate the Scrambled Sequence):

(SEQ ID NO: 10)

5'GCACTAAGGAAAGTGCAAAGTAA*GATTGACCAGACCAGATAGAAGAAT*

*GTAACTGTAGTTCTAATAGGACTTATTAT*CCCAAAGACCTATCCATTGCA

CTATGCTTTATTTAAAAACCACAAAACCTGTGCTGTTGATCTCATAAATA

GAACTTGTATTTATATTTATTTTCATTTTAGTCTGTCTTCTTGGTTGCTG

TTGATAGACACTAAAAGAGTATTA.

Similarly, the TI sequence and primers used for mouse cells is shown below. For analysis of integration events, the primers used are as follows:

Primer 1:

(SEQ ID NO: 11)

5' TTGAGTTTGAATGCACAGAT

Primer 2:

(SEQ ID NO: 12)

5' GAAACAGGGAGAGAAAAACC.

The TI sequence used in mouse cells is shown below where the scrambled sequence is shown in italics, and the location of the Primer 1 binding site is shown in underline:

(SEQ ID NO: 13)

5'AAATCTTGAGTTTGAATGCACAGAT*CAATTGTAAACTAAAGAA*

*ATAGTAATATAGAGTTTAAATATAGATAGCTATGACTGCACTTGATA*

*GAAGGTAACGG*TGCCACCTTCAGATTT

Amplification using the two primers produces a 247 bp amplicon as shown below:

Wild Type Amplicon (No Insertion):

(SEQ ID NO: 14)

5'TTGAGTTTGAATGCACAGATATAAACACTTAACGGGTTTTAAAAATAA

TAATGTTGGTGAAAAAATATAACTTTGAGTGTAGCAGAGAGGAACCATTG

CCACCTTCAGATTTTCCTGTAACGATCGGGAACTGGCATCTTCAGGGAGT

AGCTTAGGTCAGTGAAGAGAAGAACAAAAAGCAGCATATTACAGTTAGTT

GTCTTCATCAATCTTTAAATATGTTGTGTGGTTTTTCTCTCCCTGTTTC

TI Amplicon (Italics Indicate the Scrambled Sequence):

(SEQ ID NO: 15)

5'TTGAGTTTGAATGCACAGAT*CAATTGTAAACTAAAGAAATAGTAATAT*

*AGAGTTTAAATATAGATAGCTATGACTGCACTTGATAGAAGGTAACGG*TG

CCACCTTCAGATTTTCCTGTAACGATCGGGAACTGGCATCTTCAGGGAGT

AGCTTAGGTCAGTGAAGAGAAGAACAAAAAGCAGCATATTACAGTTAGTT

GTCTTCATCAATCTTTAAATATGTTGTGTGGTTTTTCTCTCCCTGTTTC

Further, this technique can be used with non-human primates (rhesus macaque, NHP) utilizing the primers and inserted TI sequence shown below:

Primer 1:

(SEQ ID NO: 16)

5' CCACTAAGGAAAGTGCAAAG

Primer 2:

(SEQ ID NO: 17)

5' TGAAAGTAAATATAAATACAAGTTC

The TI sequence used in NHP cells is shown below where the scrambled sequence is shown in italics, and the location of the Primer 1 binding site is shown in underline:

(SEQ ID NO: 18)

5'CCACTAAGGAAAGTGCAAAG*GAGCGCTAACTGGAACATACTCGCTATT*

*TAAGAACATTATAAGATACTAATTCAGTATTCG*AAGAC.

Amplification using the two primers produces a 173 bp amplicon as shown below:

Wild type amplicon (no insertion): 5'CCACTAAGGAAAGTGCAAAG TAACTTAGAGTGACTTAAACTTCACAGAACAGAGTTGAAGATTGAATTCATA ACTGTCCCTAAGACCTATCCATTGCACTATGCTTTATTTAAAAGCCACAAAAC CTGTGCTGTTGATCTCATAAATAGAACTTGTATTTATATTTACTTTCA (SEQ ID NO:19)

TI Amplicon (Italics Indicate the Scrambled Sequence):

(SEQ ID NO: 20)

5'CCACTAAGGAAAGTGCAAAG*GAGCGCTAACTGGAACATACTCGCTATT*

*TAAGAACATTATAAGATACTAATTCAGTATTCG*AAGACCTATCCATTGCA

CTATGCTTTATTTAAAAGCCACAAAACCTGTGCTGTTGATCTCATAAATA

GAACTTGTATTTATATTTACTTTCA.

Thus, human cells from the hepatocarinoma cell line HepG2 were treated with ZFNs and GLA donor variant #L, containing a TI sequence for analysis of HDR. DNA was purified from transduced cells 7 days after transduction and analyzed via NGS.

Figure 26A:
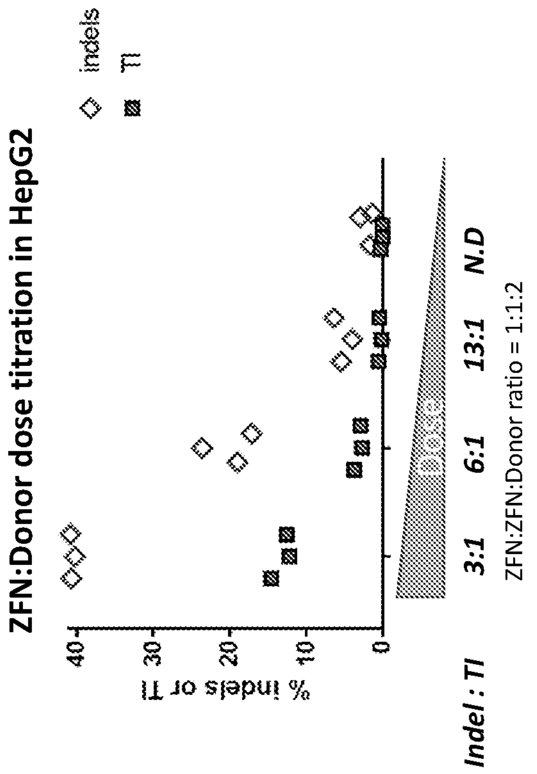
FIGS. 26A and 26B are graphs depicting modification (percent indels or percent TI) using the indicated donors into the human hematocarcinoma cell line HepG2 at the indicated dosages.
Figure 26B:
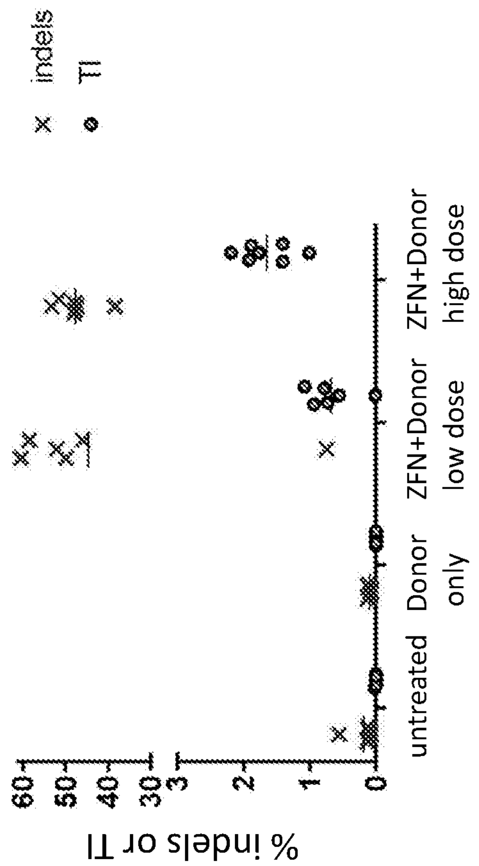

As shown in FIG. 26, in vitro indels and TI (HDR) showed a dose-dependent response to a fixed ratio of ZFNs and TI donor. Furthermore, as shown in GLAKO mice, the nuclease-mediated targeted integration (TI) of Variant M yielded stable plasma activity up to 250-fold wild type and α-Gal A activity in heart and kidney was over 20-fold wild type and 4-fold wild type, respectively.

Assays were also conducted to further assess whether α-Gal A is taken up by secondary tissues following nuclease-mediated TI of a GLA donor construct. Briefly, as described above, a GLA donor construct containing an IDS signal peptide and a 3' sequence for analysis of targeted integration (TI) (Donor Variant M) was used to treat GLAKO mice and plasma and tissue samples (e.g., liver, heart, spleen, kidney, brain, etc.) assayed for both α-Gal A activity and substrate concentration.

Figure 27A:
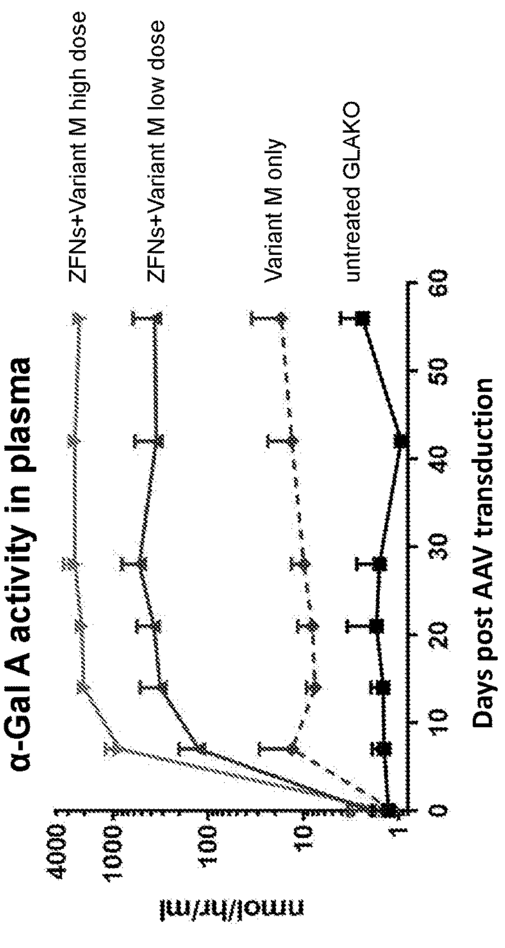
FIGS. 27A and 27B are graphs depicting how liver-produced α-Gal A is secreted into the bloodstream and taken up by secondary tissues. A GLA donor construct containing an IDS signal peptide and a 3' sequence for analysis of targeted integration (TI) was used to treat GLAKO mice.
Figure 27B:
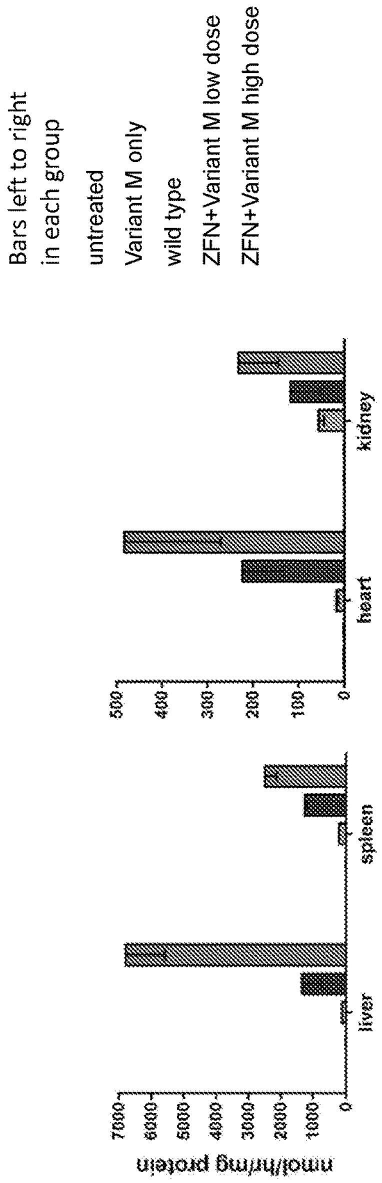

As shown in FIG. 27, α-Gal A stable plasma activity was up to 250-fold wild type and α-Gal A activity in heart and kidney was over 20-fold wild type and 4-fold wild type, respectively.

The data demonstrate that therapeutic levels of α-Gal A protein are generated in subjects (including secondary tissues) treated with the IVPRP approach described herein.

All patents, patent applications and publications mentioned herein are hereby incorporated by reference in their entirety.

Although disclosure has been provided in some detail by way of illustration and example for the purposes of clarity of understanding, it will be apparent to those skilled in the art that various changes and modifications can be practiced without departing from the spirit or scope of the disclosure. Accordingly, the foregoing descriptions and examples should not be construed as limiting.

What is claimed is:

1. A pharmaceutical composition comprising an adeno-associated virus (AAV) expression construct, wherein the AAV expression construct comprises an apolipoprotein E (APOE) enhancer operably linked to an alpha 1-antitrypsin (hAAT) promoter, a human hemoglobin beta (HBB)-IGG intron, and a cDNA transgene encoding at least one a galactosidase A (α-Gal A) protein, and a pharmaceutically acceptable carrier or excipient.

2. The pharmaceutical composition of claim 1, wherein the AAV expression construct further comprises a sequence encoding a signal peptide.

3. The pharmaceutical composition of claim 1, wherein the AAV expression construct further comprises a poly A signal sequence.

4. The pharmaceutical composition of claim 1, wherein the transgene comprises a wild-type α-Gal A sequence or a codon-optimized α-Gal A sequence.

5. The pharmaceutical composition of claim 2, wherein the signal peptide is an α-Gal A signal peptide.

6. An adeno-associated virus (AAV) expression construct, wherein the AAV expression construct comprises an apolipoprotein E (APOE) enhancer operably linked to an alpha 1-antitrypsin (hAAT) promoter, a human hemoglobin beta (HBB)-IGG intron, and a cDNA transgene encoding at least one a galactosidase A (α-Gal A) protein.

7. The AAV expression construct of claim 6, wherein the AAV expression construct further comprises a sequence encoding a signal peptide.

8. The AAV expression construct of claim 7, wherein the signal peptide is an α-Gal A signal peptide.

9. The AAV expression construct of 6, wherein the AAV expression construct further comprises a poly A signal sequence.

10. The AAV expression construct of claim 9, wherein the polyA signal sequence is a bovine growth hormone poly A signal sequence.

11. The AAV expression construct of claim 6, wherein the transgene comprises a wild-type α-Gal A sequence or a codon optimized α-Gal A sequence.

12. An adeno-associated virus (AAV) expression construct comprising an apolipoprotein E (APOE) enhancer linked to an alpha 1-antitrypsin (hAAT) promoter, a human hemoglobin beta (HBB)-IGG intron, a sequence encoding an α-Gal A signal peptide, a cDNA transgene encoding at least one alpha-galactosidase A (α-Gal A) protein, and a bovine growth hormone poly A signal sequence.

13. The AAV expression construct of claim 6, wherein the AAV expression construct is capable of expressing at least one α-Gal A protein from the transgene in a subject in need thereof.

14. The AAV expression construct of claim 13, wherein the at least one α-Gal A protein expressed from the transgene decreases the amount of glycospingolipids in the subject by at least 2-fold.

15. The pharmaceutical composition of claim 3, wherein the polyA signal sequence is a bovine growth hormone poly A signal sequence.

16. The AAV expression construct of claim 11, wherein the transgene comprises a codon optimized α-Gal A sequence.

17. The AAV expression construct of claim 12, wherein the transgene comprises a codon optimized α-Gal A sequence.

18. The pharmaceutical composition of claim 4, wherein the transgene comprises a codon-optimized α-Gal A sequence.

19. The pharmaceutical composition of claim 1, wherein the AAV expression construct is capable of expressing at least one α-Gal A protein from the transgene in a subject in need thereof.

20. The pharmaceutical composition of claim 19, wherein the at least one α-Gal A protein expressed from the transgene decreases the amount of glycospingolipids in the subject by at least 2-fold.

* * * * *

SEQUENCE LISTING

```
<160> NUMBER OF SEQ ID NOS: 21

<210> SEQ ID NO 1
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Met Gln Leu Arg Asn Pro Glu Leu His Leu Gly Cys Ala Leu Ala Leu
1               5                   10                  15

Arg Phe Leu Ala Leu Val Ser Trp Asp Ile Pro Gly Ala Arg Ala
            20                  25                  30


<210> SEQ ID NO 2
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2

gccaccatg                                                                9


<210> SEQ ID NO 3
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Met Pro Pro Pro Arg Thr Gly Arg Gly Leu Leu Trp Leu Gly Leu Val
1               5                   10                  15

Leu Ser Ser Val Cys Val Ala Leu Gly
            20                  25


<210> SEQ ID NO 4
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Met Gln Arg Val Asn Met Ile Met Ala Glu Ser Pro Gly Leu Ile Thr
1               5                   10                  15

Ile Cys Leu Leu Gly Tyr Leu Leu Ser Ala Glu Cys
            20                  25


<210> SEQ ID NO 5
<211> LENGTH: 18
<212> TYPE: PRT
```

<213> ORGANISM: Artificial Sequence
<220> FEATURE:
<223> OTHER INFORMATION: Description of Artificial Sequence: Synthetic
peptide

<400> SEQUENCE: 5

```
Met Lys Trp Val Thr Phe Ile Ser Leu Leu Phe Leu Phe Ser Ser Ala
1               5                   10                  15

Tyr Ser
```

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 6

```
gcactaagga aagtgcaaag                                                20
```

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 7

```
taatactctt ttagtgtcta                                                20
```

<210> SEQ ID NO 8
<211> LENGTH: 86
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 8

```
gcactaagga aagtgcaaag taagattgac cagaccagat agaagaatgt aactgtagtt     60

ctaataggac ttattatccc aaagac                                          86
```

<210> SEQ ID NO 9
<211> LENGTH: 222
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 9

```
gcactaagga aagtgcaaag taacttagag tgactgaaac ttcacagaat agggttgaag     60

attgaattca taactatccc aaagacctat ccattgcact atgctttatt taaaaaccac    120

aaaacctgtg ctgttgatct cataaataga acttgtattt atatttattt tcattttagt    180

ctgtcttctt ggttgctgtt gatagacact aaaagagtat ta                       222
```

<210> SEQ ID NO 10
<211> LENGTH: 222
<212> TYPE: DNA

<213> ORGANISM: Artificial Sequence
<220> FEATURE:
<223> OTHER INFORMATION: Description of Artificial Sequence: Synthetic polynucleotide

<400> SEQUENCE: 10
gcactaagga aagtgcaaag taagattgac cagaccagat agaagaatgt aactgtagtt 60
ctaataggac ttattatccc aaagacctat ccattgcact atgctttatt taaaaaccac 120
aaaacctgtg ctgttgatct cataaataga acttgtattt atatttattt tcattttagt 180
ctgtcttctt ggttgctgtt gatagacact aaaagagtat ta 222

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 11
ttgagtttga atgcacagat 20

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 12
gaaacaggga gagaaaaacc 20

<210> SEQ ID NO 13
<211> LENGTH: 117
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 13
aaatcttgag tttgaatgca cagatcaatt gtaaactaaa gaaatagtaa tatagagttt 60
aaatatagat agctatgact gcacttgata gaaggtaacg gtgccacctt cagattt 117

<210> SEQ ID NO 14
<211> LENGTH: 247
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 14
ttgagtttga atgcacagat ataaacactt aacgggtttt aaaaataata atgttggtga 60
aaaaatataa ctttgagtgt agcagagagg aaccattgcc accttcagat tttcctgtaa 120
cgatcgggaa ctggcatctt cagggagtag cttaggtcag tgaagagaag aacaaaaagc 180
agcatattac agttagttgt cttcatcaat ctttaaatat gttgtgtggt ttttctctcc 240
ctgtttc 247

<210> SEQ ID NO 15

<211> LENGTH: 247
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 15
ttgagtttga atgcacagat caattgtaaa ctaaagaaat agtaatatag agtttaaata 60
tagatagcta tgactgcact tgatagaagg taacggtgcc accttcagat tttcctgtaa 120
cgatcgggaa ctggcatctt cagggagtag cttaggtcag tgaagagaag aacaaaaagc 180
agcatattac agttagttgt cttcatcaat ctttaaatat gttgtgtggt ttttctctcc 240
ctgtttc 247

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 16
ccactaagga aagtgcaaag 20

<210> SEQ ID NO 17
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 17
tgaaagtaaa tataaataca agttc 25

<210> SEQ ID NO 18
<211> LENGTH: 86
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 18
ccactaagga aagtgcaaag gagcgctaac tggaacatac tcgctattta agaacattat 60
aagatactaa ttcagtattc gaagac 86

<210> SEQ ID NO 19
<211> LENGTH: 173
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 19
ccactaagga aagtgcaaag taacttagag tgacttaaac ttcacagaac agagttgaag 60
attgaattca taactgtccc taagacctat ccattgcact atgctttatt taaaagccac 120
aaaacctgtg ctgttgatct cataaataga acttgtattt atatttactt tca 173

<210> SEQ ID NO 20

-continued

```
<211> LENGTH: 173
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 20

ccactaagga aagtgcaaag gagcgctaac tggaacatac tcgctattta agaacattat      60

aagatactaa ttcagtattc gaagacctat ccattgcact atgctttatt taaaagccac     120

aaaacctgtg ctgttgatct cataaataga acttgtattt atatttactt tca            173


<210> SEQ ID NO 21
<211> LENGTH: 9
<212> TYPE: PRT
<213> ORGANISM: Unknown
<220> FEATURE:
<223> OTHER INFORMATION: Description of Unknown:
      "LAGLIDADG" homing endonuclease sequence

<400> SEQUENCE: 21

Leu Ala Gly Leu Ile Asp Ala Asp Gly
1               5
```